(12) United States Patent
Honda et al.

(10) Patent No.: US 12,390,499 B2
(45) Date of Patent: Aug. 19, 2025

(54) BACTERIOPHAGE FOR MODULATING INFLAMMATORY BOWEL DISEASE

(71) Applicants: Keio University, Tokyo (JP); Biomx Ltd., Nes Ziona (IL)

(72) Inventors: Kenya Honda, Tokyo (JP); Koji Atarashi, Tokyo (JP); Seiko Narushima, Tokyo (JP); Efrat Khabra, Petach Tikva (IL); Hava Ben David, Rehovot (IL); Eyal Weinstock, Kfar Shmaryahu (IL); Yulia Matiuhin, Pardes Chana-Karkur (IL); Naomi Bluma Zak, Jerusalem (IL)

(73) Assignees: KEIO UNIVERSITY, Tokyo (JP); BIOMX LTD., Nes Ziona (IL)

( * ) Notice: Subject to any disclaimer, the term of this patent is extended or adjusted under 35 U.S.C. 154(b) by 866 days.

(21) Appl. No.: 17/436,693

(22) PCT Filed: Mar. 6, 2020

(86) PCT No.: PCT/IB2020/000182
§ 371 (c)(1),
(2) Date: Sep. 7, 2021

(87) PCT Pub. No.: WO2020/178636
PCT Pub. Date: Sep. 10, 2020

(65) Prior Publication Data
US 2022/0152132 A1    May 19, 2022

Related U.S. Application Data

(60) Provisional application No. 62/815,265, filed on Mar. 7, 2019.

(51) Int. Cl.
*A61K 35/76* (2015.01)
*A61P 31/04* (2006.01)

(52) U.S. Cl.
CPC ............. *A61K 35/76* (2013.01); *A61P 31/04* (2018.01)

(58) Field of Classification Search
CPC ................... A61K 35/76; A61P 31/04; C12N 2795/10121; C12N 2795/10132; C12N 2795/10221; C12N 2795/10232; C12N 2795/10321; C12N 2795/10332
See application file for complete search history.

(56) References Cited

U.S. PATENT DOCUMENTS

| | | |
|---|---|---|
| 2009/0304638 A1 | 12/2009 | Yoon et al. |
| 2011/0217756 A1 | 9/2011 | Tsao et al. |

FOREIGN PATENT DOCUMENTS

| | | |
|---|---|---|
| KR | 10-2013-0087118 | 8/2013 |
| KR | 10-2018-0137814 | 12/2018 |
| WO | WO 2007/113657 | 10/2007 |
| WO | WO 2019/048930 | 3/2019 |

OTHER PUBLICATIONS

Lee et al. (In-Ah Lee & Dong-Hyun Kim (2011) Klebsiella pneumoniae increases the risk of inflammation and colitis in a murine model of intestinal bowel disease, Scandinavian Journal of Gastroenterology, 46:6, 684-693. DOI: 10.3109/00365521.2011.560678) (Year: 2011).*
International Search Report and the Written Opinion Dated Jun. 12, 2020 From the International Searching Authority Re. Application No. PCT/IB2020/000182. (15 Pages).
International Preliminary Report on Patentability Dated Sep. 16, 2021 From the International Bureau of WIPO Re. Application No. PCT/IB2020/000182. (11 Pages).

* cited by examiner

*Primary Examiner* — Kade Ariani
(74) *Attorney, Agent, or Firm* — McCarter & English, LLP

(57) ABSTRACT

Disclosed herein are bacteriophage compositions and therapeutic uses thereof. The disclosure also relates to bacteriophage that are capable of lysing *Klebsiella* bacterial strains, e.g., strains that are associated with inflammatory bowel disease, and thereby capable of modulating disease.

13 Claims, 28 Drawing Sheets

Specification includes a Sequence Listing.

| name | family | subfamily | genus | KP2 |
|---|---|---|---|---|
| 1.2-2 | Myoviridae | Tevenvirinae | Kp15virus | S |
| PKP-55 | Myoviridae | Tevenvirinae | Kp15virus | S |
| colon-11 | Myoviridae | Tevenvirinae | Kp15virus | S |
| 1.2-4br | Myoviridae | Tevenvirinae | T4virus | S |
| 1.2-4s | Myoviridae | Tevenvirinae | T4virus | S |
| KP2-5-1 | Myoviridae | Tevenvirinae | T4virus | S |
| KP2-4a | Myoviridae | Tevenvirinae | T4virus | S |
| M16-4a | Myoviridae | Tevenvirinae | T4virus | S |
| KP2-9a | Myoviridae | Tevenvirinae | T4virus | S |
| M16-9a | Myoviridae | Tevenvirinae | T4virus | S |
| colon-14-15 | Myoviridae | Tevenvirinae | T4virus | S |
| colon-6 | Myoviridae | Tevenvirinae | T4virus | S |
| colon-1 | Myoviridae | Tevenvirinae | T4virus | S |
| colon-36 | Myoviridae | Tevenvirinae | T4virus | S |
| KP2-5a | Myoviridae | Tevenvirinae | T4virus | S |
| M16-3-2c | Myoviridae | Tevenvirinae | T4virus | S |
| M16-5c | Myoviridae | Tevenvirinae | T4virus | R |
| M16-6c | Myoviridae | Tevenvirinae | T4virus | S |
| M16-7a | Myoviridae | Tevenvirinae | T4virus | S |
| KP2-14 | Podoviridae | Autographivirinae | T7virus | S |
| KP2-15-1 | Podoviridae | Autographivirinae | T7virus | S |
| KP2-15-2-1 | Podoviridae | Autographivirinae | T7virus | S |
| 1.2-3b | Podoviridae | Autographivirinae | T7virus | S |
| colon-14 | Podoviridae | Autographivirinae | T7virus | S |
| KP2-8c | Podoviridae | Autographivirinae | T7virus | S |
| KP2-8a | Podoviridae | Autographivirinae | T7virus | S |
| KP2-7-1c | Podoviridae | Autographivirinae | T7virus | S |
| KP2-7c | Podoviridae | Autographivirinae | T7virus | S |
| KP2-16-1 | Podoviridae | Autographivirinae | T7virus | S |
| KP2-5 | Podoviridae | Autographivirinae | T7virus | S |
| Mcoc3c | Podoviridae | Autographivirinae | Kp34virus | R |
| MCoc4c | Podoviridae | Autographivirinae | Kp34virus | R |
| MCoc5c | Podoviridae | Autographivirinae | Kp34virus | R |
| MCoc6c | Podoviridae | Autographivirinae | Kp34virus | R |
| MCoc7c | Podoviridae | Autographivirinae | Kp34virus | R |
| M16-9-1c | Podoviridae | Autographivirinae | Kp34virus | R |
| MCoc9-1c | Podoviridae | Autographivirinae | Kp34virus | R |
| MCoc9-2c | Podoviridae | Autographivirinae | Kp34virus | R |
| MCoc15c | Podoviridae | Autographivirinae | Kp34virus | R |
| MCoc8a | Podoviridae | Autographivirinae | Kp34virus | R |
| 8M-8 | Myoviridae | Vequintavirinae | Sc1virus | R |
| 1.2-3s | Siphoviridae | - | T5virus | S |
| 8M-7 | Siphoviridae | - | T5virus | R |
| 8M-1 | Siphoviridae |  |  | S |

| CT-123-1 | CT-141-1 | MKP2_2161_1 | MKP2_251_B | MKP2_251_C | 8M-all |
|---|---|---|---|---|---|
| S | R | S | S | R | R |
| S | R | S | S | R | R |
| S | R | S | S | R | R |
| S | R | S | R | R | R |
| S | R | S | R | R | R |
| S | R | S | R | R | R |
| S | R | S | R | R | R |
| S | R | S | R | R | R |
| S | R | S | S | R | R |
| S | R | S | R | R | R |
| S | R | S | S | R | R |
| S | R | S | R | R | R |
| S | R | S | R | R | R |
| S | R | S | S | R | R |
| S | R | S | R | R | R |
| S | R | S | R | R | R |
| S | R | S | R | R | R |
| S | R | S | R | R | R |
| S | R | S | R | R | R |
| R | R | R | S | R | R |
| R | R | R | S | R | R |
| R | R | R | S | R | R |
| R | R | R | S | R | R |
| R | R | R | S | R | R |
| R | R | R | S | R | R |
| R | R | R | S | R | R |
| R | R | R | S | R | R |
| R | R | R | S | R | R |
| R | R | R | S | R | R |
| S | S | S | R | S | R |
| S | S | S | R | S | R |
| S | S | S | R | S | R |
| S | S | S | R | S | R |
| S | S | S | R | S | R |
| S | S | S | R | R | S |
| S | S | S | R | S | R |
| S | S | S | R | S | R |
| S | S | S | R | S | R |
| S | S | S | R | S | R |
| S | R | S | R | R | S |
| S | R | S | S | R | R |
| S | R | R | R | R | S |
| S | R | S | S | R | S |

FIG. 1 (CONT.)

FROM FIG.1

|         | colon-11 | PKP-55  | 1.2-2   | KP2-4a  | M16-4a  | colon-36 | KP2-5-1 | 1.2-4br |
|---------|----------|---------|---------|---------|---------|----------|---------|---------|
| colon-11 | 100.000 | 88.330  | 89.326  | 46.322  | 46.189  | 46.172   | 44.927  | 45.392  |
| PKP-55  | 88.330   | 100.000 | 96.680  | 50.975  | 51.038  | 50.961   | 50.651  | 51.207  |
| 1.2-2   | 89.326   | 96.680  | 100.000 | 50.361  | 50.701  | 50.666   | 50.323  | 51.073  |
|         |          |         |         |         |         |          |         |         |
| KP2-4a  | 46.322   | 50.975  | 50.361  | 100.000 | 98.168  | 95.437   | 97.707  | 96.030  |
| M16-4a  | 46.189   | 51.038  | 50.701  | 98.168  | 100.000 | 95.024   | 96.923  | 96.413  |
| colon-36 | 46.172  | 50.961  | 50.666  | 95.437  | 95.024  | 100.000  | 96.273  | 96.502  |
| KP2-5-1 | 44.927   | 50.651  | 50.323  | 97.707  | 96.923  | 96.273   | 100.000 | 98.533  |
| 1.2-4br | 45.392   | 51.207  | 51.073  | 96.030  | 96.413  | 96.502   | 98.533  | 100.000 |
| 1.2-4s  | 45.415   | 51.207  | 51.073  | 96.016  | 96.409  | 96.508   | 98.534  | 100.000 |
| KP2-5a  | 48.451   | 52.918  | 52.493  | 93.451  | 92.955  | 94.313   | 92.973  | 93.033  |
| colon-14-15 | 48.282 | 53.619 | 53.501 | 92.015 | 91.339  | 93.190   | 91.686  | 91.869  |
| colon-6 | 48.401   | 53.660  | 53.501  | 92.003  | 91.343  | 93.472   | 91.688  | 91.869  |
| colon-1 | 46.935   | 52.249  | 51.882  | 92.858  | 91.850  | 93.218   | 92.423  | 92.039  |
| M16-3-2c | 46.618  | 50.874  | 50.548  | 93.118  | 93.569  | 92.669   | 92.687  | 92.625  |
| M16-6c  | 46.381   | 51.522  | 51.143  | 93.689  | 93.283  | 94.485   | 94.209  | 93.625  |
| KP2-9a  | 46.880   | 53.232  | 53.046  | 94.368  | 92.869  | 93.734   | 93.212  | 93.226  |
| M16-9a  | 46.532   | 52.896  | 52.830  | 94.410  | 93.294  | 93.957   | 93.278  | 93.229  |
| M16-5c  | 46.677   | 51.669  | 51.643  | 91.876  | 91.499  | 91.813   | 91.914  | 91.817  |
| M16-7a  | 44.571   | 47.964  | 47.379  | 88.288  | 88.821  | 88.528   | 88.579  | 88.221  |
|         |          |         |         |         |         |          |         |         |
|         | KP2-15-1 | KP2-14  | KP2-15-2-1 | KP2.16-1 | KP2-5 | KP2.7-1c | KP2-7c | KP2-8a |
| KP2-15-1 | 100     | 99.77944 | 99.93557 | 83.38125 | 85.62897 | 85.40345 | 85.56453 | 85.56205 |
| KP2-14  | 99.77944 | 100    | 99.77981 | 87.98049 | 87.70204 | 85.37439 | 85.53583 | 85.53583 |
| KP2-15-2-1 | 99.93557 | 99.77981 | 100 | 88.07751 | 87.79099 | 85.23503 | 85.39584 | 85.39337 |
| KP2-16-1 | 83.38125 | 87.98049 | 88.07751 | 100 | 92.53075 | 94.6746 | 94.67198 | 94.66936 |
| KP2-5   | 85.62897 | 87.70204 | 87.79099 | 92.53075 | 100    | 91.93352 | 91.93097 | 91.92843 |
| KP2-7-1c | 85.40345 | 85.37439 | 85.23503 | 94.6746 | 91.93352 | 100 | 99.99744 | 100 |
| KP2-7c  | 85.56453 | 85.53583 | 85.39584 | 94.67198 | 91.93097 | 99.99744 | 100 | 99.99743 |
| KP2-8a  | 85.56205 | 85.53583 | 85.39337 | 94.66936 | 91.92843 | 100 | 99.99743 | 100 |
| colon-14 | 86.71193 | 89.18009 | 89.15457 | 91.54822 | 93.07423 | 92.63276 | 92.63021 | 92.53324 |
| 1.2-3b  | 85.66118 | 85.62027 | 85.48491 | 93.46059 | 91.31087 | 92.07773 | 92.09582 | 91.97748 |
| KP2-8c  | 85.68349 | 85.64013 | 85.50717 | 93.46846 | 91.34391 | 91.82003 | 91.81746 | 91.71993 |
|         |          |         |         |         |         |          |         |         |
|         | MCoc15c | MCoc8a  | M16-9-1c | MCoc9-1c | MCoc9-2c | MCoc4c | MCoc6c | MCoc3c |
| MCoc15c | 100.000  | 99.998  | 90.194  | 90.240  | 89.906  | 89.733   | 85.601  | 86.588  |
| MCoc8a  | 99.998   | 100.000 | 90.196  | 90.243  | 89.909  | 89.735   | 85.603  | 86.590  |
| M16-9-1c | 90.207  | 90.189  | 100.000 | 99.984  | 99.973  | 90.326   | 88.754  | 87.246  |
| MCoc9-1c | 90.234  | 90.225  | 99.984  | 100.000 | 99.989  | 90.339   | 88.767  | 87.259  |
| MCoc-2c | 89.900   | 89.891  | 99.973  | 99.989  | 100.000 | 90.108   | 88.531  | 87.028  |
| MCoc4c  | 89.648   | 89.671  | 90.216  | 90.229  | 89.998  | 100.000  | 94.572  | 95.720  |
| MCoc6c  | 85.520   | 85.543  | 88.653  | 88.653  | 88.417  | 94.585   | 10.000  | 95.044  |
| MCoc3c  | 86.496   | 86.505  | 87.108  | 87.134  | 86.903  | 95.713   | 95.024  | 10.000  |
| MCoc5c  | 85.729   | 85.739  | 86.862  | 86.884  | 86.650  | 95.001   | 96.034  | 98.882  |
| MCoc7c  | 86.176   | 86.208  | 87.159  | 87.219  | 86.985  | 94.715   | 94.668  | 98.603  |
|         |          |         |         |         |         |          |         |         |
|         | 8M-8     |         |         |         |         |          |         |         |
| 8M-8    | 100.000  |         |         |         |         |          |         |         |
|         |          |         |         |         |         |          |         |         |
|         | 8M-1     |         |         |         |         |          |         |         |
| 8M-1    | 100.000  |         |         |         |         |          |         |         |
|         |          |         |         |         |         |          |         |         |
|         | 1.2-3s   | 8M-7    |         |         |         |          |         |         |
| 1.2-3s  | 100.000  | 4.321   |         |         |         |          |         |         |
| 8m-7    | 4.321    | 100.000 |         |         |         |          |         |         |

| 1.2-4s | KP2-5a | colon-14-15 | colon-6 | colon-1 | M16-3-2c | M16-6c | KP2-9a | M16-9a | M16-5c | M16-7a |
|---|---|---|---|---|---|---|---|---|---|---|
| 45.415 | 48.451 | 48.282 | 48.401 | 46.935 | 46.618 | 46.381 | 46.880 | 46.532 | 46.677 | 44.571 |
| 51.207 | 52.918 | 53.619 | 53.660 | 52.249 | 50.874 | 51.522 | 53.232 | 52.896 | 51.669 | 47.964 |
| 51.073 | 52.493 | 53.501 | 53.501 | 51.882 | 50.548 | 51.143 | 53.046 | 52.830 | 51.643 | 47.379 |
| | | | | | | | | | | |
| 96.016 | 93.451 | 92.015 | 92.003 | 92.858 | 93.118 | 93.689 | 94.368 | 94.410 | 91.876 | 88.288 |
| 96.409 | 92.955 | 91.339 | 91.343 | 91.850 | 93.569 | 93.283 | 92.869 | 93.294 | 91.499 | 88.821 |
| 96.508 | 94.313 | 93.190 | 93.472 | 93.218 | 92.669 | 94.485 | 93.734 | 93.957 | 91.813 | 88.528 |
| 98.534 | 92.973 | 91.686 | 91.688 | 92.423 | 92.687 | 94.209 | 93.212 | 93.278 | 91.914 | 88.579 |
| 100.000 | 93.033 | 91.869 | 91.869 | 92.039 | 92.625 | 93.625 | 93.226 | 93.229 | 91.817 | 88.221 |
| 100.000 | 93.016 | 91.875 | 91.875 | 92.032 | 92.634 | 93.633 | 93.231 | 93.234 | 91.826 | 88.233 |
| 93.016 | 100.000 | 94.579 | 94.588 | 91.945 | 93.174 | 93.757 | 93.119 | 93.312 | 92.327 | 87.877 |
| 91.875 | 94.579 | 100.000 | 100.000 | 93.072 | 93.182 | 91.881 | 93.366 | 93.505 | 92.867 | 88.129 |
| 91.875 | 94.588 | 100.000 | 100.000 | 93.037 | 93.188 | 91.897 | 93.370 | 93.508 | 92.879 | 88.137 |
| 92.032 | 91.945 | 93.072 | 93.037 | 100.000 | 92.933 | 92.427 | 92.663 | 92.518 | 92.825 | 88.098 |
| 92.634 | 93.174 | 93.182 | 93.188 | 92.933 | 100.000 | 91.926 | 92.058 | 92.376 | 95.560 | 88.716 |
| 93.633 | 93.757 | 91.881 | 91.897 | 92.427 | 91.926 | 100.000 | 92.866 | 93.295 | 91.544 | 87.667 |
| 93.231 | 93.119 | 93.366 | 93.370 | 92.663 | 92.058 | 92.866 | 100.000 | 99.735 | 91.774 | 86.845 |
| 93.234 | 93.312 | 93.505 | 93.508 | 92.518 | 92.376 | 93.295 | 99.735 | 100.000 | 91.630 | 87.674 |
| 91.826 | 92.327 | 92.867 | 92.879 | 92.825 | 95.560 | 91.544 | 91.774 | 91.630 | 100.000 | 90.218 |
| 88.233 | 87.877 | 88.129 | 88.137 | 88.098 | 88.716 | 87.667 | 86.845 | 87.674 | 90.218 | 100.000 |
| | | | | | | | | | | |
| colon-14 | 1.2-3b | KP2-8c | | | | | | | | |
| 86.71193 | 85.66118 | 85.68349 | | | | | | | | |
| 89.18009 | 85.62027 | 85.64013 | | | | | | | | |
| 89.15457 | 85.48491 | 85.50717 | | | | | | | | |
| 91.54822 | 93.46059 | 93.46846 | | | | | | | | |
| 93.07423 | 91.31087 | 91.34391 | | | | | | | | |
| 92.63276 | 92.07773 | 91.82003 | | | | | | | | |
| 92.63021 | 92.09582 | 91.81746 | | | | | | | | |
| 92.53324 | 91.97748 | 91.71993 | | | | | | | | |
| 100 | 97.71098 | 97.82326 | | | | | | | | |
| 97.71098 | 100 | 99.85627 | | | | | | | | |
| 97.82326 | 99.85627 | 100 | | | | | | | | |
| | | | | | | | | | | |
| MCoc5c | MCoc7c | | | | | | | | | |
| 85.828 | 86.267 | | | | | | | | | |
| 85.830 | 86.270 | | | | | | | | | |
| 86.992 | 87.296 | | | | | | | | | |
| 87.002 | 87.342 | | | | | | | | | |
| 86.768 | 87.108 | | | | | | | | | |
| 94.994 | 94.701 | | | | | | | | | |
| 96.040 | 94.668 | | | | | | | | | |
| 98.882 | 98.582 | | | | | | | | | |
| 100.000 | 98.303 | | | | | | | | | |
| 98.324 | 100.000 | | | | | | | | | |

FROM FIG.2

*FIG. 2 (CONT.)*

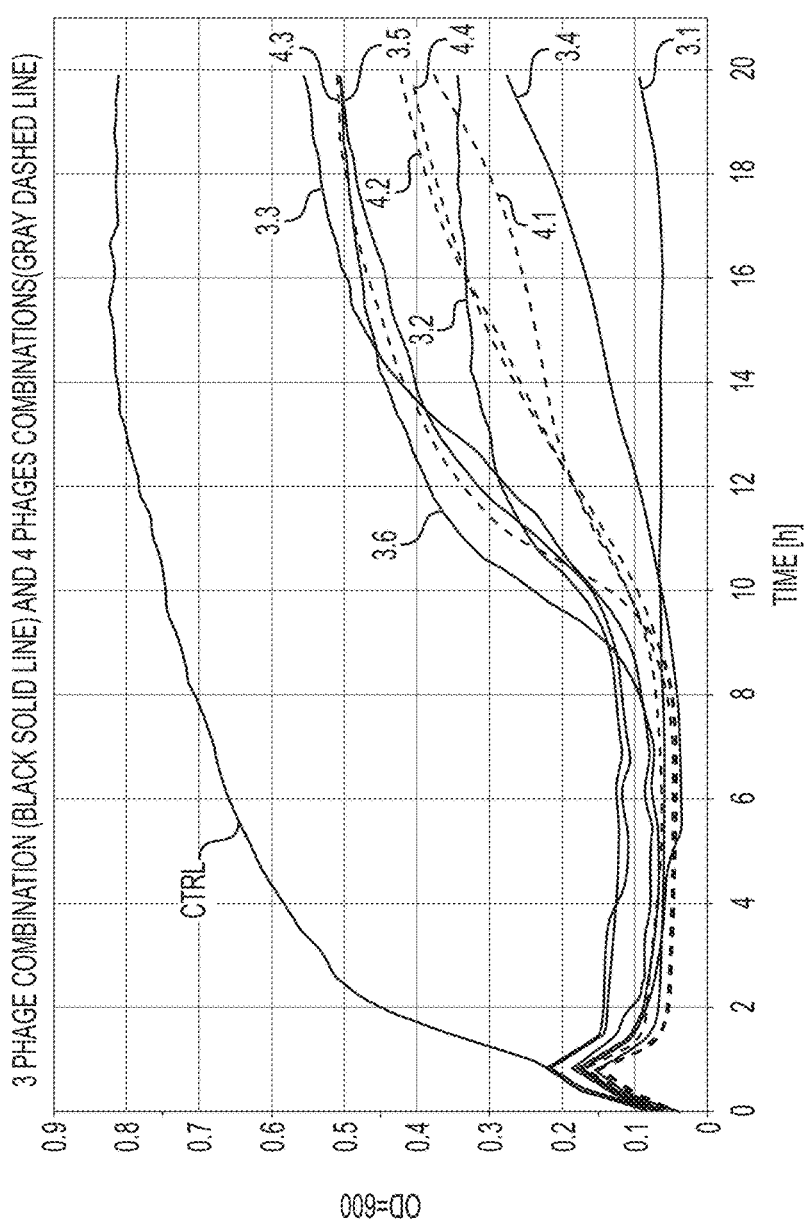
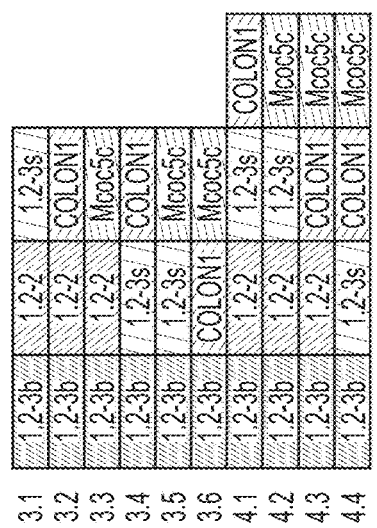
FIG. 10

| MUTANT | MUTATIONS | | colon-1 | KP2-5-1 | MCoc5 | Mcoc3 | 1.2-3b | Kp2-8C | KP2-7-1c | 8M-1 | 1.2-2 | PKP-55 | Colon-11 | 1.2-3s | 8M-7 | 8M-8 |
|---|---|---|---|---|---|---|---|---|---|---|---|---|---|---|---|---|
| colon1_1 11_S83 | LPS (rfaQ) | | R | R | R | R | S | S | S | S | S | S | R | R | R | R |
| colon1_1 38_S110 | LPS (greA) | | R | R | R | R | S | S | S | S | S | R | R | S | R | R |
| Mcoc_5C_1 | LPS (rfaG) | | S | S | R | R | S | S | S | S | S | S | S | S | R | R |
| Mcoc_5C_4 | LPS (wcaJ OR wbaP) | | S | S | R | R | S | S | S | S | S | S | S | S | R | R |
| Mcoc_5C_7 | LPS (wcaJ OR wbaP) | | S | S | S | S | R | R | S | S | S | S | S | S | R | R |
| 1.2-3b_2 27_S92 | LPS (mfpsA) | | S | S | S | S | R | R | R | S | S | S | S | R | S | S |
| 1.2-3b_8 29_S101 | LPS (wecA) | | S | S | R | S | R | R | R | R | R | R | S | R | S | S |
| 1.2-3b_7 12_S84 | IRON UPTAKE (fhuA) | LPS (wecA) | R | R | R | R | R | R | R | R | R | R | R | R | S | S |
| 8M1_1 | IRON UPTAKE (fepA) | | R | R | R | R | R | R | R | R | R | R | R | R | S | S |
| 8M1_6 | Cobalamin uptake (tonB) | maltose and maltodextrin transport (LamB) | R | R | R | R | R | R | R | R | R | R | R | R | S | S |
| 1.2-2_2 20_S92 | LPS (HBAD) | | R | R | S | S | R | R | R | R | R | R | R | R | R | R |
| 1.2-2_2 21 OR 22 | LPS (HBAD) | | S | S | R | R | S | S | S | S | R | S | R | S | S | S |
| 1.2-3S_6 14_S86 | LPS (lpxM) | | R | R | R | R | S | S | S | S | R | R | R | R | R | R |
| 1.2-3s_24 or 25 OR 26 | wbaP OR IRON (fhuA) | | S | S | S | R | S | S | S | S | S | R | S | R | R | R |

*FIG. 14*

INFECTIVITY AT 1×10⁹ PFU/mL

| ISOLATED ON | | KP1 (ATCC BAA-2552) | KP2 | KP4 (ATCC 23356) | KP5 (ATCC 13882) | KP6 (ATCC BAA-1705) | KP7 (ATCC 700603) | KP8 (ATCC 700721) |
|---|---|---|---|---|---|---|---|---|
| KP2-5 | KP2 | R | S | R | R | R | R | R |
| KP2-5-1 | KP2 | R | S | S | R | R | R | R |
| KP2-14 | KP2 | R | S | R | R | R | R | R |
| KP2-15-1 | KP2 | R | S | R | R | R | R | R |
| KP2-15-2-1 | KP2 | R | S | R | R | R | R | R |
| KP2-16-1 | KP2 | R | S | R | R | R | R | R |
| 23356-B1 | KP4 | R | R | S | NT | NT | NT | NT |

INFECTIVITY AT 1×10⁶ PFU/mL

| ISOLATED ON | | KP1 (ATCC BAA-2552) | KP2 | KP4 (ATCC 23356) |
|---|---|---|---|---|
| KP2-5 | KP2 | R | S | R |
| KP2-5-1 | KP2 | R | S | R |
| KP2-14 | KP2 | R | S | R |
| KP2-15-1 | KP2 | R | S | R |
| KP2-15-2-1 | KP2 | R | S | R |
| KP2-16-1 | KP2 | R | S | R |
| 23356-B1 | KP4 | R | R | S |

*FIG. 15*

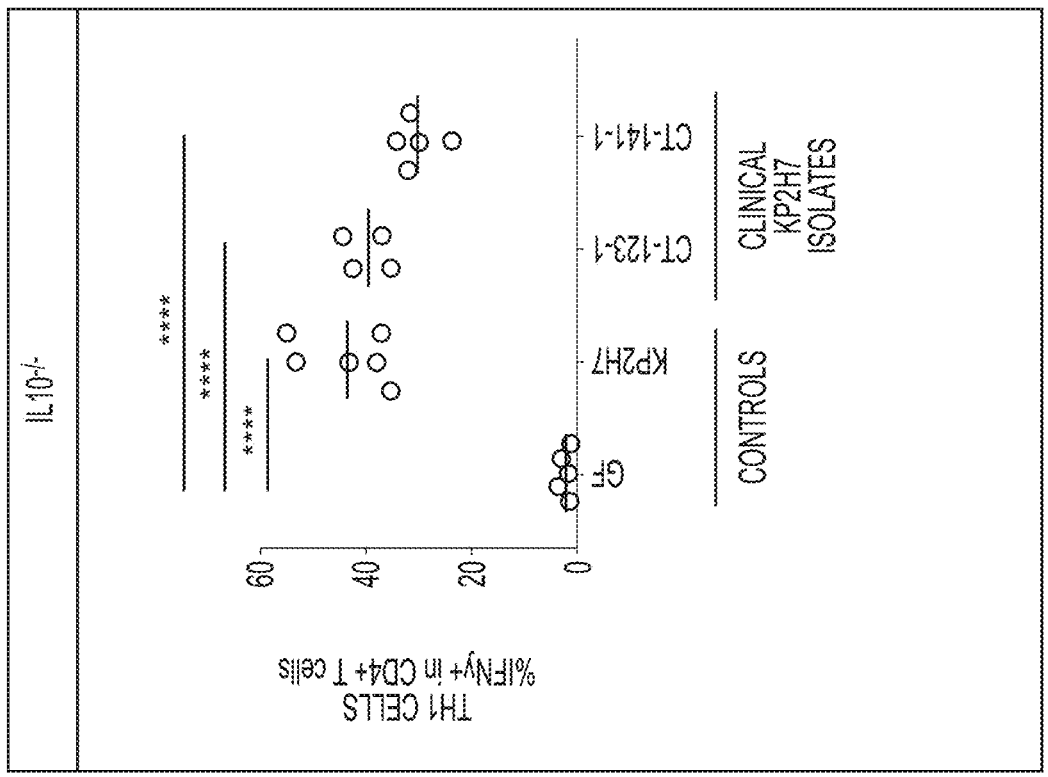
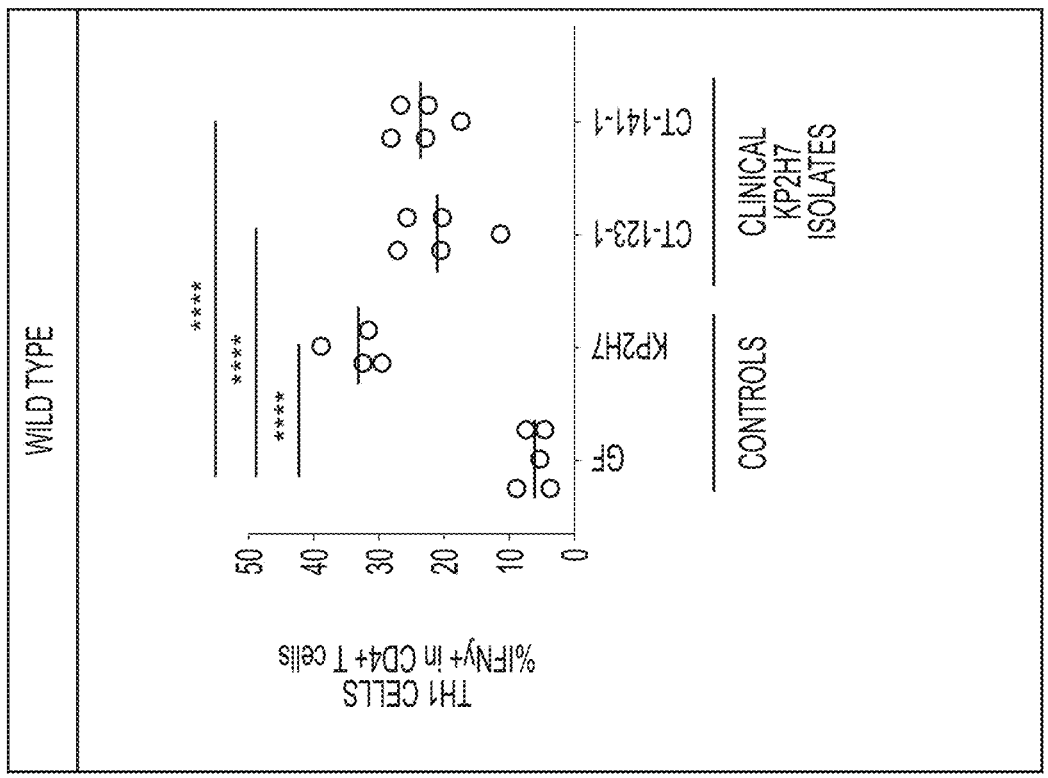
FIG. 17

BACTERIOPHAGE FOR MODULATING INFLAMMATORY BOWEL DISEASE

RELATED APPLICATIONS

This application is a National Phase of PCT Patent Application No. PCT/IB2020/000182 having International filing date of Mar. 6, 2020, which claims the benefit of priority under 35 USC § 119(e) of U.S. Provisional Application No. 62/815,265, filed on Mar. 7, 2019. The contents of the above applications are all incorporated by reference as if fully set forth herein in their entirety.

FIELD AND BACKGROUND OF THE INVENTION

Sequence Listing Statement

The ASCII file, entitled 88041SequenceListing.txt, created on Sep. 7, 2021 comprising 18,004,250 bytes, submitted concurrently with the filing of this application is incorporated herein by reference. The sequence listing submitted herewith is identical to the sequence listing forming part of the international application.

This disclosure relates to bacteriophage compositions and therapeutic uses thereof. In a particular aspect, the disclosure relates to lytic bacteriophages that are capable of lysing certain *Klebsiella* bacterial strains. In certain embodiments, the lytic bacteriophages are capable of lysing *Klebsiella* bacterial strains that are associated with inflammatory bowel disease (IBD) (e.g., ulcerative colitis, Crohn's disease), thereby modulating the disease.

Gut microbiota dysbiosis is associated with the pathogenesis of IBD (Said et al., 2014). Increased stimulation from the gut microbiota can result in inflammation and alter a patient's immune response. In humans, the oral microbiota comprises over 700 species or phylotypes of bacteria (Said et al., 2014). Ingested oral bacteria do not typically colonize the healthy intestine (Chen et al., 2016; Bik et al., 2010; U.S. Provisional Application No. 62/415,759, TH1 Cell Stimulatory Bacteria Colonizing in Human Oral Cavity). However, bacteria of oral origin may be increased in the gut microbiota of patients with IBD (Gevers et al., 2014; Atarashi et al., 2017). Oral microbiota dysbiosis is observed in patients with IBD and could contribute to disease etiology (Said et al., 2014).

IBDs, such as Crohn's disease (CD) and ulcerative colitis (UC), can cause diarrhea, malabsorption of nutrients, malnutrition, anemia, and weight loss. Severe intestinal inflammation can extend beyond the mucosa of the intestines and cause ulceration, bleeding, toxic megacolon, strictures, and fistulas. In addition, chronic inflammation is associated with colon cancer. Extraintestinal complications include, but are not limited to, arthritis, skin rashes, liver disease, and eye disorders such as episcleritis and uveitis.

According to the Crohn's & Colitis Foundation of America, "there is no single ideal therapy" for IBD. Dietary restriction alone has not been shown to ameliorate IBD. For many patients, surgical intervention is necessary. Even with the currently available IBD treatments, many patients experience IBD flares between periods of remission. Thus, there is significant unmet need for effective, reliable, and long-term treatment and/or prevention of IBD.

The disclosure provides bacteriophage compositions and therapeutic uses thereof. In specific embodiments, the disclosure provides lytic bacteriophages that are capable of lysing one or more *Klebsiella* species, strains, or sub strains, such as *Klebsiella pneumoniae* (e.g., *Klebsiella pneumoniae* 2H7 strain, "KP2" or "KP2H7" herein) that are associated with IBD. The disclosure provides methods for modulating IBD. The disclosure also provides methods for selecting patients to be treated with the methods provided herein.

BRIEF DESCRIPTION OF THE SEVERAL VIEWS OF THE DRAWINGS

FIG. 1 shows the results of the host range analysis of bacteriophage isolated against wild-type KP2 bacteria, clinical KP2 variants and mutant KP2 bacteria resistant to infection by particular KP2 bacteriophage. "S" indicates susceptibility (10 plaques or more to full clearing) and "R" indicates resistance (less than 10 plaques)

FIG. 2 shows percent homology between the bacteriophage genomes in each taxonomic group. Percent homology between the phage genomes is determined by combining all non-overlapping BLASTN alignment segments (BLAST HSPs), summing the values of their "Number of identical matches" and dividing this sum by the length of the query sequence. In some embodiments, this results in a non-symmetrical matrix.

FIG. 10 shows in vitro infection of KP2 with bacteriophage compositions containing 3 phage (black solid line) or 4 phage (gray dashed line) and no phage control (gray solid line) in liquid, as further described in Example 14.

FIG. 14 shows that bacterial mutants which developed resistance (R) to certain phage are sensitive to at least two other phage (S). Gray shaded boxes indicate resistance to the particular phage against which the bacterial mutant was raised. For example, Colon1_1 11_S83 and Colon1_1 38_S110 are resistant to and raised against colon1. Genomic modifications which affect phage infection (i.e., modifications found in a phage-resistant mutant bacteria that arose in a culture containing a specific phage capable of infecting a specific bacteria) are shown in Table 2.

FIG. 15 shows host range analysis of six phage isolated against KP2 on other *Klebsiella pneumonia* strains as indicated and activity of commercial phage on KP2 and other *Klebsiella pneumonia* strains. Activity was measured at two phage titers—$1 \times 10^9$ PFU/mL and $1 \times 10^6$ PFU/mL. S— sensitive, R— resistant, NT—not tested, PFU—plaque forming units. FIG. 15 shows that the commercial phage isolated against KP4 does not recognize KP2 and phage isolated against KP2 do not recognize commercial *Klebsiella pneumonia* strains except for recognition of KP4 by KP2-5-1, at high titer ($10^9$ PFU/mL).

FIGS. 16a-c, 16f: CT-141-1, FIG. 16d: CT-123-1, FIG. 16e, 16g-j: KP2.

FIG. 17 presents TH1 induction by KP2H7 clinical isolates. Analysis of TH1 (CD4+IFNγ+ T cells) in colonic lamina propria of mono-associated ex-GF (germ free) wild type or IL10−/− mice 3 and 2 weeks post-colonization, respectively. Clinical KP2H7 isolates tested induced a higher percentage of TH1 cells in the colonic lamina propria of monocolonized mice compared to the non-colonized animals. The designation "****" between two groups represents p-value less than 0.0001 (Holm-Sidak).

Figure 3:
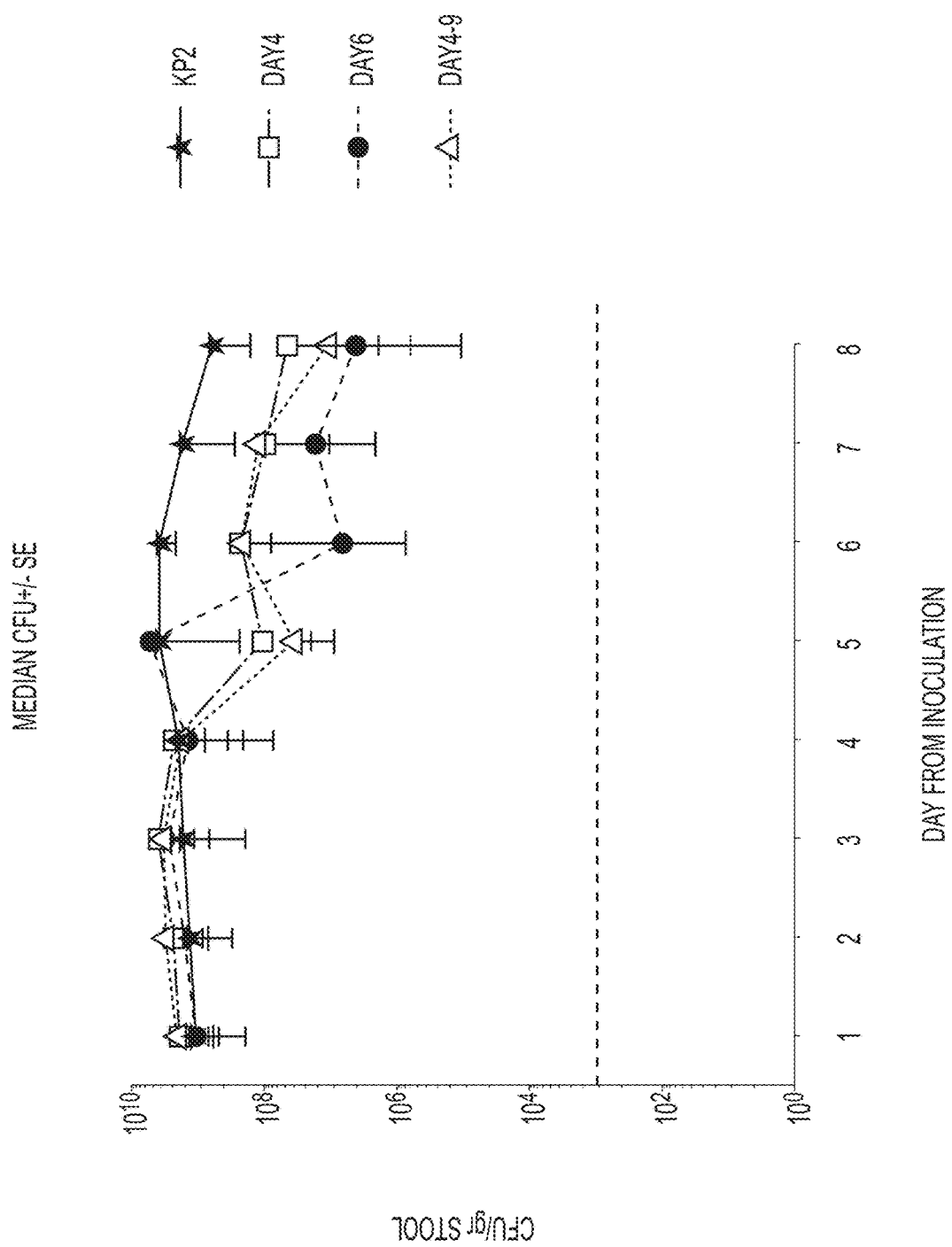
FIG. 3 shows KP2 CFU in stool for four groups of mice previously colonized by KP2 and then treated in one of following ways: 1) vehicle control administered daily starting on day 4 post KP2 administration (KP2); 2) a single dose of phage cocktail administered on day 4 post KP2 administration (Day 4); 3) daily phage cocktail doses administered starting on day 4 post KP2 administration (Day 4-6); 4) a single dose of phage cocktail administered on day 6 post KP2 administration (Day 6). The phage cocktail was comprised of the phages 1.2-2, 1.2-3s, and 1.2-3b. The dashed line represents the limit of detection ($10^3$ CFU/g stool).

Sequences of Exemplary bacteriophage of the disclosure and Exemplary bacteria against which such phage were tested are disclosed in Table 1. The KP2 genome has been sequenced and is known in the art, see, e.g., GenBank BDQR01000001.1, GenBank GCA_002260905.1, BioSample: SAMD00083910, BioProject PRJDB5883, and Atarashi et al., Ectopic colonization of oral bacteria in the intestine drives TH1 cell induction and inflammation, Science (2017). In some embodiments, a genomic sequence, e.g., a KP2 genomic sequence, may encompass minor sequencing differences, e.g., less than 0.5%, less than 1%, less than 1.5%, less than 2%, less than 2.5%, or less than 3% as compared to another genomic sequence of the same bacterium, and the sequencing differences should not result in functional differences, e.g., bacteriophage infectivity, of the bacterium.

Where more than one SEQ ID NO is associated with a bacteriophage named in Table 1, the bacteriophage may be represented by either sequence. For example, SEQ ID NO: 1 may represent Bacteriophage 1.2-4br and SEQ ID NO: 132 may represent Bacteriophage 1.2-4br.

TABLE 1

Brief Description of the Sequences

| SEQ ID NO: | Sequence Name |
|---|---|
| 1, 132 | 1.2-4br Bacteriophage Sequence |
| 2, 133 | 1.2-4s Bacteriophage Sequence |
| 3, 168 | colon-11 Bacteriophage Sequence |
| 4, 167 | colon1 Bacteriophage Sequence |
| 5, 128 | colon-6 Bacteriophage Sequence |
| 127 | PKP-55 Bacteriophage Sequence |
| 129 | 1.2-2 Bacteriophage Sequence |
| 130 | 1.2-3b Bacteriophage Sequence |
| 131 | 1.2-3s Bacteriophage Sequence |
| 134 | 8M-1 Bacteriophage Sequence |
| 135 | 8M-7 Bacteriophage Sequence |
| 136 | 8M-8 Bacteriophage Sequence |
| 140 | KP2-5-1 Bacteriophage Sequence |
| 160 | MCoc5c Bacteriophage Sequence |
| 6, 169 | colon-14 Bacteriophage Sequence |
| 7, 137 | colon-14-15 Bacteriophage Sequence |
| 8, 138 | colon-36 Bacteriophage Sequence |
| 21, 147 | KP2-14 Bacteriophage Sequence |
| 22, 170 | KP2-15-1 Bacteriophage Sequence |
| 23, 148 | KP2-15-2-1 Bacteriophage Sequence |
| 24, 149 | KP2-16-1 Bacteriophage Sequence |

TABLE 1-continued

Brief Description of the Sequences

| SEQ ID NO: | Sequence Name |
| --- | --- |
| 25, 145 | KP2-8c Bacteriophage Sequence |
| 26, 150 | KP2-5 Bacteriophage Sequence |
| 27, 142 | KP2-7-1c Bacteriophage Sequence |
| 28, 144 | KP2-8a Bacteriophage Sequence |
| 29, 143 | KP2-7c Bacteriophage Sequence |
| 31, 139 | KP2-4a Bacteriophage Sequence |
| 33, 152 | M16-4a Bacteriophage Sequence |
| 34, 141 | KP2-5a Bacteriophage Sequence |
| 35, 146 | KP2-9a Bacteriophage Sequence |
| 36, 157 | M16-9a Bacteriophage Sequence |
| 37, 151 | M16-3-2c Bacteriophage Sequence |
| 38, 153 | M16-5c Bacteriophage Sequence |
| 39, 154 | M16-6c Bacteriophage Sequence |
| 40, 155 | M16-7a Bacteriophage Sequence |
| 44, 166 | Mcoc3c Bacteriophage Sequence |
| 45, 162 | Mcoc7c Bacteriophage Sequence |
| 46, 161 | MCoc6c Bacteriophage Sequence |
| 47, 159 | MCoc4c Bacteriophage Sequence |
| 48, 156 | M16-9-1c Bacteriophage Sequence |
| 49, 164 | MCoc9-1c Bacteriophage Sequence |
| 50, 165 | MCoc9-2c Bacteriophage Sequence |
| 51, 158 | MCoc15c Bacteriophage Sequence |
| 52, 163 | MCoc8a Bacteriophage Sequence |
| 53 | KP2-Mcoc1 Bacteria Sequence |
| 54 | KP2-Mcoc1 Bacteria Sequence |
| 55 | KP2-Mcoc1 Bacteria Sequence |
| 56 | KP2-Mcoc1 Bacteria Sequence |
| 57 | KP2-Mcoc1 Bacteria Sequence |
| 58 | KP2-Mcoc1 Bacteria Sequence |
| 82 | KP2-Mcoc1 Bacteria Sequence |
| 59 | KP2-Mcoc1 Bacteria Sequence |
| 60 | KP2-Mcoc1 Bacteria Sequence |
| 61 | KP2-Mcoc1 Bacteria Sequence |
| 62 | KP2-Mcoc1 Bacteria Sequence |
| 63 | KP2-Mcoc1 Bacteria Sequence |
| 64 | KP2-Mcoc1 Bacteria Sequence |
| 65 | KP2-Mcoc1 Bacteria Sequence |
| 66 | KP2-Mcoc1 Bacteria Sequence |
| 67 | KP2-Mcoc1 Bacteria Sequence |
| 68 | KP2-Mcoc1 Bacteria Sequence |
| 69 | KP2-Mcoc1 Bacteria Sequence |
| 70 | KP2-Mcoc1 Bacteria Sequence |
| 71 | KP2-Mcoc1 Bacteria Sequence |
| 72 | KP2-Mcoc1 Bacteria Sequence |
| 73 | KP2-Mcoc1 Bacteria Sequence |
| 74 | KP2-Mcoc1 Bacteria Sequence |
| 75 | KP2-Mcoc1 Bacteria Sequence |
| 76 | KP2-Mcoc1 Bacteria Sequence |
| 77 | KP2-Mcoc1 Bacteria Sequence |
| 78 | KP2-Mcoc1 Bacteria Sequence |
| 79 | KP2-Mcoc1 Bacteria Sequence |
| 80 | KP2-Mcoc1 Bacteria Sequence |
| 81 | KP2-Mcoc1 Bacteria Sequence |
| 83 | KP2-Mcoc1 Bacteria Sequence |
| 84 | KP2-Mcoc1 Bacteria Sequence |
| 85 | KP2-Mcoc1 Bacteria Sequence |
| 86 | KP2-Mcoc1 Bacteria Sequence |
| 87 | KP2-Mcoc1 Bacteria Sequence |
| 88 | KP2-Mcoc1 Bacteria Sequence |
| 89 | KP2-Mcoc1 Bacteria Sequence |
| 90 | KP2-Mcoc1 Bacteria Sequence |
| 91 | KP2-Mcoc1 Bacteria Sequence |
| 92 | KP2-Mcoc1 Bacteria Sequence |
| 93 | KP2-Mcoc1 Bacteria Sequence |
| 94 | KP2-Mcoc1 Bacteria Sequence |
| 95 | KP2-Mcoc1 Bacteria Sequence |
| 96 | KP2-Mcoc1 Bacteria Sequence |
| 97 | KP2-Mcoc1 Bacteria Sequence |
| 98 | KP2-Mcoc1 Bacteria Sequence |
| 99 | KP2-Mcoc1 Bacteria Sequence |
| 100 | KP2-Mcoc1 Bacteria Sequence |

TABLE 1-continued

Brief Description of the Sequences

| SEQ ID NO: | Sequence Name |
|---|---|
| 101 | KP2-Mcoc1 Bacteria Sequence |
| 102 | KP2-Mcoc1 Bacteria Sequence |
| 103 | KP2-Mcoc1 Bacteria Sequence |
| 104 | KP2-Mcoc1 Bacteria Sequence |
| 105 | KP2-Mcoc1 Bacteria Sequence |
| 106 | KP2-Mcoc1 Bacteria Sequence |
| 107 | KP2-Mcoc1 Bacteria Sequence |
| 108 | KP2-Mcoc1 Bacteria Sequence |
| 109 | KP2-Mcoc1 Bacteria Sequence |
| 110 | KP2-Mcoc1 Bacteria Sequence |
| 111 | KP2-Mcoc1 Bacteria Sequence |
| 112 | KP2-Mcoc1 Bacteria Sequence |
| 113 | KP2-Mcoc1 Bacteria Sequence |
| 114 | KP2-Mcoc1 Bacteria Sequence |
| 115 | KP2-Mcoc1 Bacteria Sequence |
| 116 | KP2-Mcoc1 Bacteria Sequence |
| 117 | KP2-Mcoc1 Bacteria Sequence |
| 118 | KP2-Mcoc1 Bacteria Sequence |
| 119 | KP2-Mcoc1 Bacteria Sequence |
| 120 | KP2-Mcoc1 Bacteria Sequence |
| 121 | KP2-Mcoc1 Bacteria Sequence |
| 122 | KP2-Mcoc1 Bacteria Sequence |
| 123 | KP2-Mcoc1 Bacteria Sequence |
| 124 | KP2-Mcoc1 Bacteria Sequence |
| 125 | KP2-Mcoc1 Bacteria Sequence |
| 126 | KP2-Mcoc1 Bacteria Sequence |

DESCRIPTION OF SPECIFIC EMBODIMENTS OF THE INVENTION

The disclosure relates to bacteriophage, pharmaceutical compositions thereof, methods of modulating IBD (Jostins et al., 2012), and methods of selecting patients that are responsive to treatment by the methods set forth herein. In some embodiments, the bacteriophage described herein is capable of lysing *Klebsiella* bacterial that are or have been associated with IBD. IBD patients demonstrate elevated systemic antibodies against certain bacterial capsular types (e.g., K2, K17, K26, K36, K50, and K21 found in KP2) compared to controls and other pathologic conditions. These findings suggest the involvement of *Klebsiella* in IBD, but do not explain how *Klebsiella* may be actively involved in the pathogenesis of the disease and do not provide strain-specific resolution as different strains share similar capsular types. Strains of *Klebsiella* isolated from the salivary microbiota "are strong inducers of T helper 1 (TH1) cells when they colonize in the gut" and "elicit a severe gut inflammation in the context of a genetically susceptible host." See Atarashi et al., 2017.

Definitions

In order that the disclosure may be more readily understood, certain terms are first defined. These definitions should be read in light of the remainder of the disclosure and as understood by a person of ordinary skill in the art. Unless defined otherwise, all technical and scientific terms used herein have the same meaning as commonly understood by a person of ordinary skill in the art. Additional definitions are set forth throughout the detailed description.

As used herein, the terms "treat" and "modulate" and their cognates refer to an amelioration of IBD or at least one discernible symptom thereof. In some embodiments, "treat" and "modulate" and their cognates refer to an amelioration of at least one measurable physical parameter, not necessarily discernible by the patient. In some embodiments, "treat" and "modulate" and their cognates refer to inhibiting or reducing or slowing the progression of IBD, either physically (e.g., stabilization of a discernible symptom), physiologically (e.g., stabilization of a physical parameter), or both, relative to an untreated control. In certain embodiments, "treat" and "modulate" and their cognates refer to slowing the progression or reversing the progression of IBD relative to an untreated control. As used herein, "prevent" and its cognates refer to delaying the onset or reducing the risk of acquiring IBD or a symptom associated with IBD relative to an untreated control.

In certain embodiments, the bacteriophage described herein is administered to ameliorate an IBD in a subject and results in one or more symptoms or physical parameters of the condition or disorder to improve by at least about 10%, 20%, 30%, 40%, 50%, 60%, 70%, 80%, 90%, 95%, or more as compared to levels in an untreated or control subject. In some embodiments, the improvement is measured by comparing the symptom or physical parameter in a subject before and after administration of the bacteriophage. In some embodiments, the measurable physical parameter is a reduction in bacterial CFU in the stool.

The measurable physical parameter may be any suitable clinical parameter known in the art, e.g., for Crohn's disease (Sandborn et al., 2013; Best et al., 1976; Warrel—Oxford Textbook of Medicine, 5th edition) or for ulcerative colitis (Tursi et al., 2010; Warrel—Oxford Textbook of Medicine, 5th edition). Crohn's disease parameters include but are not limited to assessment of clinical remission using Crohn's Disease Activity Index (CDAI) (CDAI score of ≤150 points) and CDAI-100 response (≥100-point decrease in the CDAI score from the baseline); inflammation reduction as measured by decrease in serum levels of C-reactive protein, differential blood count and serum albumin levels; reduced levels of fecal calprotectin and improvement in the appearance of the mucosal layer in terminal ileum and rectum as evaluated by microscopic examination of the biopsies collected during endoscopic procedures (e.g., reduction in neutrophil, macrophage and other immune cell infiltration, granuloma size and number, reduction in the number and size of ulcers, edematous mucosa). In addition the improvement of the disease may be evaluated based on the assessment of the clinical symptoms including diarrhea, abdominal pain, weight loss, fever, vomiting, colic, rectal bleeding, anemia, extraintestinal manifestations (hypersensitivity rash to sulphasalazine, erythema nodosum, pyoderma gangrenosum, oral aphthous ulcers, sore tongue, angular stomatitis, episcleritis or an anterior uveitis, arthritis, acute arthropathy, low back pain, sacroiliitis, ankylosing spondylitis, liver diseases: minor elevations of alkaline phosphatase or transaminases, primary sclerosing cholangitis, chronic liver disease ranging from an autoimmune hepatitis to the classic picture of concentric periductular fibrosis with obliteration of bile ducts, pericarditis with or without an effusion, autoimmune hemolytic anaemia, amyloid, rapidly progressing bronchiectasis).

Ulcerative colitis disease parameters include but not limited to improvement in the ulcerative colitis disease activity index (UCDAI) (UCDAI decrease of 50% or more from the baseline), activity of relapsing UC; remission, considered as UCDAI ≤2; improvement in hemoglobin levels, serum albumin levels, decrease in C-reactive protein levels; improvement in neutrophil leukocytosis (blood differential count); improvement in endoscopic scores (reduction in the edematous mucosa area, reduction in neutrophil, macrophage and other immune cell infiltration, reduction in the number and size of ulcers, edematous mucosa; improvement in the clinical symptoms: rectal bleeding, fever, stool frequency, diarrhea, the passage of mucus, abdominal pain, constipation, anorexia, nausea, weight loss, malaise, lassitude, symptoms of chronic iron deficiency, minor perianal disease, such as a fissure, extraintestinal manifestations described above, and additionally oral candidiasis, finger clubbing.

Those in need of treatment may include individuals already having IBD, as well as those at risk of having, or who may ultimately acquire the disease. The need for treatment is assessed, e.g., by the presence of one or more risk factors associated with the development of IBD, the presence or progression of IBD, or likely receptiveness to treatment of a subject having IBD. For example, "treating" IBD may encompass reducing or eliminating associated symptoms, and does not necessarily encompass the elimination of the underlying disease etiology, e.g., a genetic instability locus.

In some embodiments, an individual with IBD is in remission and/or presently asymptomatic, and the bacteriophage described herein may be administered during the remission period to reduce the potential for a flare-up. In some embodiments, the individual in remission and/or presently asymptomatic for IBD is undergoing treatment, e.g., antibiotics and/or steroids, and the bacteriophage described herein may be co-administered with such treatment to reduce the potential for a flare-up.

*Klebsiella* is a genus of bacteria belonging to the Enterobacteriaceae family. *Klebsiella* are gram-negative, nonmotile, and rod-shaped. In some embodiments, the species of *Klebsiella* may be associated with human disease, e.g., *Klebsiella pneumoniae*. As used herein, *Klebsiella* includes bacteria that are currently classified, were previously classified, or will be reclassified as *Klebsiella* bacteria. In some embodiments, *Klebsiella* refers to *Klebsiella pneumoniae*. In some embodiments, *Klebsiella* refers to naturally occurring *Klebsiella*. In some embodiments, *Klebsiella* refers to a naturally occurring, variant or mutant *Klebsiella* (e.g., antibiotic resistant, phage resistant, nosocomial). In some embodiments, the variant or mutant *Klebsiella* is resistant to at least 1, at least 2, at least 3, at least 4, or at least 5 antibiotics. In some embodiments, a mutant bacterial strain may arise in the presence of a bacteriophage and become resistant to said bacteriophage.

As used herein, a "strain" of bacteria refers to a genetic variant or subtype of bacteria. In some embodiments, a "strain" of bacteria comprises descendants from a single isolation in a pure culture of said bacteria. As used herein, a "strain" of bacteria may refer to one or more genetic variants or subtypes of said bacteria. For example, as used herein, a "strain" of *Klebsiella pneumoniae* may refer to one or more genetic variants or subtypes of *Klebsiella pneumoniae*, including but not limited to KP1 (ATCC BAA-2552; also referred to as *Klebsiella* variicola), KP2 (*Klebsiella pneumoniae* strain 2H7 described herein), KP4 (ATCC 23356), KP5 (ATCC 13882), KP6 (ATCC BAA-1705), KP7 (ATCC 700603), and KP8 (ATCC 700721). Similarly, as used herein, a bacteriophage that is capable of lysing a "strain" of *Klebsiella pneumoniae* refers to a bacteriophage that is capable of lysing one or more genetic variants or subtypes of *Klebsiella pneumoniae*, including but not limited to KP1, KP2, KP4, KP5, KP6, KP7, and KP8. In some embodiments, a bacteriophage that is capable of lysing a "strain" of *Klebsiella pneumoniae* refers to a bacteriophage that is capable of lysing one or more genetic variants or subtypes of *Klebsiella pneumoniae* KP2, KP4, KP5, KP6, KP7, and KP8. In some embodiments, the KP2 bacteriophage described herein is capable of lysing a KP2 strain of *Klebsiella pneumoniae*.

The term "KP2" when used in reference to a bacterium and without a further qualifier (e.g., "mutant", "variant", "wild-type", etc.) is used herein, in the alternative, to refer to either a wild-type strain of *Klebsiella pneumoniae* that has been designated as "KP2" or "KP2H7", or to a bacterium that may be either such wild-type strain or a mutant thereof. It should be readily apparent to one of ordinary skill in the art, which of the two alternate meanings is intended by the context in which the term is used. If the context does not unambiguously inform one of ordinary skill in the art which definition is intended, then the term "KP2" shall be interpreted to mean a bacterium that may be either such wild-type strain or a mutant thereof.

The term "a strain of KP2 bacterium" as used herein refers to a wild-type strain of *Klebsiella pneumoniae* that has been designated as "KP2" or "KP2H7".

In some embodiments, as used herein, a "mutant" bacterium refers to a bacterium that comprises greater than about 85%, greater than about 90%, greater than about 95%, greater than about 97%, or greater than about 99% homology to a corresponding wild-type bacterial strain. For example, a mutant KP2 bacterium comprises greater than about 85%, greater than about 90%, greater than about 95%, greater than about 97%, or greater than about 99% homology to a wild-type KP2 bacterium. The terms "mutant KP2 bacterium" and "KP2 mutant" are used interchangeably and both terms include such bacterium isolated from human or animal patients ("clinical isolates" or "clinical variants"), such bacterium isolated from the environment ("environmental isolates"), and such bacterium produced in a laboratory setting (e.g., though genetic engineering or through selection pressure). The terms "mutant KP2 bacterium" and "KP2 mutant" also encompass "KP2-variants" (as defined below).

In some embodiments, a KP2 bacterium, e.g., a strain of KP2 bacterium, and/or a mutant KP2 bacterium, e.g., an environmental and/or clinical isolate as described herein, is positive for a genomic region that may be identified by PCR using the following primers: 5'AGCACTAGCGGCTGTGGTAT3' (SEQ ID NO: 287) and 5'ACTTACTCGGGCCCTTGATT3' (SEQ ID NO: 288). See, e.g., Atarashi et al., 2017.

In some embodiments, the mutant KP2 bacterium, e.g., an environmental and/or clinical isolate identified using said primers, comprises greater than about 95%, greater than about 96%, greater than about 97%, greater than about 98%, or greater than about 99% homology to the wild-type KP2 bacterium, e.g., % homology as calculated by ANI (Average Nucleotide Identity). See, e.g., Han et al., ANItools web: a web tool for fast genome comparison within multiple bacterial strains (2016). In some embodiments, the mutant KP2 bacterium, e.g., an environmental and/or clinical isolate identified using said primers, comprises greater than about 95%, greater than about 96%, greater than about 97%, greater than about 98%, or greater than about 99% homology to the coding regions of the wild-type KP2 bacterium. In some embodiments, a mutant KP2 bacterium identified by said primers and is at least about 99% homologous to the wild-type KP2 bacterium is referred to as "KP2-variant" herein. In some embodiments, the mutant and/or KP2-variant bacterium is capable of being lysed by at least one of the KP2 bacteriophage disclosed herein. In some embodiments, a KP2 bacterium, e.g., a strain of KP2 bacterium, and/or a mutant KP2 bacterium, e.g., an environmental and/or clinical isolate as described herein comprises a genome with greater than about 95%, greater than about 96%, greater than about 97%, greater than about 98%, or greater than about 99% homology to reference sequences as further detailed in Example 1. In some embodiments, a KP2 bacterium, e.g., a strain of KP2 bacterium, and/or a mutant KP2 bacterium, e.g., an environmental and/or clinical isolate as described herein comprises a multi-locus sequence type (MLST) of type 323.

As used herein, "bacteriophage" and "phage" are used interchangeably and refer to an isolated virus that is capable of infecting a bacterium. In some embodiments, the phage comprises a DNA or an RNA genome. A phage may be isolated from a natural or human-made environment. In some embodiments, the phage is selected from Myoviridae, Podoviridae, and Siphoviridae. As used herein, a "KP bacteriophage" is intended to refer to a bacteriophage that is capable of lysing a *Klebsiella pneumoniae* bacterium. For example, a "KP2 bacteriophage" refers to a bacteriophage that is capable of lysing a *Klebsiella pneumoniae* strain KP2 bacterium, including wild-type and, in some instances, one or more mutant KP2 bacterium or KP2 variant.

It is known that different isolates of a given bacteriophage may vary at the nucleic acid sequence level. In some embodiments, bacteriophages are considered to be "functionally equivalent" as long as they exhibit similar phenotypes, e.g., similar host range, similar lytic ability, and/or threshold sequence similarity (e.g., greater than about 85%, greater than about 90%, greater than about 95%, greater than about 97%, or greater than about 99%). As used herein, the term "bacteriophage" encompasses a parent bacteriophage as well as its progeny or derivatives.

As used herein, "host range" refers to the bacteria that are susceptible to infection by a particular phage. The host range of a phage may include, but is not limited to, a strain, a species, a genus, or multiple genera of bacteria. The term encompasses phage adsorbable, non-productive infection (e.g., restrictive, abortive, lysogenic), and productive infections. In some embodiments, a phage may recognize two or more strains. In some embodiments, a phage may recognize and lyse both wild-type strains and mutant strains of a particular bacteria (i.e., KP2).

Different phage isolates may be prepared and phenotyped using methods known in the art, e.g., a plaque assay, liquid media assay, solid media assay. In some embodiments, the solid media assays to quantify and isolate phage are based on plaque assays (Abedon & Yin, 2009), ranging from efficiency of plating (EOP) (Kutter, 2009) to spot testing (Hyman & Abedon, 2010). In some embodiments, the plate format used for the plaque assay can be modified, e.g., from a petri dish to a 48-well plate.

In some embodiments, a double-layer plaque assay (also termed double agar overlay plaque assay) is used to phenotype bacteriophage isolates. For example, a starter culture of 4 mL BHIS may be inoculated with 5-10 colonies from a plate. This culture may be incubated at 37° C. for 1.5-2 hours. A volume of 100 µL of this culture may be mixed with 100 µL of a phage-containing sample (or medium only control) and incubated for 15 minutes. Thereafter, 3 mL of BHIS top agar (pre-molten 0.4% agar BHIS supplemented with 1 mM $Ca^{2+}$ and $Mg^{2+}$ ions) may be added, and the mixture may be poured over a BHIS bottom agar plate (1.5% agar BHIS). The plates may be left to gel at room temperature, and then incubated for 2-3 hours at 37° C. until plaques are identified.

In some embodiments, a modified spot drop assay is used to phenotype bacteriophage isolates. For example, a starter culture of 4 mL BHIS may be inoculated with 5-10 colonies from a plate. This culture may be incubated at 37° C. for 1.5-2 hours. A volume of 100 µL of this culture may be mixed with 3 mL of BHIS top agar (pre-molten 0.4% agar BHIS supplemented with 1 mM $Ca^{2+}$ and $Mg^{2+}$ ions), and 100 µL of this mixture may be dispensed per well of a Nunc 48-well plate already containing 1 mL per well of BHIS bottom agar. After solidifying at room temperature, the plates may be incubated for 30 minutes at 37 degrees. At this stage, 10 µL of samples containing phage or media only controls may be dropped in the middle of the well, left to absorb, and then may be incubated for 2-3 hours until plaques are visible for counting.

In some embodiments, a liquid media assay is used to phenotype the bacteriophage. In some embodiments, liquid-based phage infection assays follow the time-course of infection and can provide more than quantitative end-points of infection as compared to the solid-phase plaque assays. In some embodiments, by mixing phage with bacteria in liquid medium, then following the turbidity of the culture over time, one can discern finer differences (e.g., a delay in the time of cell lysis) between how different bacterial strains interact with the phage. In some embodiments, the liquid media assay allows for high-throughput measurements by using 96-well plates and reading optical density in a plate reader.

For example, a bacterial strain may be grown for 1.5-2 hours until an OD600 of about 1.7-2. This culture may then be diluted using BHIS medium to a starting optical density, typically between 0.05 and 0.2 OD600. A volume of 200 µL of culture may then be dispensed into the wells of a Nunclon flat-bottomed 96-well plate. 10 µL of a sample containing phage or 10 µL of medium as control may be added to each well. The wells may be covered with 50 µL of mineral oil to limit evaporation, and a thin sterile optically transparent polyester film may be added to keep the culture sterile. Optical density measurements may be carried out every 15 minutes, e.g., in a Tecan Infinite M200 plate reader connected to a Tecan EVO75 robot. Between measurements, the plate may be incubated while shaking at 37° C., e.g., inside the EVO75 incubator.

In some embodiments, a biofilm assay may be used to identify phage that are capable of penetrating KP2 biofilm and/or reducing the number of viable bacteria found therein. For example, KP2 may be grown at 37° C. with agitation to an OD600 of about 1.5 and diluted in LB medium supplemented with 1% glucose to an OD600 of about 0.1. For biofilm formation, 200 µl may be added to 96 well plates and incubated for 24 hrs at 37° C., e.g., to enable growth to approximately $4\times10^8$ cells per well. 180 µl may be discarded to remove planktonic cells and 50 µl of the individual phage or cocktails may be applied at MOI of 0.01 ($4\times10^6$ total phage particles). Phage buffer may be added to untreated wells as a negative control. 150 µl of LB supplemented with 1% glucose and 1 mM MMC ions may be added and incubated at 37° C. At set time points, the liquid may be removed and the biofilm scraped rigorously from the bottom of the wells. 100 µl PBS may be added to the wells, mixed and moved to sterile eppendorfs with 900 µl PBS. Samples may be vortexed for 1 minute and washed 3 times by centrifuging at 4° C. for 5 minutes at 6000×g. After the last wash, 200 µl PBS may be added and samples may be serially diluted by 10 fold in PBS. A 5 µl drop of each dilution may be plated on BHIS agar plates. Plates may be incubated overnight at 37° C. after which bacterial concentration may be determined by viable count.

In some embodiments, infectivity is determined by the plaque presence in a solid assay only. In some embodiments, infectivity is determined by the decrease in the bacterial culture optical density in a liquid assay only. In some embodiments, infectivity is determined by the decrease in the bacterial culture optical density and plaque presence in both the liquid assay and the solid assay.

As used herein, a "lytic" bacteriophage refers to a virulent bacteriophage that in the course of infection attaches to a bacterial host, inserts its genetic material into the bacterial host cell and ultimately lyses the host. Phage usually follows one of two life cycles, lytic (virulent) or lysogenic (temperate). Lytic phages take over the machinery of the cell to make phage components. They then destroy, or lyse, the cell, releasing new phage particles. Lysogenic phages incorporate their nucleic acid into the chromosome of the host cell and replicate with it as a unit without destroying the cell. Under certain conditions lysogenic phages can be induced to follow a lytic cycle. In some embodiments, following the infection, new bacteriophage particles are released. In some embodiments, following the infection, the host bacterial cells are lysed and destroyed. In some embodiments, less than 90% of the host bacterial cells are lysed and destroyed. See, e.g., Abedon et al., 2011; Sulakvelidze et al., 2001; Green et al., 2017.

In some embodiments, the % lysis is measured by methods known in the art and described herein, e.g., by optical density (OD) or qPCR.

In some embodiments, the infection of bacterial host by the phage reduces the growth rate of the host population. Growth rate reduction may be measured by methods known in the art and described herein, e.g., by optical density (OD) or qPCR. For example, two bacterial samples of identical composition (duplicates) may be cultured with two different phage or phage cocktails starting at same time point. The OD of each sample is taken at certain time points and the OD readings compared. The bacterial population in a sample with lower OD has an average lower growth rate up till that time point.

As used herein, "% homology" refers to the level of nucleic acid sequence identity or amino acid sequence identity between a first nucleic acid or amino acid sequence when aligned to a second nucleic acid or amino acid sequence using a sequence alignment program. When a position in the first and the second sequences is occupied by the same nucleic acid or amino acid (e.g., if a position in the first nucleic acid sequence and the second nucleic acid sequence is occupied by cytosine), then the first and the second sequences are homologous at that position.

In general, homology between two sequences is calculated from the number of matching or homologous positions shared by the two sequences over the total number of positions compared. In some embodiments, the first and the second sequences are aligned in a manner to maximize % homology. In some embodiments, % homology refers to the % identity over the shorter of two sequences. In some embodiments, the % homology for a nucleic acid sequence includes intergenic regions. Exemplary levels of % homology include, but are not limited to, 80, 81, 82, 83, 84, 85, 86, 87, 88, 89, 90, 91, 92, 93, 94, 95, 96, 97, 98, 99% or more sequence identity between a first and a second sequence.

Exemplary sequence alignment programs that may be used to determine % homology between two sequences include, but are not limited to, the FASTA package (including rigorous (SSEARCH, LALIGN, GGSEARCH and GLSEARCH) and heuristic (FASTA, FASTX/Y, TFASTX/Y and FASTS/M/F) algorithms, the EMBOSS package (Needle, stretcher, water and matcher), the BLAST programs (including, but not limited to BLASTN, BLASTX, TBLASTX, BLASTP, TBLASTN), megablast and BLAT. In some embodiments, the sequence alignment program is BLASTN. For example, 95% homology refers to 95% sequence identity determined by BLASTN, by combining all non-overlapping alignment segments (BLAST HSPs), summing their numbers of identical matches and dividing this sum with the length of the shorter sequence.

In some embodiments, the sequence alignment program is a basic local alignment program, e.g., BLAST. In some embodiments, the sequence alignment program is a pairwise global alignment program. In some embodiments, the pairwise global alignment program is used for protein-protein alignments. In some embodiments, the pairwise global alignment program is Needle. In some embodiments, the sequence alignment program is a multiple alignment program. In some embodiments, the multiple alignment program is MAFFT. In some embodiments, the sequence alignment program is a whole genome alignment program. In some embodiments, the whole genome alignment is performed using BLASTN. In some embodiments, BLASTN is utilized without any changes to the default parameters.

As used herein, a "pharmaceutical composition" refers to a preparation of the bacteriophage of the invention with other components such as a physiologically suitable carrier and/or excipient.

"Physiologically acceptable carrier" and "pharmaceutically acceptable carrier" are used interchangeably herein to refer to a carrier or a diluent that does not cause significant irritation to an organism and does not abrogate the biological activity and properties of the administered bacteriophage composition. An adjuvant is included under these phrases.

The term "excipient" refers to an inert substance added to a pharmaceutical composition to further facilitate administration of an active ingredient. Examples include, but are not limited to, calcium bicarbonate, calcium phosphate, various sugars and types of starch, cellulose derivatives, gelatin, vegetable oils, polyethylene glycols, and surfactants, including, e.g., polysorbate 20.

The terms "therapeutically effective dose" and "therapeutically effective amount" are used to refer to an amount of a compound that results in prevention, delay of onset of symptoms, or amelioration of symptoms of IBD compared to an untreated control. A therapeutically effective amount may, for example, be sufficient to treat, prevent, reduce the severity, delay the onset, and/or reduce the risk of occurrence of one or more symptoms of IBD compared to an untreated control.

As used herein, "gastrointestinal tract" encompasses the organs, glands, tracts, and systems that are responsible for the transfer and digestion of food, absorption of nutrients, and excretion of waste. In humans, the "gastrointestinal tract" starts at the mouth and ends at the anus, and additionally comprises the esophagus, stomach, small intestine, and large intestine. The upper gastrointestinal tract comprises the mouth, esophagus, stomach, and duodenum of the small intestine. The lower gastrointestinal tract comprises the remainder of the small intestine, i.e., the jejunum and ileum, and all of the large intestine, i.e., the cecum, colon, rectum, and anal canal. Bacteria can be found throughout the intestine.

In some embodiments, different portions of the gastrointestinal tract may be associated with disease. In CD, for example, the bacteriophage may be formulated to target bacteria present in the small intestine, colon, ileum, ileocecal junction, esophagus, mouth, and/or anus. In UC, for example, the bacteriophage may be formulated to target bacteria present in the colon, rectum, anus, and large intestine of a mammal.

The articles "a" and "an" as used herein, should be understood to mean "at least one," unless clearly indicated to the contrary.

The phrase "and/or", when used between elements in a list, is intended to mean either (1) that only a single listed element is present, or (2) that more than one element of the list is present. For example, "A, B, and/or C" indicates that the selection may be A alone; B alone; C alone; A and B; A and C; B and C; or A, B, and C. The phrase "and/or" may be used interchangeably with "at least one of" or "one or more of" the elements in a list.

All ranges include end points. All references cited are incorporated by reference in their entireties for any purpose (specification controls where there are inconsistencies).

Singular form includes plural.

Bacteriophage

The bacteriophage and bacteriophage cocktails described herein are capable of lysing one or more *Klebsiella* bacterial strains that are associated with IBD, e.g., ulcerative colitis, Crohn's disease. In some embodiments, the bacteriophage and bacteriophage cocktails are capable of lysing one or more *Klebsiella pneumoniae* bacterial strains that are associated with IBD. In some embodiments, the bacteriophage and bacteriophage cocktails are capable of modulating IBD by lysing the one or more *Klebsiella* bacteria in a mammal. In some embodiments, the bacteriophage and bacteriophage cocktails are capable of modulating IBD by lysing the one or more *Klebsiella* bacteria in the gastrointestinal tract of a mammal. In some embodiments, the bacteriophage and bacteriophage cocktails are capable of modulating IBD by lysing the one or more *Klebsiella* bacteria in the mouth of a mammal. In some embodiments, the bacteriophage and bacteriophage cocktails are capable of modulating IBD by lysing the one or more *Klebsiella* bacteria in the small intestine of a mammal. In some embodiments, the bacteriophage and bacteriophage cocktails are capable of modulating IBD by lysing the one or more *Klebsiella* bacteria in the stomach of a mammal.

In some embodiments, the bacteriophage and bacteriophage cocktails are capable of modulating IBD associated with proton pump inhibitor (PPI) therapy (Juillerat et al., 2012) by lysing the one or more *Klebsiella* bacteria. In some embodiments, the bacteriophage and bacteriophage cocktails are capable of modulating IBD associated with primary sclerosing cholangitis (Hirschfield et al., 2013; Palmela et al., 2017) by lysing the one or more *Klebsiella* bacteria.

In some embodiments, a bacteriophage may be classified as a member of a particular bacteriophage family by methods or combinations of methods known in the art and disclosed herein. Non-limiting examples of bacteriophage families include Myoviridae Type 2 (e.g., phages T4 or RB43), Podoviridae Type 3 (e.g., phages phiYeO3-12, T3 or T7) and Siphoviridae Type 1 (e.g., phages T1, TLS or RTP).

In some embodiments, bacteriophage may be sequenced and reads may be assembled, e.g., using SPAdes. See, e.g., Bankevich et al., 2012. In some embodiments, prediction of open reading frames and translation into amino acid sequences may be performed on the assembled bacteriophage genomes, e.g., using Prokka. See, e.g., Seemann 2014.

In some embodiments, bacteriophage are classified as members of a family by analyzing the phage structural genes, e.g., using VIRFAM. See, e.g., Lopes et al. 2014.

In some embodiments, bacteriophage are classified as members of a family by analyzing the assembled phage genome, e.g., as compared to phage genome in the NCBI Reseq database, e.g., with BLAST. See, e.g., O'Leary et al. 2016; Camacho et al. 2009. In some embodiments, the BLAST cutoff for % identity is at least about 50%, 60%, 70%, 80%, or 90%. In some embodiments, the BLAST cutoff for % identity is about 80%. In some embodiments, the BLAST cutoff for query coverage is at least about 50%, 60%, 70%, 80%, or 90%. In some embodiments, the BLAST cutoff for query coverage is about 70%. In some embodiments, the BLAST cutoff for % identity is 80%, and the BLAST cutoff for query coverage is about 70%. In some embodiments, the taxonomic annotation of the best hit from the BLAST search is used.

In some embodiments, bacteriophage are classified as members of a family by analyzing the phage protein sequences, e.g., as compared to phage proteomes in the NCBI Refseq database, e.g., with BLAST. See, e.g., O'Leary et al. 2016; Camacho et al. 2009. In some embodiments, the BLAST cutoff for % identity is at least about 30%, 40%, 50%, 60%, or 70%. In some embodiments, the BLAST cutoff for % identity is about 50%. In some embodiments, the BLAST cutoff for query coverage is at least about 30%, 40%, 50%, 60%, or 70%. In some embodiments, the BLAST cutoff for query coverage is about 50%. In some embodiments, the BLAST cutoff for % identity is 50%, and the BLAST cutoff for query coverage is about 50%. In some embodiments, a reference genome is determined for the phage by the protein sequences in the BLAST search with highest homology. In some embodiments, the taxonomic annotation of the phage may be inferred from the taxonomic annotation of the reference genome, optionally in addition to other genomes with over 40% homology to the reference sequence.

The taxonomy annotation obtained from the methods disclosed herein may be generally consistent with one another. In the event of discrepancies, discrepancies may be resolved by using the International Committee on Taxonomy of Viruses (ICTV) specific taxon threshold.

In some embodiments, the bacteriophage is capable of lysing at least one, two, three, four, or five bacteria selected from KP2 (ACCESSION NO. DSM 33048), CT-141-1 (ACCESSION NO. DSM 33052), CT-123-1 (ACCESSION NO. DSM 33051), MKP2_2161_1 (ACCESSION NO. DSM 33055), MKP2_251_B (ACCESSION NO. DSM 33053), MKP2_251_C (ACCESSION NO. DSM 33054), and 8M-all (ACCESSION NO. DSM 33050).

In some embodiments, the bacteriophage is selected from 1.2-2 (ACCESSION NO. DSM 33068), colon-11, PKP-55 (ACCESSION NO. DSM 33064), or any other member of the family Myoviridae, subfamily Tevenvirinae, genus Kp15virus that is capable of infecting at least two of *Klebsiella pneumoniae* strains KP2, CT-123-1, MKP2_2161_1, and MKP2_251_B. In some embodiments, the bacteriophage is selected from 1.2-2, colon-11, and PKP-55. The bacteriophage identified in this paragraph may be referred to as "Group 1" bacteriophage and may be capable of infecting the bacterial strains described in this paragraph. In some embodiments, Group 1 consists of 1.2-2, colon-11, and PKP-55.

In some embodiments, the bacteriophage is selected from M16-7a, KP2-4a, M16-4a, colon-36, KP2-5-1 (ACCESSION NO. DSM 33067), 1.2-4br, 1.2-4s, M16-6c, KP2-9a, M16-9a, KP2-5a, colon-14-15, colon-6, colon1, M16-3-2c, M16-5c, or any other member of the family Myoviridae, subfamily Tevenvirinae, genus T4virus that is capable of infecting at least two of *Klebsiella pneumoniae* strains KP2, CT-123-1, MKP2_2161_1, and MKP2_251_B. In some embodiments, the bacteriophage is selected from M16-7a, KP2-4a, M16-4a, colon-36, KP2-5-1, 1.2-4br, 1.2-4s, M16-6c, KP2-9a, M16-9a, KP2-5-1, colon-14-15, colon-6, colon1, M16-3-2c, and M16-5c. The bacteriophage identified in this paragraph may be referred to as "Group 2" bacteriophage and may be capable of infecting the bacterial strains described in this paragraph. In some embodiments, Group 2 consists of M16-7a, KP2-4a, M16-4a, colon-36, KP2-5-1, 1.2-4br, 1.2-4s, M16-6c, KP2-9a, M16-9a, KP2-5-1, colon-14-15, colon-6, colon1, M16-3-2c, and M16-5c.

In some embodiments, the bacteriophage is selected from KP2-15-2-1, KP2-14, KP2-15-1, colon-14, 1.2-3b (ACCESSION NO. DSM 330066), KP2-8c, KP2-7c, KP2-7-1c, KP2-8a, KP2-5, KP2-16-1, or any other member of the family Podoviridae, subfamily Autographivirinae, genus T7virus that is capable of infecting *Klebsiella pneumoniae* strains KP2 and MKP2_251_B. In some embodiments, the bacteriophage is selected from KP2-15-2-1, KP2-14, KP2-15-1, colon-14, 1.2-3b, KP2-8c, KP2-7c, KP2-7-1c, KP2-8a, KP2-5, and KP2-16-1. The bacteriophage identified in this paragraph may be referred to as "Group 3" bacteriophage and may be capable of infecting the bacterial strains described in this paragraph. In some embodiments, Group 3 consists of KP2-15-2-1, KP2-14, KP2-15-1, colon-14, 1.2-3b, KP2-8c, KP2-7c, KP2-7-1c, KP2-8a, KP2-5, and KP2-16-1.

In some embodiments, the bacteriophage is selected from MCoc4c, MCoc6c, Mcoc7c, MCoc3c, MCoc5c (ACCESSION NO. DSM 33069), MCoc15c, MCoc8a, MCoc9-2c, M16-9-1c, MCoc9-1c, or any other member of the family Podoviridae, subfamily Autographivirinae, genus Kp34virus that is capable of infecting at least three of *Klebsiella pneumoniae* strains CT-141-1, CT-123-1, MKP2_2161_1, and MKP2_251_C.

In some embodiments, the bacteriophage is selected from MCoc4c, MCoc6c, Mcoc7c, MCoc3c, MCoc5c, MCoc15c, MCoc8a, MCoc9-2c, M16-9-1c, and MCoc9-1c. The bacteriophage identified in this paragraph may be referred to as "Group 4" bacteriophage and may be capable of infecting the bacterial strains described in this paragraph. In some embodiments, Group 4 consists of MCoc4c, MCoc6c, Mcoc7c, MCoc3c, MCoc5c, MCoc15c, MCoc8a, MCoc9-2c, M16-9-1c, and MCoc9-1c.

In some embodiments, the bacteriophage is selected from 8M-8 (ACCESSION NO. DSM 33071) or any other member of the family Myoviridae, subfamily Vequintavirinae, genus ScIvirus that is capable of infecting *Klebsiella pneumoniae* strains CT-123-1, MKP2_2161_1, and 8M-all. In some embodiments, the bacteriophage is 8M-8. The bacteriophage identified in this paragraph may be referred to as "Group 5" bacteriophage and may be capable of infecting the bacterial strains described in this paragraph. In some embodiments, Group 5 consists of 8M-8.

In some embodiments, the bacteriophage is selected from 8M-1 (ACCESSION NO. DSM 33072), 8M-7 (ACCESSION NO. DSM 33070), 1.2-3s (ACCESSION NO. DSM 33065) or any other member of the family Siphoviridae that is capable of infecting at least two of *Klebsiella pneumoniae* strains KP2, CT-123-1, MKP2_2161_1, MKP2_251_B, and 8M-all. In some embodiments, the bacteriophage is selected from 8M-1, 8M-7, and 1.2-3s. The bacteriophage identified in this paragraph may be referred to as "Group 6" bacteriophage and may be capable of infecting the bacterial strains described in this paragraph. In some embodiments, Group 6 consists of 8M-1, 8M-7, and 1.2-3s.

In some embodiments, the bacteriophage is capable of lysing KP2 and at least one bacteria, at least two bacteria, at least three bacteria, at least four bacteria, or at least five bacteria selected from CT-141-1, CT-123-1, MKP2_2161_1, MKP2_251_B, MKP2_251_C and 8M-all.

As used herein, a bacteriophage "cocktail" refers to a composition comprising at least two different isolates of bacteriophage, e.g., lytic bacteriophage, as described herein.

As used herein, "a" or "one" bacteriophage refers to an isolate or type of bacteriophage and is not necessarily intended to refer to a single bacteriophage particle.

In some embodiments, the bacteriophage cocktail comprises at least two different KP2 bacteriophages described herein and is capable of infecting wild-type KP2 bacteria.

In some embodiments, the cocktail comprises at least two different KP2 bacteriophages described herein and is capable of infecting mutant KP2 bacteria. In some embodiments, the cocktail comprises at least two different KP2 bacteriophages described herein and is capable of infecting wild-type KP2 bacteria and mutant KP2 bacteria.

In some embodiments, the cocktail comprises at least three different KP2 bacteriophages described herein and is capable of infecting wild-type KP2 bacteria. In some embodiments, the cocktail comprises at least three different KP2 bacteriophages described herein and is capable of infecting mutant KP2 bacteria. In some embodiments, the cocktail comprises at least three different KP2 bacteriophages described herein and is capable of infecting wild-type KP2 bacteria and mutant KP2 bacteria.

In some embodiments, the cocktail comprises at least four different KP2 bacteriophages described herein and is capable of infecting wild-type KP2 bacteria. In some embodiments, the cocktail comprises at least four different KP2 bacteriophages described herein and is capable of infecting mutant KP2 bacteria. In some embodiments, the cocktail comprises at least four different KP2 bacteriophages described herein and is capable of infecting wild-type KP2 bacteria and mutant KP2 bacteria.

In some embodiments, the cocktail comprises bacteriophage selected from at least three of the following groups: Group 1, Group 2, Group 3, Group 4, Group 5, and Group 6 as described herein. In some embodiments, the cocktail comprises bacteriophage selected from at least four of the following groups: Group 1, Group 2, Group 3, Group 4, Group 5, and Group 6 as described herein. In some embodiments, the cocktail comprises at least one bacteriophage selected from Group 1, Group 5, and Group 6 and at least one bacteriophage selected from Group 2, Group 3, and Group 4 as described herein. In some embodiments, the cocktail is capable of lysing at least one, two, three, four, five, six or seven bacteria selected from KP2, CT-141-1, CT-123-1, MKP2_2161_1, MKP2_251_B, MKP2_251_C, and 8M-all. In some embodiments, the cocktail is capable of lysing KP2 and at least one bacteria, at least two bacteria, at least three bacteria, at least four bacteria, at least five bacteria, or at least six bacteria selected from CT-141-1, CT-123-1, MKP2_2161_1, MKP2_251_B, MKP2_251_C and 8M-all. In some embodiments, the cocktail is capable of lysing each of KP2, CT-141-1, CT-123-1, MKP2_2161_1, MKP2_251_B, MKP2_251_C and 8M-all.

In some embodiments, the cocktail comprises bacteriophage selected from:

(a) 1.2-2, colon-11, PKP-55, or any other bacteriophage having at least 90%, 91%, 92%, 93%, 94%, 95%, 96%, 97%, 98%, or 99% nucleotide sequence homology to any of the foregoing and that is capable of infecting at least two of *Klebsiella pneumoniae* strains KP2, CT-123-1, MKP2_2161_1, and MKP2_251_B. The bacteriophage identified in this paragraph may be referred to as "Group A" bacteriophage and may be capable of infecting the bacterial strains described in this paragraph. In some embodiments, Group A consists of 1.2-2, colon-11, and PKP-55.

(b) M16-7a, KP2-4a, M16-4a, colon-36, KP2-5-1, 1.2-4br, 1.2-4s, M16-6c, KP2-9a, M16-9a, KP2-5a, colon-14-15, colon-6, colon1, M16-3-2c, M16-5c, or any other bacteriophage having at least 90%, 91%, 92%, 93%, 94%, 95%, 96%, 97%, 98%, or 99% nucleotide sequence homology to any of the foregoing and that is capable of infecting at least two of *Klebsiella pneumoniae* strains KP2, CT-123-1, MKP2_2161_1, and MKP2_251_B. The bacteriophage identified in this paragraph may be referred to as "Group B" bacteriophage and may be capable of infecting the bacterial strains described in this paragraph. In some embodiments, Group B consists of M16-7a, KP2-4a, M16-4a, colon-36, KP2-5-1, 1.2-4br, 1.2-4s, M16-6c, KP2-9a, M16-9a, KP2-5a, colon-14-15, colon-6, colon1, M16-3-2c, and M16-5c.

(c) KP2-15-2-1, KP2-14, KP2-15-1, colon-14, 1.2-3b, KP2-8c, KP2-7c, KP2-7-1c, KP2-8a, KP2-5, KP2-16-1, or any other bacteriophage having at least 90%, 91%, 92%, 93%, 94%, 95%, 96%, 97%, 98%, or 99% nucleotide sequence homology to any of the foregoing and that is capable of infecting *Klebsiella pneumoniae* strains KP2 and MKP2_251_B. The bacteriophage identified in this paragraph may be referred to as "Group C" bacteriophage and may be capable of infecting the bacterial strains described in this paragraph. In some embodiments, Group C consists of KP2-15-2-1, KP2-14, KP2-15-1, colon-14, 1.2-3b, KP2-8c, KP2-7c, KP2-7-1c, KP2-8a, KP2-5, and KP2-16-1.

(d) MCoc4c, MCoc6c, Mcoc7c, MCoc3c, MCoc5c, MCoc15c, MCoc8a, MCoc9-2c, M16-9-1c, MCoc9-1c, or any other bacteriophage having at least 90%, 91%, 92%, 93%, 94%, 95%, 96%, 97%, 98%, or 99% nucleotide sequence homology to any of the foregoing and that is capable of infecting at least three of *Klebsiella pneumoniae* strains: CT-141-1, CT-123-1, MKP2_2161_1, and MKP2_251_C. The bacteriophage identified in this paragraph may be referred to as "Group D" bacteriophage and may be capable of infecting the bacterial strains described in this paragraph. In some embodiments, Group D consists of MCoc4c, MCoc6c, Mcoc7c, MCoc3c, MCoc5c, MCoc15c, MCoc8a, MCoc9-2c, M16-9-1c, and MCoc9-1c.

(e) 8M-8, or any other bacteriophage having at least 90%, 91%, 92%, 93%, 94%, 95%, 96%, 97%, 98%, or 99% nucleotide sequence homology to the foregoing and that is capable of infecting *Klebsiella pneumoniae* strains CT-123-1, MKP2_2161_1, and 8M-all. The bacteriophage identified in this paragraph may be referred to as "Group E" bacteriophage and may be capable of infecting the bacterial strains described in this paragraph. In some embodiments, Group E consists of 8M-8.

(f) 8M-1, or any other bacteriophage having at least 90%, 91%, 92%, 93%, 94%, 95%, 96%, 97%, 98%, or 99% nucleotide sequence homology to the foregoing and is capable of infecting *Klebsiella pneumoniae* strains: KP2, CT-123-1, MKP2_2161_1, MKP2_251_B, and 8M-all. The bacteriophage identified in this paragraph may be referred to as "Group F" bacteriophage and may be capable of infecting the bacterial strains described in this paragraph. In some embodiments, Group F consists of 8M-1.

(g) 8M-7, or any other bacteriophage having at least 90%, 91%, 92%, 93%, 94%, 95%, 96%, 97%, 98%, or 99% nucleotide sequence homology to the foregoing and is capable of infecting *Klebsiella pneumoniae* strains: CT-123-1 and 8M-all. The bacteriophage identified in this paragraph may be referred to as "Group G" bacteriophage and may be capable of infecting the bacterial strains described in this paragraph. In some embodiments, Group G consists of 8M-7.

(h) 1.2-3s or any other bacteriophage having at least 90%, 91%, 92%, 93%, 94%, 95%, 96%, 97%, 98%, or 99% nucleotide sequence homology to the foregoing and is capable of infecting *Klebsiella pneumoniae* strains: KP2, CT-123-1, MKP2_2161_1, and 8M-all. The bacteriophage identified in this paragraph may be referred to as "Group H" bacteriophage and may be capable of infecting the bacterial strains described in this paragraph. In some embodiments, Group H consists of 1.2-3s.

In some embodiments, the cocktail comprises bacteriophage selected from at least three of the following groups: Group A, Group B, Group C, Group D, Group E, Group F, and Group H, as described herein. In some embodiments, the cocktail comprises bacteriophage selected from at least four of the following groups: Group A, Group B, Group C, Group D, Group E, Group F, and Group H, as described herein. In some embodiments, the cocktail comprises at least one bacteriophage selected from Group A, Group E, Group F, Group G, and Group H and at least one bacteriophage selected from Group B, Group C, and Group D as described herein. In some embodiments, the cocktail is capable of lysing at least one, two, three, four, five, six or seven bacteria selected from KP2, CT-141-1, CT-123-1, MKP2_2161_1, MKP2_251_B, MKP2_251_C, and 8M-all. In some embodiments, the cocktail is capable of lysing KP2 and at least one, two, three, four, five, or six bacteria selected from CT-141-1, CT-123-1, MKP2_2161_1, MKP2_251_B, MKP2_251_C and 8M-all. In some embodiments, the cocktail is capable of lysing each of KP2, CT-141-1, CT-123-1, MKP2_2161_1, MKP2_251_B, MKP2_251_C and 8M-all.

In some embodiments, for example during phage infection, mutant bacterial strains arise that are resistant to the phage. In some embodiments, it is beneficial for a phage to target the mutant bacteria. To produce said phage, bacteria may be incubated with one or more phage(s) disclosed herein to generate mutant bacterial strains. Environmental and clinical samples may then be screened for phage that are capable of infecting the mutant bacterial strains in order to identify the new phage. Then the titer of the phage(s) is selected to allow for efficient attachment, penetration, amplification and release of new phage(s) from the bacterial cells. Exemplary mutant KP2 strains are described herein. See, e.g., Table 2. In some embodiments, the mutant bacterial strain mirrors mutations that are likely to occur in vivo when a subject is treated with the phage disclosed herein. In some embodiments, a bacteriophage may be generated that is capable of infecting and lysing the mutant bacterial strain. Thus, in some embodiments, the bacteriophages provided herein are capable of treating unmodified KP2 bacteria, as well as resistant KP2 mutants.

In some embodiments, the bacterial cell surface receptors used by different phage may be identified. For example, mutant bacteria resistant to a particular bacteriophage may be isolated and characterized to detect the genomic modifications responsible for resistance. Such modified genes, particularly if they encode components of or proteins responsible for the synthesis and/or assembly of a bacterial surface protein, can indicate what surface component is responsible for infection by the particular bacteriophage. See, e.g., Avrani et al., 2011. The phage route of infection may be analyzed by infection using any one of KP2, KP2-Mcoc1 (ACCESSION NO. DSM 33049), or 8M-all, followed by selection and sequencing of infection-resistant mutant bacteria that arise in the presence of the specific bacteriophage. Mutant and native bacterial genomes may be compared to determine mutations responsible for the infection mechanism, e.g., using reference control genomes and breseq to identify mutations. See, e.g., Barrick et al. 2009, Deatherage and Barrick 2014. In some embodiments, non-silent mutations with frequency >80% may be analyzed. In some embodiments, mutations with frequency between 20-80% may be analyzed if located outside a mutation hot-spot. In some embodiments, proteins with mutations of interest may be profiled for activity, pathway, and relevance to known phage receptors.

The identification of such mutants is important in that they may potentially arise in the gastrointestinal tract and maintain their ability to cause IBD. Such mutants should be able to be lysed by at least one bacteriophage in a composition of the invention for improved efficacy.

Non-limiting examples of genomic modifications which affect phage infection (i.e., modifications found in a phage-resistant mutant bacteria that arose in a culture containing a specific phage capable of infecting a specific bacteria) which we have identified are shown in Table 3.

In some embodiments, the cocktail comprises bacteriophage selected from at least three or four bacteriophage that in toto lyse: (a) *Klebsiella pneumoniae* strain KP2; (b) a mutant *Klebsiella pneumoniae* strain KP2 that is characterized by a mutation in a gene involved in synthesizing LPS; (c) a mutant *Klebsiella pneumoniae* strain KP2 that is characterized by a mutation in a gene involved in iron uptake; (d) a mutant *Klebsiella pneumoniae* strain KP2 that is characterized by at least one of a mutation in a gene involved in cobalamin uptake or a mutation in a gene involved in maltose transport. In some embodiments, the cocktail comprises bacteriophage selected from at least one bacteriophage that infects and/or lyses (a) *Klebsiella pneumoniae* strain KP2; and at least one, two, or three bacteriophage that in toto lyse (b) a mutant *Klebsiella pneumoniae* strain KP2 that is characterized by a mutation in a gene involved in synthesizing LPS; (c) a mutant *Klebsiella pneumoniae* strain KP2 that is characterized by a mutation in a gene involved in iron uptake; (d) a mutant *Klebsiella pneumoniae* strain KP2 that is characterized by at least one of a mutation in a gene involved in cobalamin uptake or a mutation in a gene involved in maltose transport. In some embodiments, the cocktail is capable of lysing at least one, two, three, four, five, six or seven bacteria selected from KP2, CT-141-1, CT-123-1, MKP2_2161_1, MKP2_251_B, MKP2_251_C, and 8M-all. In some embodiments, the cocktail is capable of lysing KP2 and at least one, two, three, four, five, or six bacteria selected from CT-141-1, CT-123-1, MKP2_2161_1, MKP2_251_B, MKP2_251_C and 8M-all. In some embodiments, the cocktail is capable of lysing each of KP2, CT-141-1, CT-123-1, MKP2_2161_1, MKP2_251_B, MKP2_251_C and 8M-all.

In some embodiments, the cocktail comprises bacteriophage selected from at least three or four bacteriophage that in toto lyse: (a) *Klebsiella pneumoniae* strain KP2; (b) a mutant *Klebsiella pneumoniae* strain KP2 that is characterized by a mutation in one or more of rfaQ and grcA genes; (c) a mutant *Klebsiella pneumoniae* strain KP2 that is characterized by a mutation in one or more of rfaG, wbaP, and tyrosineK genes; (d) a mutant *Klebsiella pneumoniae* strain KP2 that is characterized by a mutation in one or more of mfpsA, wecA, and fhuA genes; (e) a mutant *Klebsiella pneumoniae* strain KP2 that is characterized by a mutation in one or more of fepA, tonB and LamB genes; (f) a mutant *Klebsiella pneumoniae* strain KP2 that is characterized by a mutation in a HBAD gene; and (g) a mutant *Klebsiella pneumoniae* strain KP2 that is characterized by a mutation in a 1pxM gene. In some embodiments, the cocktail comprises bacteriophage selected from at least one bacteriophage that infects and/or lyses (a) *Klebsiella pneumoniae* strain KP2; and at least one, two, or three bacteriophage that in toto lyse (b) a mutant *Klebsiella pneumoniae* strain KP2 that is characterized by a mutation in one or more of rfaQ and grcA genes; (c) a mutant *Klebsiella pneumoniae* strain KP2 that is characterized by a mutation in one or more of rfaG, wbaP, and tyrosineK genes; (d) a mutant *Klebsiella pneumoniae* strain KP2 that is characterized by a mutation in one or more of mfpsA, wecA, and fhuA genes; (e) a mutant *Klebsiella pneumoniae* strain KP2 that is characterized by a mutation in one or more of fepA, tonB and LamB genes; (f) a mutant *Klebsiella pneumoniae* strain KP2 that is characterized by a mutation in a HBAD gene; and (g) a mutant *Klebsiella pneumoniae* strain KP2 that is characterized by a mutation in a 1pxM gene. In some embodiments, the cocktail is further capable of lysing at least one, two, three, four, five, six or seven bacteria selected from KP2, CT-141-1, CT-123-1, MKP2_2161_1, MKP2_251_B, MKP2_251_C, and 8M-all. In some embodiments, the cocktail is further capable of lysing KP2 and at least one, two, three, four, five, or six bacteria selected from CT-141-1, CT-123-1, MKP2_2161_1, MKP2_251_B, MKP2_251_C and 8M-all. In some embodiments, the cocktail is further capable of lysing each of KP2, CT-141-1, CT-123-1, MKP2_2161_1, MKP2_251_B, MKP2_251_C and 8M-all.

In some embodiments, the cocktail comprises bacteriophage that in toto lyse at least three, four, five, or six bacteria selected from (a) a mutant *Klebsiella pneumoniae* strain KP2 that is characterized by a mutation in a rfaQ gene; (b) a mutant *Klebsiella pneumoniae* strain KP2 that is characterized by a mutation in a grcA gene; (c) a mutant *Klebsiella pneumoniae* strain KP2 that is characterized by a mutation in a rfaG gene; (d) a mutant *Klebsiella pneumoniae* strain KP2 that is characterized by a mutation in a wbaP gene; (e) a mutant *Klebsiella pneumoniae* strain KP2 that is characterized by a mutation in both a tyrosineK and a wbaP gene; (f) a mutant *Klebsiella pneumoniae* strain KP2 that is characterized by a mutation in a wecA gene; (g) a mutant *Klebsiella pneumoniae* strain KP2 that is characterized by a mutation in a mfps gene; (h) a mutant *Klebsiella pneumoniae* strain KP2 that is characterized by a mutation in both a fhuA and a wecA gene; (i) a mutant *Klebsiella pneumoniae* strain KP2 that is characterized by a mutation in a fepA gene; (j) a mutant *Klebsiella pneumoniae* strain KP2 that is characterized by a mutation in both a tonB gene and a LamB gene; (k) a mutant *Klebsiella pneumoniae* strain KP2 that is characterized by a mutation in a HBAD gene; (1) a mutant *Klebsiella pneumoniae* strain KP2 that is characterized by a mutation in a 1pxM gene; and (m) a mutant *Klebsiella pneumoniae* strain KP2 that is characterized by a mutation in a fhuA gene. In some embodiments, the cocktail is further capable of lysing at least one, two, three, four, five, six or seven bacteria selected from KP2, CT-141-1, CT-123-1, MKP2_2161_1, MKP2_251_B, MKP2_251_C, and 8M-all. In some embodiments, the cocktail is further capable of lysing KP2 and at least one, two, three, four, five, or six bacteria selected from CT-141-1, CT-123-1, MKP2_2161_1, MKP2_251_B, MKP2_251_C and 8M-all. In some embodiments, thecocktail is further capable of lysing each of KP2, CT-141-1, CT-123-1, MKP2_2161_1, MKP2_251_B, MKP2_251_C and 8M-all.

In some embodiments, the cocktail comprises bacteriophage Mcoc-5c and 8M-7. In some embodiments, the cocktail comprises bacteriophage Mcoc-5c and 8M-7; and at least one bacteriophage selected from 1.2-3b, 1.2-2, and 1.2-3s. In some embodiments, the cocktail comprises bacteriophage Mcoc-5c and 8M-7; at least one bacteriophage selected from 1.2-3b, 1.2-2, and 1.2-3s; and at least one bacteriophage selected from KP2-5-1 and PKP-55. In some embodiments, the cocktail comprises bacteriophage Mcoc-5c, 8M-7, 1.2-2, 1.2-3s. In some embodiments, the cocktail comprises bacteriophage Mcoc-5c, 8M-7, 1.2-2, 1.2-3b. In some embodiments, the cocktail comprises bacteriophage Mcoc-5c, 8M-7, KP2-5-1, 1.2-3s, PKP-55. In some embodiments, the cocktail comprises bacteriophage consisting of Mcoc-5c, 8M-7, 1.2-2, 1.2-3s. In some embodiments, the cocktail comprises bacteriophage consisting of Mcoc-5c, 8M-7, 1.2-2, 1.2-3b. In some embodiments, the cocktail comprises bacteriophage consisting of Mcoc-5c, 8M-7, KP2-5-1, 1.2-3s, PKP-55.

In some embodiments, the cocktail comprises bacteriophage 1.2-3b, 1.2-2, and 1.2-3s. In some embodiments, the cocktail comprises bacteriophage 1.2-3b, 1.2-2, 1.2-3s, and Mcoc-5c. In some embodiments, the cocktail comprises bacteriophage 1.2-3b, 1.2-2, 1.2-3s, and 8M-1. In some embodiments, the cocktail comprises bacteriophage 1.2-3b, 1.2-2, 1.2-3s, Mcoc-5c, and 8M-1.

In some embodiments, the bacteriophage or cocktail does not significantly affect the subject's microbiota (other than specifically lysing IBD-causing *Klebsiella*). In some embodiments, the bacteriophage or cocktail does not significantly affect the subject's commensal bacteria. In some embodiments, the bacteriophage or cocktail does not significantly affect the subject's probiotic bacteria. In some embodiments, a bacteriophage or cocktail is not naturally capable of affecting the microbiota, commensal bacteria, or probiotic bacteria, because the bacteriophage's natural host range is limited, e.g., to KP2.

In some embodiments, a bacteriophage that is specific for a bacterium is capable of recognizing specific receptors and/or attachment sites expressed by said bacterium. In some embodiments, the KP2 bacteriophage is "specific" for KP2 bacteria. For example, the KP2 bacteriophage is capable of infecting and/or productively creating more virions in the KP2 bacteria than in a bacteria that is not the KP2 bacteria in an in vitro or in vivo assay, e.g., in a plaque assay, an OD assay, a phage-adsorption assay, or any other assay showing that the bacteriophage can enter, reproduce, and exit the bacteria.

Bacterial Lysis

In some embodiments, the bacteriophage provided herein is capable of lysing deleterious *Klebsiella* bacteria that induce immune and/or inflammatory response(s). In some embodiments, the bacteriophage provided herein is capable of lysing deleterious *Klebsiella* bacteria that disrupt the balance of immune homeostasis in the intestine, e.g., by enhancing the pro-inflammatory activity, ultimately resulting in chronic intestinal inflammation. In some embodiments, the bacteriophage provided herein is capable of lysing deleterious *Klebsiella* bacteria that induce a T helper 1 (TH1) cell response. In some embodiments, the *Klebsiella* bacteria to be lysed by the bacteriophage provided herein are in the lumen. In some embodiments, the *Klebsiella* bacteria to be lysed by the bacteriophage provided herein are associated with the mucosa or epithelium. In some embodiments, the *Klebsiella* bacteria to be lysed by the bacteriophage provided herein are in between the mucosal and submucosal layer in the ileum, e.g., in Crohn's disease (Chiodini et al., 2015).

In some embodiments, the bacteriophage provided herein is capable of lysing deleterious KP2 bacteria that are associated with IBD, e.g., ulcerative colitis or Crohn's disease, and may be administered to ameliorate the disease or at least one symptom thereof. In some embodiments, there is a higher incidence of KP2 bacteria associated with Crohn's disease as compared to ulcerative colitis. However, in embodiments where a subject has ulcerative colitis associated with KP2 bacterial presence, the bacteriophage provided herein may be administered to lyse those bacteria and ameliorate the ulcerative colitis or at least one symptom thereof.

Drugs that inhibit gastric acid secretion, e.g., proton pump inhibitors, and primary sclerosing cholangitis (PSC) may alter the course of IBD. In some embodiments, the bacteriophage provided herein is capable of lysing KP2 bacteria that are more prevalent in a subject receiving proton pump inhibitor therapy or suffering from PSC and may be administered to ameliorate at least one symptom of IBD associated with proton pump inhibitor therapy or PSC.

Pharmaceutical Compositions

Pharmaceutical compositions comprising the bacteriophage or cocktails described herein may be used to modulate IBD. Pharmaceutical compositions comprising the bacteriophage or cocktails, alone or in combination with prophylactic agents, therapeutic agents, and/or and pharmaceutically acceptable carriers are provided. In certain embodiments, the pharmaceutical composition comprises one bacteriophage described herein. In alternate embodiments, the pharmaceutical composition comprises two or more bacteriophages, e.g., a cocktail of bacteriophage, described herein.

In some embodiments, the pharmaceutical composition comprises bacteriophage selected from at least three of the following groups: Group 1, Group 2, Group 3, Group 4, Group 5, and Group 6 as described herein. In some embodiments, the pharmaceutical composition comprises bacteriophage selected from at least four of the following groups:

Group 1, Group 2, Group 3, Group 4, Group 5, and Group 6 as described herein. In some embodiments, the pharmaceutical composition comprises at least one bacteriophage selected from Group 1, Group 5, and Group 6 and at least one bacteriophage selected from Group 2, Group 3, and Group 4 as described herein.

In some embodiments, the pharmaceutical composition comprises bacteriophage selected from at least three of the following groups: Group A, Group B, Group C, Group D, Group E, Group F, and Group H, as described herein. In some embodiments, the pharmaceutical composition comprises bacteriophage selected from at least four of the following groups: Group A, Group B, Group C, Group D, Group E, Group F, and Group H, as described herein. In some embodiments, the pharmaceutical composition comprises at least one bacteriophage selected from Group A, Group E, Group F, Group G, and Group H and at least one bacteriophage selected from Group B, Group C, and Group D as described herein.

In some embodiments, the pharmaceutical composition comprises bacteriophage selected from at least three or four bacteriophage that in toto lyse: (a) *Klebsiella pneumoniae* strain KP2; (b) a mutant *Klebsiella pneumoniae* strain KP2 that is characterized by a mutation in a gene involved in synthesizing LPS; (c) a mutant *Klebsiella pneumoniae* strain KP2 that is characterized by a mutation in a gene involved in iron uptake; (d) a mutant *Klebsiella pneumoniae* strain KP2 that is characterized by at least one of a mutation in a gene involved in cobalamin uptake or a mutation in a gene involved in maltose transport.

In some embodiments, the pharmaceutical composition comprises bacteriophage selected from at least one bacteriophage that infects and/or lyses (a) *Klebsiella pneumoniae* strain KP2; and at least one, two, or three bacteriophage that in toto lyse (b) a mutant *Klebsiella pneumoniae* strain KP2 that is characterized by a mutation in a gene involved in synthesizing LPS; (c) a mutant *Klebsiella pneumoniae* strain KP2 that is characterized by a mutation in a gene involved in iron uptake; (d) a mutant *Klebsiella pneumoniae* strain KP2 that is characterized by at least one of a mutation in a gene involved in cobalamin uptake or a mutation in a gene involved in maltose transport. In some embodiments, the pharmaceutical composition is further capable of lysing at least one, two, three, four, five, six or seven bacteria selected from KP2, CT-141-1, CT-123-1, MKP2_2161_1, MKP2_251_B, MKP2_251_C, and 8M-all. In some embodiments, the pharmaceutical composition is further capable of lysing KP2 and at least one, two, three, four, five, or six bacteria selected from CT-141-1, CT-123-1, MKP2_2161_1, MKP2_251_B, MKP2_251_C and 8M-all. In some embodiments, the pharmaceutical composition is further capable of lysing each of KP2, CT-141-1, CT-123-1, MKP2_2161_1, MKP2_251_B, MKP2_251_C and 8M-all.

In some embodiments, the pharmaceutical composition comprises bacteriophage selected from at least three or four bacteriophage that in toto lyse: (a) *Klebsiella pneumoniae* strain KP2; (b) a mutant *Klebsiella pneumoniae* strain KP2 that is characterized by a mutation in one or more of rfaQ and grcA genes; (c) a mutant *Klebsiella pneumoniae* strain KP2 that is characterized by a mutation in one or more of rfaG, wbaP, and tyrosineK genes; (d) a mutant *Klebsiella pneumoniae* strain KP2 that is characterized by a mutation in one or more of mfpsA, wecA, and fhuA genes; (e) a mutant *Klebsiella pneumoniae* strain KP2 that is characterized by a mutation in one or more of fepA, tonB and LamB genes; (f) a mutant *Klebsiella pneumoniae* strain KP2 that is characterized by a mutation in a HBAD gene; and (g) a mutant *Klebsiella pneumoniae* strain KP2 that is characterized by a mutation in a 1pxM gene. In some embodiments, the pharmaceutical composition is further capable of lysing at least one, two, three, four, five, six or seven bacteria selected from KP2, CT-141-1, CT-123-1, MKP2_2161_1, MKP2_251_B, MKP2_251_C, and 8M-all. In some embodiments, the pharmaceutical composition is further capable of lysing KP2 and at least one, two, three, four, five, or six bacteria selected from CT-141-1, CT-123-1, MKP2_2161_1, MKP2_251_B, MKP2_251_C and 8M-all. In some embodiments, the pharmaceutical composition is further capable of lysing each of KP2, CT-141-1, CT-123-1, MKP2_2161_1, MKP2_251_B, MKP2_251_C and 8M-all.

In some embodiments, the pharmaceutical composition comprises bacteriophage selected from at least one bacteriophage that infects and/or lyses (a) *Klebsiella pneumoniae* strain KP2; and at least one, two, or three bacteriophage that in toto lyse (b) a mutant *Klebsiella pneumoniae* strain KP2 that is characterized by a mutation in one or more of rfaQ and grcA genes; (c) a mutant *Klebsiella pneumoniae* strain KP2 that is characterized by a mutation in one or more of rfaG, wbaP, and tyrosineK genes; (d) a mutant *Klebsiella pneumoniae* strain KP2 that is characterized by a mutation in one or more of mfpsA, wecA, and fhuA genes; (e) a mutant *Klebsiella pneumoniae* strain KP2 that is characterized by a mutation in one or more of fepA, tonB and LamB genes; (f) a mutant *Klebsiella pneumoniae* strain KP2 that is characterized by a mutation in a HBAD gene; and (g) a mutant *Klebsiella pneumoniae* strain KP2 that is characterized by a mutation in a 1pxM gene. In some embodiments, the pharmaceutical composition is further capable of lysing at least one, two, three, four, five, six or seven bacteria selected from KP2, CT-141-1, CT-123-1, MKP2_2161_1, MKP2_251_B, MKP2_251_C, and 8M-all. In some embodiments, the pharmaceutical composition is further capable of lysing KP2 and at least one, two, three, four, five, or six bacteria selected from CT-141-1, CT-123-1, MKP2_2161_1, MKP2_251_B, MKP2_251_C and 8M-all. In some embodiments, the pharmaceutical composition is further capable of lysing each of KP2, CT-141-1, CT-123-1, MKP2_2161_1, MKP2_251_B, MKP2_251_C and 8M-all.

In some embodiments, the pharmaceutical composition comprises bacteriophage that in toto lyse at least three, four, five, or six bacteria selected from (a) a mutant *Klebsiella pneumoniae* strain KP2 that is characterized by a mutation in a rfaQ gene; (b) a mutant *Klebsiella pneumoniae* strain KP2 that is characterized by a mutation in a grcA gene; (c) a mutant *Klebsiella pneumoniae* strain KP2 that is characterized by a mutation in a rfaG gene; (d) a mutant *Klebsiella pneumoniae* strain KP2 that is characterized by a mutation in a wbaP gene; (e) a mutant *Klebsiella pneumoniae* strain KP2 that is characterized by a mutation in both a tyrosineK and a wbaP gene; (f) a mutant *Klebsiella pneumoniae* strain KP2 that is characterized by a mutation in a wecA gene; (g) a mutant *Klebsiella pneumoniae* strain KP2 that is characterized by a mutation in a mfps gene; (h) a mutant *Klebsiella pneumoniae* strain KP2 that is characterized by a mutation in both a fhuA and a wecA gene; (i) a mutant *Klebsiella pneumoniae* strain KP2 that is characterized by a mutation in a fepA gene; (j) a mutant *Klebsiella pneumoniae* strain KP2 that is characterized by a mutation in both a tonB gene and a LamB gene; (k) a mutant *Klebsiella pneumoniae* strain KP2 that is characterized by a mutation in a HBAD gene; (l) a mutant *Klebsiella pneumoniae* strain KP2 that is characterized by a mutation in a 1pxM gene; and (m) a mutant *Klebsiella pneumoniae* strain KP2 that is characterized by a mutation in a fhuA gene. In some embodiments, the pharmaceutical composition is further capable of lysing at least one, two, three, four, five, six or seven bacteria selected from KP2, CT-141-1, CT-123-1, MKP2_2161_1, MKP2_251_B, MKP2_251_C, and 8M-all. In some embodiments, the pharmaceutical composition is further capable of lysing KP2 and at least one, two, three, four, five, or six bacteria selected from CT-141-1, CT-123-1, MKP2_2161_1, MKP2_251_B, MKP2_251_C and 8M-all. In some embodiments, the pharmaceutical composition is further capable of lysing each of KP2, CT-141-1, CT-123-1, MKP2_2161_1, MKP2_251_B, MKP2_251_C and 8M-all.

In some embodiments, the pharmaceutical composition comprises bacteriophage Mcoc-5c and 8M-7. In some embodiments, the pharmaceutical composition comprises bacteriophage Mcoc-5c and 8M-7; and at least one bacteriophage selected from 1.2-3b, 1.2-2, and 1.2-3s. In some embodiments, the pharmaceutical composition comprises bacteriophage Mcoc-5c and 8M-7; at least one bacteriophage selected from 1.2-3b, 1.2-2, and 1.2-3s; and at least one bacteriophage selected from KP2-5-1 and PKP-55. In some embodiments, the pharmaceutical composition comprises bacteriophage Mcoc-5c, 8M-7, 1.2-2, 1.2-3s. In some embodiments, the pharmaceutical composition comprises bacteriophage Mcoc-5c, 8M-7, 1.2-2, 1.2-3b. In some embodiments, the pharmaceutical composition comprises bacteriophage Mcoc-5c, 8M-7, KP2-5-1, 1.2-3s, PKP-55. In some embodiments, the pharmaceutical composition comprises bacteriophage consisting of Mcoc-5c, 8M-7, 1.2-2, 1.2-3s. In some embodiments, the pharmaceutical composition comprises bacteriophage consisting of Mcoc-5c, 8M-7, 1.2-2, 1.2-3b. In some embodiments, the pharmaceutical composition comprises bacteriophage consisting of Mcoc-5c, 8M-7, KP2-5-1, 1.2-3s, PKP-55.

In some embodiments, the pharmaceutical composition comprises bacteriophage 1.2-3b, 1.2-2, and 1.2-3s. In some embodiments, the pharmaceutical composition comprises bacteriophage 1.2-3b, 1.2-2, 1.2-3s, and Mcoc-5c. In some embodiments, the pharmaceutical composition comprises bacteriophage 1.2-3b, 1.2-2, 1.2-3s, and 8M-1. In some embodiments, the pharmaceutical composition comprises bacteriophage 1.2-3b, 1.2-2, 1.2-3s, Mcoc-5c, and 8M-1.

In some embodiments, the pharmaceutical composition is capable of lysing at least one, two, three, four, five, six or seven bacteria selected from KP2, CT-141-1, CT-123-1, MKP2_2161_1, MKP2_251_B, MKP2_251_C, and 8M-all. In some embodiments, the pharmaceutical composition is capable of lysing KP2 and at least one bacteria, at least two bacteria, at least three bacteria, at least four bacteria, at least five bacteria, or at least six bacteria selected from CT-141-1, CT-123-1, MKP2_2161_1, MKP2_251_B, MKP2_251_C and 8M-all. In some embodiments, the pharmaceutical composition is capable of lysing each of KP2, CT-141-1, CT-123-1, MKP2_2161_1, MKP2_251_B, MKP2_251_C and 8M-all.

The pharmaceutical compositions described herein may be formulated in a conventional manner using one or more physiologically acceptable carriers comprising excipients and auxiliaries, which facilitate processing of the active ingredients into compositions for pharmaceutical use. Methods of formulating pharmaceutical compositions are known in the art (see, e.g., "Remington's Pharmaceutical Sciences," Mack Publishing Co., Easton, PA). In some embodiments, the pharmaceutical compositions are subjected to tableting, lyophilizing, direct compression, conventional mixing, dissolving, granulating, levigating, emulsifying, encapsulating, entrapping, or spray drying to form tablets, granulates, nanoparticles, nanocapsules, microcapsules, microtablets, pellets, or powders, which may be enterically coated or uncoated. Appropriate formulation depends on the route of administration.

The bacteriophage described herein may be formulated into pharmaceutical compositions in any suitable dosage form (e.g., liquids, capsules, sachet, hard capsules, soft capsules, tablets, enteric coated tablets, suspension powders, granules, or matrix sustained release formations for oral administration) and for any suitable type of administration (e.g., oral, topical, injectable, immediate-release, pulsatile-release, delayed-release, or sustained release). In some embodiments the bacteriophage are formulated for administration as an oral rinse, a lozenge, a toothpaste, an orally dissolving strip, an orally dissolving tablet, or a gum. The composition may be administered once or more daily, weekly, or monthly.

The bacteriophage may be formulated into pharmaceutical compositions comprising one or more pharmaceutically acceptable carriers, thickeners, diluents, buffers, buffering agents, surface active agents, neutral or cationic lipids, lipid complexes, liposomes, penetration enhancers, carrier compounds, and other pharmaceutically acceptable carriers or agents. For example, the pharmaceutical composition may include, but is not limited to, the addition of calcium bicarbonate, sodium bicarbonate, calcium phosphate, various sugars and types of starch, cellulose derivatives, gelatin, vegetable oils, polyethylene glycols, and surfactants, including, for example, polysorbate 20. In some embodiments, the bacteriophage may be formulated in a solution of sodium bicarbonate, e.g., 1 molar solution of sodium bicarbonate (to buffer an acidic cellular environment, such as the stomach, for example). The bacteriophage may be administered and formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The bacteriophage may be administered orally and formulated as tablets, pills, dragees, capsules, liquids, gels, syrups, slurries, suspensions, etc. Pharmacological compositions for oral use can be made using a solid excipient, optionally grinding the resulting mixture, and processing the mixture of granules, after adding suitable auxiliaries if desired, to obtain tablets or dragee cores. Suitable excipients include, but are not limited to, fillers such as sugars, including lactose, sucrose, mannitol, or sorbitol; cellulose compositions such as maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP) or polyethylene glycol (PEG). Disintegrating agents may also be added, such as cross-linked polyvinylpyrrolidone, agar, alginic acid or a salt thereof such as sodium alginate.

In some embodiments, the bacteriophage is formulated for delivery to a mammalian mouth. In some embodiments, the pharmaceutical composition comprises the bacteriophage and a pharmaceutically acceptable excipient, wherein the bacteriophage and the pharmaceutically acceptable excipient do not occur together in nature. In some embodiments, the pharmaceutical composition comprises the bacteriophage and a pharmaceutically acceptable excipient, wherein the pharmaceutically acceptable excipient is a non-naturally occurring excipient.

In some embodiments, the bacteriophage is formulated for delivery to a mammalian intestine. In some embodiments, the pharmaceutical composition comprises the bacteriophage and a pharmaceutically acceptable excipient, wherein the bacteriophage and the pharmaceutically acceptable excipient do not occur together in nature. In some embodiments, the pharmaceutical composition comprises the bacteriophage and a pharmaceutically acceptable excipient, wherein the pharmaceutically acceptable excipient is a non-naturally occurring excipient.

Tablets or capsules can be prepared by conventional means with pharmaceutically acceptable excipients such as binding agents (e.g., pregelatinized maize starch, polyvinylpyrrolidone, hydroxypropyl methylcellulose, carboxymethylcellulose, polyethylene glycol, sucrose, glucose, sorbitol, starch, gum, kaolin, and tragacanth); fillers (e.g., lactose, microcrystalline cellulose, or calcium hydrogen phosphate); lubricants (e.g., calcium, aluminum, zinc, stearic acid, polyethylene glycol, sodium lauryl sulfate, starch, sodium benzoate, L-leucine, magnesium stearate, talc, or silica); disintegrants (e.g., starch, potato starch, sodium starch glycolate, sugars, cellulose derivatives, silica powders); or wetting agents (e.g., sodium lauryl sulphate). The tablets may be coated by methods well known in the art. A coating shell may be present, and common membranes include, but are not limited to, polylactide, polyglycolic acid, polyanhydride, other biodegradable polymers, alginate-polylysine-alginate (APA), alginate-polymethylene-co-guanidine-alginate (A-PMCG-A), hydroxymethylacrylate-methyl methacrylate (HEMA-MMA), multilayered HEMA-MMA-MAA, polyacrylonitrilevinylchloride (PAN-PVC), acrylonitrile/sodium methallylsulfonate (AN-69), polyethylene glycol/poly pentamethylcyclopentasiloxane/polydimethylsiloxane (PEG/PD5/PDMS), poly N,N-dimethyl acrylamide (PDMAAm), siliceous encapsulates, cellulose sulphate/sodium alginate/polymethylene-co-guanidine (CS/A/PMCG), cellulose acetate phthalate, calcium alginate, k-carrageenan-locust bean gum gel beads, gellan-xanthan beads, poly(lactide-co-glycolides), carrageenan, starch poly-anhydrides, starch polymethacrylates, polyamino acids, and enteric coating polymers.

In some embodiments, the bacteriophage is enterically coated for release into the gut or a particular region of the gut. The typical pH profile from the stomach to the colon is about 1-4 (stomach), 5.5-6 (duodenum), 7.3-8.0 (ileum), and 5.5-6.5 (colon). In some diseases, the pH profile may be modified. In some embodiments, the coating is degraded in specific pH environments in order to specify the site of release.

Liquid preparations for oral administration may take the form of solutions, syrups, suspensions, or a dry product for constitution with water or other suitable vehicle before use. Such liquid preparations may be prepared by conventional means with pharmaceutically acceptable agents such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of the bacteriophage.

In certain embodiments, the bacteriophage may be orally administered, for example, with an inert diluent or an assimilable edible carrier. The compound may also be enclosed in a hard- or soft-shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound by other than parenteral administration, it may be necessary to coat the compound with, or co-administer the compound with, a material to prevent its inactivation. In some embodiments, the bacteriophage is orally administered for delivery to the mouth and is capable of lysing bacteria present in the mouth. In some embodiments, the bacteriophage is orally administered for delivery to the intestine and is capable of lysing bacteria present in the intestine.

In some embodiments, the composition is formulated for intraintestinal administration, intrajejunal administration, intraduodenal administration, intraileal administration, gastric shunt administration, or intracolic administration, via nanoparticles, nanocapsules, microcapsules, or microtablets, which are enterically coated or uncoated. The pharmaceutical compositions may also be formulated in rectal compositions such as suppositories or retention enemas, using, e.g., conventional suppository bases such as cocoa butter or other glycerides. The compositions may be suspensions, solutions, or emulsions in oily or aqueous vehicles, and may contain suspending, stabilizing and/or dispersing agents.

In some embodiments, the pharmaceutically acceptable composition is in single dosage form. Single dosage forms may be in a liquid or a solid form. Single dosage forms may be administered directly to a patient without modification or may be diluted or reconstituted prior to administration. In certain embodiments, a single dosage form may be administered in bolus form, e.g., single injection, single oral dose, including an oral dose that comprises multiple tablets, capsule, pills, etc. In alternate embodiments, a single dosage form may be administered over a period of time, e.g., by infusion. Single dosage forms of the pharmaceutical composition may be prepared by portioning the pharmaceutical composition into smaller aliquots, single dose containers, single dose liquid forms, or single dose solid forms, such as tablets, granulates, nanoparticles, nanocapsules, microcapsules, microtablets, pellets, or powders, which may be enterically coated or uncoated. A single dose in a solid form may be reconstituted by adding liquid, typically sterile water or saline solution, prior to administration to a patient.

In other embodiments, the composition can be delivered in a controlled release or sustained release system. In one embodiment, a pump may be used to achieve controlled or sustained release. In another embodiment, polymeric materials can be used to achieve controlled or sustained release of the therapies of the present disclosure (see, e.g., U.S. Pat. No. 5,989,463). Examples of polymers used in sustained release formulations include, but are not limited to, poly(2-hydroxy ethyl methacrylate), poly(methyl methacrylate), poly(acrylic acid), poly(ethylene-co-vinyl acetate), poly (methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation may be inert, free of leachable impurities, stable on storage, sterile, and biodegradable. In some embodiments, a controlled or sustained release system can be placed in proximity of the prophylactic or therapeutic target, thus requiring only a fraction of the systemic dose. Any suitable technique known to one of skill in the art may be used.

Dosage regimens may be adjusted to provide a therapeutic response. Dosing can depend on several factors, including severity and responsiveness of the disease, route of administration, time course of treatment (days to months to years), and time to amelioration of the disease. For example, a single bolus may be administered at one time, several divided doses may be administered over a predetermined period of time, or the dose may be reduced or increased as indicated by the therapeutic situation.

In some embodiments, the ingredients are supplied either separately or mixed together in unit dosage form. The pharmaceutical compositions may be packaged in a hermetically sealed container such as an ampoule or sachet indicating the quantity of the agent. In one embodiment, one or more of the pharmaceutical compositions is supplied as a dry sterilized lyophilized powder or water-free concentrate in a hermetically sealed container and can be reconstituted (e.g., with water or saline) to the appropriate concentration for administration to a subject. In an embodiment, one or more of the prophylactic or therapeutic agents or pharmaceutical compositions is supplied as a dry sterile lyophilized powder in a hermetically sealed container and reconstituted prior to administration. Cryoprotectants can be included for a lyophilized dosage form, principally 0-10% sucrose (optimally 0.5-1.0%). Other suitable cryoprotectants include trehalose and lactose. Other suitable bulking agents include glycine and arginine, either of which can be included at a concentration of 0-0.05%, and polysorbate-80 (optimally included at a concentration of 0.005-0.01%). Additional surfactants include but are not limited to polysorbate 20 and BRIJ surfactants. The pharmaceutical composition may be prepared as an injectable solution and can further comprise an agent useful as an adjuvant, such as those used to increase absorption or dispersion, e.g., hyaluronidase.

Method of Treatment

Methods of treating IBD in a mammal using a bacteriophage, a bacteriophage cocktail, and/or a pharmaceutical composition comprising a bacteriophage or a bacteriophage cocktail are provided. In some embodiments, a method of treating IBD comprises administering to a subject the KP2 bacteriophage, cocktail, and/or pharmaceutical composition described herein. In some embodiments, a method of treating Crohn's disease comprises administering to a subject the bacteriophage, cocktail, and/or pharmaceutical composition described herein. In some embodiments, a method of treating ulcerative colitis comprises administering to a subject the bacteriophage, cocktail, and/or pharmaceutical composition described herein. In some embodiments, a method of treating IBD associated with primary sclerosing cholangitis comprises administering to a subject the bacteriophage, cocktail, and/or pharmaceutical composition described herein. In some embodiments, IBD may be associated with proton pump inhibitor therapy, and a subject may be administered the bacteriophage, cocktail, and/or pharmaceutical composition described herein before, during, or after proton pump inhibitor therapy.

In some embodiments, the bacteriophage, the bacteriophage cocktail, and/or the pharmaceutical composition thereof may be used in a method of treatment. In some embodiments, the bacteriophage and/or the pharmaceutical composition thereof to be administered comprises bacteriophage selected from at least three of the following groups: Group 1, Group 2, Group 3, Group 4, Group 5, and Group 6 as described herein. In some embodiments, the bacteriophage and/or the pharmaceutical composition thereof to be administered comprises bacteriophage selected from at least four of the following groups: Group 1, Group 2, Group 3, Group 4, Group 5, and Group 6 as described herein. In some embodiments, the bacteriophage and/or the pharmaceutical composition thereof to be administered comprises at least one bacteriophage selected from Group 1, Group 5, and Group 6 and at least one bacteriophage selected from Group 2, Group 3, and Group 4 as described herein.

In some embodiments, the bacteriophage and/or the pharmaceutical composition thereof to be administered comprises bacteriophage selected from at least three of the following groups: Group A, Group B, Group C, Group D, Group E, Group F, and Group H, as described herein. In some embodiments, the bacteriophage and/or the pharmaceutical composition thereof to be administered comprises bacteriophage selected from at least four of the following groups: Group A, Group B, Group C, Group D, Group E, Group F, and Group H, as described herein. In some embodiments, the bacteriophage and/or the pharmaceutical composition thereof to be administered comprises at least one bacteriophage selected from Group A, Group E, Group F, Group G, and Group H and at least one bacteriophage selected from Group B, Group C, and Group D as described herein.

In some embodiments, the bacteriophage and/or the pharmaceutical composition thereof to be administered comprises bacteriophage selected from at least three or four bacteriophage that in toto lyse: (a) *Klebsiella pneumoniae* strain KP2; (b) a mutant *Klebsiella pneumoniae* strain KP2 that is characterized by a mutation in a gene involved in synthesizing LPS; (c) a mutant *Klebsiella pneumoniae* strain KP2 that is characterized by a mutation in a gene involved in iron uptake; (d) a mutant *Klebsiella pneumoniae* strain KP2 that is characterized by at least one of a mutation in a gene involved in cobalamin uptake or a mutation in a gene involved in maltose transport. In some embodiments, the bacteriophage and/or the pharmaceutical composition thereof to be administered comprises bacteriophage selected from at least one bacteriophage that infects and/or lyses (a) *Klebsiella pneumoniae* strain KP2; and at least one, two, or three bacteriophage that in toto lyse (b) a mutant *Klebsiella pneumoniae* strain KP2 that is characterized by a mutation in a gene involved in synthesizing LPS; (c) a mutant *Klebsiella pneumoniae* strain KP2 that is characterized by a mutation in a gene involved in iron uptake; (d) a mutant *Klebsiella pneumoniae* strain KP2 that is characterized by at least one of a mutation in a gene involved in cobalamin uptake or a mutation in a gene involved in maltose transport. In some embodiments, the bacteriophage and/or pharmaceutical composition is further capable of lysing KP2 and at least one, two, three, four, five, or six bacteria selected from CT-141-1, CT-123-1, MKP2_2161_1, MKP2_251_B, MKP2_251_C and 8M-all. In some embodiments, the bacteriophage and/or pharmaceutical composition is further capable of lysing each of KP2, CT-141-1, CT-123-1, MKP2_2161_1, MKP2_251_B, MKP2_251_C and 8M-all. In some embodiments, the bacteriophage and/or pharmaceutical composition is further capable of lysing each of KP2, CT-141-1, CT-123-1, MKP2_2161_1, MKP2_251_B, MKP2_251_C and 8M-all.

In some embodiments, the bacteriophage and/or the pharmaceutical composition thereof to be administered comprises bacteriophage selected from at least three or four bacteriophage that in toto lyse: (a) *Klebsiella pneumoniae* strain KP2; (b) a mutant *Klebsiella pneumoniae* strain KP2 that is characterized by a mutation in one or more of rfaQ and grcA genes; (c) a mutant *Klebsiella pneumoniae* strain KP2 that is characterized by a mutation in one or more of rfaG, wbaP, and tyrosineK genes; (d) a mutant *Klebsiella*

*pneumoniae* strain KP2 that is characterized by a mutation in one or more of mfpsA, wecA, and fhuA genes; (e) a mutant *Klebsiella pneumoniae* strain KP2 that is characterized by a mutation in one or more of fepA, tonB and LamB genes; (f) a mutant *Klebsiella pneumoniae* strain KP2 that is characterized by a mutation in a HBAD gene; and (g) a mutant *Klebsiella pneumoniae* strain KP2 that is characterized by a mutation in a 1pxM gene. In some embodiments, the bacteriophage and/or the pharmaceutical composition thereof to be administered comprises bacteriophage selected from at least one bacteriophage that infects and/or lyses (a) *Klebsiella pneumoniae* strain KP2; and at least one, two, or three bacteriophage that in toto lyse (b) a mutant *Klebsiella pneumoniae* strain KP2 that is characterized by a mutation in one or more of rfaQ and grcA genes; (c) a mutant *Klebsiella pneumoniae* strain KP2 that is characterized by a mutation in one or more of rfaG, wbaP, and tyrosineK genes; (d) a mutant *Klebsiella pneumoniae* strain KP2 that is characterized by a mutation in one or more of mfpsA, wecA, and fhuA genes; (e) a mutant *Klebsiella pneumoniae* strain KP2 that is characterized by a mutation in one or more of fepA, tonB and LamB genes; (f) a mutant *Klebsiella pneumoniae* strain KP2 that is characterized by a mutation in a HBAD gene; and (g) a mutant *Klebsiella pneumoniae* strain KP2 that is characterized by a mutation in a 1pxM gene. In some embodiments, the bacteriophage and/or pharmaceutical composition is further capable of lysing KP2 and at least one, two, three, four, five, or six bacteria selected from CT-141-1, CT-123-1, MKP2_2161_1, MKP2_251_B, MKP2_251_C and 8M-all. In some embodiments, the bacteriophage and/or pharmaceutical composition is further capable of lysing each of KP2, CT-141-1, CT-123-1, MKP2_2161_1, MKP2_251_B, MKP2_251_C and 8M-all. In some embodiments, the bacteriophage and/or pharmaceutical composition is further capable of lysing each of KP2, CT-141-1, CT-123-1, MKP2_2161_1, MKP2_251_B, MKP2_251_C and 8M-all.

In some embodiments, the bacteriophage and/or the pharmaceutical composition thereof to be administered comprises bacteriophage that in toto lyse at least three, four, five, or six bacteria selected from (a) a mutant *Klebsiella pneumoniae* strain KP2 that is characterized by a mutation in a rfaQ gene; (b) a mutant *Klebsiella pneumoniae* strain KP2 that is characterized by a mutation in a grcA gene; (c) a mutant *Klebsiella pneumoniae* strain KP2 that is characterized by a mutation in a rfaG gene; (d) a mutant *Klebsiella pneumoniae* strain KP2 that is characterized by a mutation in a wbaP gene; (e) a mutant *Klebsiella pneumoniae* strain KP2 that is characterized by a mutation in both a tyrosineK and a wbaP gene; (f) a mutant *Klebsiella pneumoniae* strain KP2 that is characterized by a mutation in a wecA gene; (g) a mutant *Klebsiella pneumoniae* strain KP2 that is characterized by a mutation in a mfps gene; (h) a mutant *Klebsiella pneumoniae* strain KP2 that is characterized by a mutation in both a fhuA and a wecA gene; (i) a mutant *Klebsiella pneumoniae* strain KP2 that is characterized by a mutation in a fepA gene; (j) a mutant *Klebsiella pneumoniae* strain KP2 that is characterized by a mutation in both a tonB gene and a LamB gene; (k) a mutant *Klebsiella pneumoniae* strain KP2 that is characterized by a mutation in a HBAD gene; (l) a mutant *Klebsiella pneumoniae* strain KP2 that is characterized by a mutation in a 1pxM gene; and (m) a mutant *Klebsiella pneumoniae* strain KP2 that is characterized by a mutation in a fhuA gene. In some embodiments, the bacteriophage and/or pharmaceutical composition is further capable of lysing KP2 and at least one, two, three, four, five, or six bacteria selected from CT-141-1, CT-123-1, MKP2_2161_1, MKP2_251_B, MKP2_251_C and 8M-all. In some embodiments, the bacteriophage and/or pharmaceutical composition is further capable of lysing each of KP2, CT-141-1, CT-123-1, MKP2_2161_1, MKP2_251_B, MKP2_251_C and 8M-all. In some embodiments, the bacteriophage and/or pharmaceutical composition is further capable of lysing each of KP2, CT-141-1, CT-123-1, MKP2_2161_1, MKP2_251_B, MKP2_251_C and 8M-all.

In some embodiments, the bacteriophage and/or the pharmaceutical composition thereof to be administered comprises bacteriophage Mcoc-5c and 8M-7. In some embodiments, the bacteriophage and/or the pharmaceutical composition thereof to be administered comprises bacteriophage Mcoc-5c and 8M-7; and at least one bacteriophage selected from 1.2-3b, 1.2-2, and 1.2-3s. In some embodiments, the bacteriophage and/or the pharmaceutical composition thereof to be administered comprises bacteriophage Mcoc-5c and 8M-7; at least one bacteriophage selected from 1.2-3b, 1.2-2, and 1.2-3s; and at least one bacteriophage selected from KP2-5-1 and PKP-55. In some embodiments, the bacteriophage and/or the pharmaceutical composition thereof to be administered comprises Mcoc-5c, 8M-7, 1.2-2, 1.2-3s. In some embodiments, the bacteriophage and/or the pharmaceutical composition thereof to be administered comprises bacteriophage Mcoc-5c, 8M-7, 1.2-2, 1.2-3b. In some embodiments, the bacteriophage and/or the pharmaceutical composition thereof to be administered comprises bacteriophage Mcoc-5c, 8M-7, KP2-5-1, 1.2-3s, PKP-55. In some embodiments, the bacteriophage and/or the pharmaceutical composition thereof to be administered comprises bacteriophage consisting of Mcoc-5c, 8M-7, 1.2-2, 1.2-3s. In some embodiments, the bacteriophage and/or the pharmaceutical composition thereof to be administered comprises bacteriophage consisting of Mcoc-5c, 8M-7, 1.2-2, 1.2-3b. In some embodiments, the bacteriophage and/or the pharmaceutical composition thereof to be administered comprises bacteriophage consisting of Mcoc-5c, 8M-7, KP2-5-1, 1.2-3s, PKP-55.

In some embodiments, the bacteriophage and/or the pharmaceutical composition thereof to be administered comprises bacteriophage 1.2-3b, 1.2-2, and 1.2-3s. In some embodiments, the bacteriophage and/or the pharmaceutical composition thereof to be administered comprises bacteriophage 1.2-3b, 1.2-2, 1.2-3s, and Mcoc-5c. In some embodiments, the bacteriophage and/or the pharmaceutical composition thereof to be administered comprises bacteriophage 1.2-3b, 1.2-2, 1.2-3s, and 8M-1. In some embodiments, the bacteriophage and/or the pharmaceutical composition thereof to be administered comprises bacteriophage 1.2-3b, 1.2-2, 1.2-3s, Mcoc-5c, and 8M-1.

In some embodiments, the bacteriophage and/or the pharmaceutical composition thereof to be administered is capable of lysing at least one, two, three, four, five, six or seven bacteria selected from KP2, CT-141-1, CT-123-1, MKP2_2161_1, MKP2_251_B, MKP2_251_C, and 8M-all. In some embodiments, the bacteriophage and/or the pharmaceutical composition thereof to be administered is capable of lysing KP2 and at least one bacteria, at least two bacteria, at least three bacteria, at least four bacteria, at least five bacteria, or at least six bacteria selected from CT-141-1, CT-123-1, MKP2_2161_1, MKP2_251_B, MKP2_251_C and 8M-all. In some embodiments, the bacteriophage and/or the pharmaceutical composition thereof to be administered is capable of lysing each of KP2, CT-141-1, CT-123-1, MKP2_2161_1, MKP2_251_B, MKP2_251_C and 8M-all.

In some embodiments, a method of treating IBD comprises administering to a mammal determined to be infected with *Klebsiella* bacteria the bacteriophage, the bacteriophage cocktail, and/or the pharmaceutical composition comprising a bacteriophage or a bacteriophage cocktail described herein. In some embodiments, a method of treating IBD comprises administering to a mammal determined to be infected with *Klebsiella pneumoniae* bacteria the bacteriophage, the bacteriophage cocktail, and/or the pharmaceutical composition comprising a bacteriophage, or a bacteriophage cocktail described herein. In some embodiments, a method of treating IBD comprises administering to a mammal determined to be infected with *Klebsiella pneumoniae* KP2 mutant the bacteriophage, the bacteriophage cocktail, and/or the pharmaceutical composition comprising a bacteriophage, or a bacteriophage cocktail described herein.

In some embodiments, the bacteriophage and the method of treatment is used prophylactically. For example, the method comprises administering to a mammal determined to be susceptible to IBD the bacteriophage, the bacteriophage cocktail, and/or the pharmaceutical composition comprising a bacteriophage or a bacteriophage cocktail described herein.

In some embodiments, susceptibility to IBD is measured by the genetic susceptibility to acquire IBD, as determined by the presence of mutations in the genes or loci associated with the immune function in the intestine including loci and genes involved in inflammation and immunoregulation, tissue remodeling, tumorigenesis and apoptosis (for example, NOD2, HLA-27, ATG16L1, interleukins, CCL and CCR genes, SOD genes, MMPs, JAK, STAT, TIMP genes and many others as described in Suzuki et al., 2012) and genes associated with autophagy (Jostins et al., 2012); presence of other immune conditions (sibling diseases) such as autoimmune disorder, Behcet's disease, graft versus host disease, systemic lupus erythematosus, dermatomyositis, polymyositis, auto-immune chronic active hepatitis, pemphigus vulgaris, polyarteritis nodosa, auto-immune hemolytic anaemia, idiopathic thrombocytopenic purpura, myasthenia gravis, lupus nephritis, platelet transfusion refractoriness type 1 diabetes, ankylosing spondylitis, multiple sclerosis, psoriasis, psoriatic arthritis, asthma, and rheumatoid arthritis (Suzuki et al., 2012); acute gastroenteritis (Raposo et al., 2017); dietary constituents that have been shown to affect the immune response and the inflammatory status, through the modulation of the microbiota, for example high carbohydrate and animal fat diet, high intake of red meat and processed meat, protein, alcoholic beverages, sulfur, and sulfate, processed food (Raposo et al., 2017); lifestyle habits (Western hygiene standards and improved sanitary conditions); medications (antibiotics and steroids) especially when used in childhood leading to the alterations in the microbiome composition (Raposo et al., 2017); epigenetic mechanisms dependent on the nutrients e.g. folates and selenium (DNA methylation (Raposo et al., 2017); pollutants, sedentary lifestyle and tobacco-smoking (Raposo et al., 2017); geography (Hold at al., 2014); history of the IBD in the family (Baumgart and Sandborn, 2012; Neurath, 2014).

In some embodiments, the bacteriophage is administered more than once to achieve a desired therapeutic effect. For example, when a host bacterium is destroyed, the bacteriophage that infected said bacterium can no longer multiply because its host has been eradicated and may be eliminated from the digestive tract, and the bacteriophage may need to be re-administered, e.g., at least twice daily, at least daily, at least every other day, at least every three days, at least weekly, or at least monthly.

In some embodiments, the phage described herein may be administered in combination with one or more known and suitable medicaments for IBD, including anti-inflammatory drugs, dietary therapy, probiotics, etc. In some embodiments, the phage described herein may be administered in combination with one or more substances for modulating the pH of the stomach, e.g., a proton pump inhibitor, a histamine H2 antagonist, and/or bicarbonate.

The medicament or substance for modulating the pH of the stomach may be administered prior to, concurrently with, or after administration of the phage.

Methods of Determining a Subject to be Treated with Phage

Methods of selecting subjects that are responsive to treatment are provided herein.

In some embodiments, the method of selecting a subject that is responsive to treatment by the methods set forth herein comprises (1) obtaining a biological sample, e.g., from the intestine or mouth of the subject, (2) culturing the bacteria obtained from the biological sample, (3) inoculating the cultured bacteria with a bacteriophage described herein, and (4) determining the amount of cultured bacteria that are lysed by the bacteriophage. In some embodiments, the lysis is determined by a liquid media assay and/or a solid media assay as described herein. In some embodiments, the amount of lysis using the bacteria cultured from the intestinal sample is compared to a control, e.g., a sample obtained from a different, uninfected subject or a sample from the same subject prior to infection. In some embodiments, the phage described herein is suitable for treating KP infection if any lysis is mediated by the phage in vitro and/or in vivo. In some embodiments, a subject is determined to be infected with *Klebsiella* if a detectable portion of bacteria cultured from the subject are lysed by the bacteriophage. In some embodiments, a subject is determined to be infected with *Klebsiella* pneumoniaeKP2 if a detectable portion of the cultured bacteria are lysed by a KP2 bacteriophage.

In some embodiments, the biological sample is an oral sample or expectorate, a biopsy, or stool. In some embodiments, determining the amount of cultured bacteria that are lysed by the bacteriophage comprises performing a KP2-specific qPCR of the bacterial sample and/or a direct test for phage sensitivity using the plaque assay or liquid OD method described herein. In some embodiments, a positive sample or subject to be treated is determined by the presence of plaque in a plaque assay. In some embodiments, a positive sample or subject to be treated is determined by a reduction in OD in a liquid OD assay. In some embodiments, serotype-based screening is performed using an assay, e.g., an immunoassay, an ELISA, to determine the presence of antibodies against KP2 and/or their capsular types. In some embodiments, the phage is labeled with a detectable marker, e.g., a luminescent marker, and the infection of the bacteria is determined by detecting an increase in the marker, e.g., in a luminescence assay.

Deposit Accession Numbers

Deposits at The Leibniz Institute DSMZ-German Collection of Microorganisms and Cell Cultures GmbH, and The Polish Collection of Microorganisms (PCM): KP2 bacteria (ACCESSION NO. DSM 33048, deposited on Feb. 27, 2019), KP2-Mcoc1 bacteria (ACCESSION NO. DSM 33049, deposited on Feb. 27, 2019), KP2 8M-all bacteria (ACCESSION NO. DSM 33050, deposited on Feb. 27, 2019), CT-123-1 bacteria (ACCESSION NO. DSM 33051, deposited on Feb. 27, 2019), CT-141-1 bacteria (ACCESSION NO. DSM 33052, deposited on Feb. 27, 2019), MKP2_251B bacteria (ACCESSION NO. DSM 33053, deposited on Feb. 27, 2019), MKP2_251C bacteria (AC- CESSION NO. DSM 33054, deposited on Feb. 27, 2019), MKP2_2161_1 bacteria (ACCESSION NO. DSM 33055, deposited on Feb. 27, 2019), 8M-1 bacteriophage (ACCESSION NO. DSM 33072, deposited on Feb. 27, 2019), 8M-8 bacteriophage (ACCESSION NO. DSM 33071, deposited on Feb. 27, 2019), 8M-7 bacteriophage (ACCESSION NO. DSM 33070, deposited on Feb. 27, 2019), MCoc5c bacteriophage (ACCESSION NO. DSM 33069, deposited on Feb. 27, 2019), 1.2-2 bacteriophage (ACCESSION NO. DSM 33068, deposited on Feb. 27, 2019), KP2-5-1 bacteriophage (ACCESSION NO. DSM 33067, deposited on Feb. 27, 2019), 1.2-3b bacteriophage (ACCESSION NO. DSM 33066, deposited on Feb. 27, 2019), 1.2-3s bacteriophage (ACCESSION NO. DSM 33065, deposited on Feb. 27, 2019), PKP-55 bacteriophage (ACCESSION NO. DSM 33064), colon-11 bacteriophage (ACCESSION NO. F/00143, deposited on Feb. 26, 2020), colon-14-15 bacteriophage (ACCESSION NO. F/00144, deposited on Feb. 26, 2020), KP2-15-2-1 bacteriophage (ACCESSION NO. F/00145, deposited on Feb. 26, 2020), MCoc8a bacteriophage (ACCESSION NO. F/00146, deposited on Feb. 26, 2020), MCoc9-1c bacteriophage (ACCESSION NO. F/00147, deposited on Feb. 26, 2020).

EXAMPLES

Example 1: Isolation of KP2 Clinical Variants

10 µl of stool suspended in buffer was cultured in 4 ml Pepton water (M028, Hylabs) overnight at 37° C. 10 µl of the culture was streaked onto MacConkey and Chromagar orientation plates. Colonies with the ability to grow on the MacConkey plate which presented a pink, mucoid colony morphology or with the ability to grow on the Chromagar plate and with a blue appearance, were tested for motility and ability to form indole gas using UMI agar tubes (TT-147, Hylabs). Colonies were further analyzed by full genome Nextera-based sequencing using next generation paired-end Illumina technology and the resultant sequences were analyzed as detailed below. Each *Klebsiella pneumoniae* isolate was sequenced using Illumina Nextera sequencing of 150 bp paired-end reads.

Adapter removal and quality trimming was done using Trimgalore and cutadapt (Martin, 2011). Positions with phred scores below 30 were deleted from a read and reads shorter than 55 bp after removing low quality nucleotides were discarded entirely. Assembly was performed using SPAdes (Bankevich et al., 2012). Validation of *K. pneumoniae* taxonomy was done using Kleborate which genotypes assemblies and determines whether they are indeed *K. pneumoniae*. Results were obtained by comparing the contigs of an assembly to known *klebsiella* species genomes hosted at: bigsdb.pasteur. Comparisons were done using BLAST (Altschul, 1990) and the *Klebsiella* species was determined from a phylogenetic tree derived from identities between known *Klebsiella* species, where the distance metric is mash (Ondov et al., 2016). KP2 variants were positively identified by two separate methods:
  A. Multi-locus sequence type (MLST): *K. pneumoniae* strains that were determined as sequence type 323 (Diancourt et al., 2005) by Kleborate (run with default parameters) were defined as KP2 strains.
  B. Whole-genome similarity to reference KP2 strains: Reference KP2 (see table below) were obtained, and each new KP strain isolated was compared to these references using fastANI (Jain et al., 2018). Isolated strains with FastANI scores of 99.9% or greater compared to any of these reference genomes were defined as KP2 strains.

If either of these conditions (MLST or whole-genome similarity) was fulfilled, the strain was defined as a KP2 clinical variant. When two of the strains isolated and identified in this manner as KP2 clinical variant were tested for their pro-inflammatory activity in wild type mice and IL10 KO mice which spontaneously develop a chronic inflammatory bowel disease as described in Atarashi et. al 2017 for KP2H7 (Atarashi K, et al. Ectopic colonization of oral bacteria in the intestine drives T(H)1 cell induction and inflammation. Science. 358:359-365, 2017), they were found to exhibit TH1 immune activation capabilities (as shown in FIG. 16).

| Reference KP2 sequence |
| --- |
| GenBank BDQR01000001.1 |
| GenBank GCA_002260905.1 |
| BioSample: SAMD00083910 |
| BioProject PRJDB5883 |
| Ectopic colonization of oral bacteria in the intestine drives TH1 cell induction and inflammation (Atarashi et al., 2017) |

The KP2 bacterial genome has been sequenced and is known in the art, see, e.g., GenBank BDQRO1000001.1, GenBank GCA_002260905.1, BioSample: SAMD00083910, BioProject PRJDB5883, and Atarashi et al., Ectopic colonization of oral bacteria in the intestine drives TH1 cell induction and inflammation, Science (2017). When KP2 mutants were obtained, such as in mutant analyses for phage resistant bacteria described below, 16S analysis was performed. Global homology above 98% to reference KP2 16S sequences confirmed that the subsequent strains were pure. See, e.g., NCBI BLAST (Altschul et al. 1997) and the Ribosomal Database Project (Cole et al. 2014). An in-silico 16S PCR was run on the KP2 resulting in amplicons that both NCBI BLAST (Altschul et al. 1997) and the Ribosomal Database Project (Cole et al. 2014) matched to the 16S of *Klebsiella pneumoniae*.

Example 2: Bacteriophage Sources

Sewage was obtained from the National Virology Center at Sheba Hospital. Dental sewage was collected from the dental clinic at Poria Hospital. Fecal samples were provided from healthy donors or IBD patients at Ichilov Hospital. Batches of sewage comprised of 5-6 samples obtained from different places at different times were centrifuged and the supernatant was filtered (Merck Millipore glass fiber prefilters APFD, APFB followed by Express plus PES 47 mm disks 0.45 µm filters) using a vacuum filtration system. During this process 400 mL of 5-6 samples were mixed into one pool. The pooled sewage sample mix was concentrated by the Pellicon filter system (from 2 L to 20 mL). Concentrated sewage sample was filtered with 0.45 µM filter, passed to barcoded tube and stored at 4° C. Thus, each sewage phage isolate in the bank is comprised of phages from 5-6 samples of different geographical origins.

Dental sewage samples of 4-5 different donors were processed in a similar way to regular sewage, except that the starting volume of the batches was lower than 400 mL. Each concentrated dental sewage sample was filtered with 0.45 µM filter, passed to barcoded tube and stored at 4° C.

Fecal samples were processed individually as follows: 5 g of each fecal sample of an individual donor was weighed and inserted into a BagMixer plastic bag together with SM buffer (50 mM Tris, 200 mM NaCl, 10 mM $MgSO_4$, 0.01% Gelatin). The fecal matter was re-suspended by 2 cycles of 2 minutes in a BagMixer 400P stomacher. The resulting suspension was centrifuged, the remaining supernatant was filtered by 0.45 μm filter to remove the bacterial fraction and kept at 4° C.

Example 3: Screening Environmental and Clinical Samples for Phage that Recognize K. pneumoniae 10 dental sewage samples, 41 sewage samples and 70 fecal samples were used to assemble mini-mixes of mostly 3-samples each (total 39 mixes). Screening was performed by applying 10 μL of each mix to a KP2 bacterial lawn, in 48 well plates by drop plaque assay (Bacteriophages methods and protocols MRJ Clokie AM Kropinsky). Plates were incubated for 2-3 hrs (37° C.) in aerobic conditions, after which plaques became visible on the bacterial lawns. One plaque was picked up (using a sterile 20 μL tip) into phage buffer (Tris-HCl pH 7.5 50 mM, NaCl 100 mM, $MgCl_2 \cdot 6H_2O$ 5 mM, $MnCl_2 \cdot 4H_2O$ 0.1 mM in DDW) and re-isolated in the same manner an additional two times for a total of 3 rounds. A single phage, KP2-5, was isolated in this manner.

The above samples were also used to assemble 6-sample mixes (total 21 mixes). 100 μL of each mix was added to a liquid KP2 culture followed by incubating for 3 hrs at 37° C. Following incubation, the tubes were centrifuged, the supernatant was filtered by 0.45 μm syringe filter and tubes were kept at 4° C. Screening of the supernatants was performed by testing 10 μL of each on KP2 bacterial lawns in 48 well plates by drop plaque assay. Plates were incubated for 2-3 hrs at 37° C., at aerobic conditions, after which plaques became visible on the bacterial lawn. Plaques were picked up (using a sterile 20 μL tip) into phage buffer and re-isolated as detailed above. The phage isolated in this manner are KP2-5-1, KP2-14. KP2-15-1, KP2-15-2-1 and KP2-16-1.

Following accumulation of additional environmental and clinical samples, another round of phage isolation was carried out as described above. 19 dental sewage, 58 sewage and 100 fecal samples were used to assemble 65 mini-mixes (average of three samples per mini-mix) that were afterwards combined to 8 mega mixes (8 mini-mixes=mega mix). 100 μL of each mix was added to a liquid KP2 culture and the supernatants obtained as above.

Supernatants were used for screening via plate reader as follows: 0.2 mL of KP2 (OD=1.2) was dispensed into a 96 well plate. 10 uL of the supernatants were added in duplicates (8×2). Control wells (KP2 with no phage; blank wells) were also prepared. The plate was incubated overnight at 37° C. with agitations in a robotic plate reader (Freedom EVO 75, Tecan) and OD was measured every 15 minutes.

For supernatants which showed a decrease in the growth curve of KP2 (4 out of the 8 mega mixes), screening was performed by testing 10 μL of each supernatant on KP2 bacterial lawns by drop plaque assay. Plates were incubated overnight at 37° C., in aerobic conditions, after which plaques became visible on the bacterial lawn and were isolated as above. The following phage were isolated in this manner: 1.2-2, 1.2-3b, 1.2-3s, 1.2-4br, 1.2-4s.

Example 4: Generating KP2 Mutants

In order to derive resistant mutant strains, KP2 was cultured with KP2-16-1 alone or a cocktail of KP2-5-1, KP2-14. KP2-15-1, KP2-15-2-1 and KP2-16-1, at phage titers of $1 \times 10^6$ PFU/mL in 4 mL BHIS, at 37° C. with shaking to OD600 nm=1.5. Then the culture was diluted with liquid BHIS to OD=0.2 and dispensed (200 μL/well) into 96 wells plate. A volume of 10 μL of KP2-16-1 or the cocktail was added. Absorbance (600 nm) was monitored in a plate reader every 15 min for 24 hrs. as above. Analysis of the growth curves of KP2 alone, or KP2 exposed to KP2 16-1, or to cocktail, revealed mutant candidates. The contents of the wells containing mutant candidates were plated on BHIS agar plates and incubated overnight at 37° C. Single colonies were isolated and propagated in liquid BHIS. The candidates were verified as Klebsiella pneumoniae by 16S and whole genome sequencing analysis as detailed above followed by confirmation of resistance to the respective phages by drop assay. The resistant mutant strains generated in this way are MKP2_2161_1 following exposure to KP2-16-1 and KP2-Mcoc1 following exposure to the cocktail. Mutant strains underwent whole genome sequencing.

Example 5: Isolation of Phage to Resistant Mutants

To isolate phages capable of infecting the resistant KP2 mutants, MKP2_2161_1 and KP2-Mcoc1, 19 dental sewage, 58 sewage and 100 fecal samples were used to assemble 7-9 sample mixes (total 19 mixes). Mixes were cultured with each of the mutants for 3 hours at 37° C. and supernatants obtained by centrifuging and filtering with 0.0.45 μm syringe filter, following which they were kept at 4° C. Screening of supernatants was performed by testing 10 μL on KP2, MKP2_2161_1 and KP2-Mcoc1 bacterial lawns, using 48 well plates by drop plaque assay. Plates were incubated for 2-3 hours at 37° C., at aerobic conditions, after which plaques became visible on bacterial lawn and were isolated.

The phage isolated in this manner are: M16-3-2c, M16-4a, MCoc3c, MCoc5c, KP2-4a, MCoc4c, M16-5c, KP2-5a, KP2-5, M16-6c, MCoc6c, KP2-7c, KP2-7-1c, M16-7a, KP2-8c, KP2-8a, MCoc8a, M16-9-1c, MCoc9-1c, MCoc9-2c, KP2-9a, M16-9a, MCoc15c and Mcoc7c.

8M-all is a KP2 phage resistant mutant that was isolated in the in vivo study of Example 16. The mutant was resistant to all the KP2 phages previously isolated.

A bacterial culture of 8M-all was diluted 1:100 in liquid BHIS supplemented with 1 mM final concentration MMC ($Mg^{2+}$, $Mn^{2+}$, $Ca^{2+}$ ions and divided into a 24-well plate (1 mL in each well). 50 μL from a combined sewage sample originating in 8 individual sewage samples was added, and the samples were incubated overnight at 37° C. Next, 200 μL of each sample was transferred to a 96-well filter plate, and centrifuged for 10 min at 4500×g. A drop plaque assay was performed by testing 5 μL of each supernatant on an 8M-all bacterial lawn grown on a BHIS agar petri plate. Plates were incubated overnight at 37° C. in aerobic conditions, after which plaques became visible and were isolated as above. The phage isolated in this manner are 8M-1, 8M-7 and 8M-8.

Example 6: Phage Amplification and Determination of Phage Titers

Phage were amplified from liquid broth or from soft agar by double agar overlay plaque assay. Amplification from liquid broth was performed by diluting 50 μL of isolated phage sample into 4 mL log phase host culture at OD=1.7, or into 4 mL log phase culture at OD=0.5, and incubating at 37° C., overnight. Tubes were centrifuged, the supernatant was filtered by 0.45 μm syringe filter, and 1 mM of the divalent ions $Ca^{2+}$ and $Mg^{2+}$ were added.

Phage titers were determined by drop plaque assay as follows: host culture was prepared by inoculating 4 mL liquid BHIS (BACTOTM Brain Heart Infusion BHI, Yeast extract 0.5% and Resazurin) with 5-10 colonies of the host and incubating at 37° C., until OD was 1.7 (1.5-2 hrs). 100 μL of host culture were added to 4 mL of molten top agar (BHIS top agar: BHIS media, 0.4% Agarose) with divalent ions $Ca^{2+}$ and $Mg^{2+}$ and dispensed (100 μL/well) to 48 well plate with underlay of bottom agar (BHIS bottom agar: BHIS media, 1.6% Agarose). Plate was incubated for 30 minutes (37° C.), and then dilutions of phage sample were dropped (10 μL). Plate was incubated for 2-3 hrs before counting plaques (10-50 plaques) and determination of phage titer (number of plaques×10× reciprocal of counted dilution=PFU/mL).

Amplification of phage from soft agar was performed in cases where titers of phage that were produced from liquid BHIS were lower than $1\times10^9$ PFU/mL. Log phase host culture at OD=1.7, was diluted to OD=1, and aliquots of 100 μL diluted host culture were added to 100 μL of phage at a titer that is sufficient to result in production of confluent plaques, and incubated at room temperature for 15 minutes. Then each host-phage mixture was diluted with 3 mL soft molten agar and poured on top of BHIS bottom agar. Plates were left to harden, and then incubated at 37° C. for 2-3 hrs or until complete lysis. Plates were scraped from the top agar with a spreader and agar was transferred to sterile tubes with BHIS and 10 μL of chloroform. Tubes were left to stand for 30 minutes to enable phage to elute from the soft agar. Tubes were centrifuged, and supernatant was filtered with 0.45 μM syringe filter to eliminate residual agar. Divalent ions $Ca^{2+}$ $Mg^{2+}$ at concentration of 1 mM were added to tubes which were stored at 4° C.

Example 7: Host Range Analysis of Initially Isolated Phage

Host range analysis for phage isolated on KP2, as well as for the commercial phage (ATCC 23356-B1) was performed on six *K. pneumoniae* strains from ATCC: BAA-2552 (KP1), 23356 (KP4), 13882 (KP5), BAA-1705 (KP6), 700603 (KP7) and 700721 (KP8). Each phage was added (10 μL) to bacterial lawns of the *K. pneumoniae* strains in 48 well plates by drop assay. Plates were incubated for 2-3 hrs (37° C.) in aerobic conditions, after which plaques became visible on the bacterial lawns. Plates with bacterial lawns of KP2 and their respective phage served as positive control. Host range was performed for each of the phage with two phage titers; $1\times10^6$ PFU/mL and $1\times10^9$ PFU/mL.

Results of the host range analysis are presented in FIG. 15, where "S" (dark gray) indicates susceptibility (10 plaques or more to full clearing) and "R" (light gray) indicates resistance (less than 10 plaques). All phages exhibited high specificity to the corresponding hosts on which they were isolated with. This was the case for both titers tested. The exception to this observation was for phage KP2-5-1 which infected 23356 strain when applied at a high titer of $1\times10^9$ PFU/mL, however no plaques were observed for KP2-5-1 on 23356 at a lower titer of $1\times10^6$ PFU/mL.

Thus, it was shown that phages isolated on KP2 host bacteria are specific to their host, recognizing specific receptors/attachment sites expressed by this bacterial strain. Moreover, the commercial phage ATCC 23356-B1 did not recognize KP2, but only the strain KP4 on which it was isolated, suggesting a it recognizes different host receptors/attachment sites.

Example 8: Isolation of Phage to KP2 Clinical Variants

In order to obtain phage that target KP2 as well as the KP2 clinical variants that were isolated and the resistant mutant KP2 strains, sewage samples were sequentially exposed to these different targets. A combined sewage sample originating from 50 individual samples was inoculated with $10^3$ total PFU of phages (1.2-2, 1.2-3b, 1.2-3s, KP2-7-1c and MCoc5c), and filtered through a 0.45 μm PES syringe filter. The filtrate was stored at 4° C. until use.

Bacterial strain KP2 was cultured in 5 mL BHIS supplemented with 1 mM $Ca^{2+}$, $Mg^{2+}$ and $Mn^{2+}$ ions (MMC ions), at 37° C., until OD of 0.2-0.4. To this, 0.5 mL of the combined sewage sample filtrate was added and incubated for 4 hrs. Next, the culture was centrifuged at 4500×g for 5 minutes at room temperature and filtered using a 0.45 μm PES syringe filter.

The resulting supernatant was exposed to a mix of 14 KP2 clinical variants isolated from stool as described in Example 1 and the 2 mutant strainsMKP2_2161_1 and KP2-Mcoc1 following which it was once again centrifuged and filtered for testing on a KP2 lawn. Plaques which appeared were isolated as described above. This process led to isolation of PKP-55.

Example 9: Phage Isolation on Tissues

KP2 colonized colon tissues were obtained from the in vivo animal studies described in Examples 15, 16 and 17. Phage that infect KP2 colonized tissues were isolated in one of two ways:
A) Three KP2 colonized colon tissue segments, from three mice, were chopped and placed together into 40 mL of phage buffer (50 mM Tris-HCl, 100 mM NaCl, 5 mM $MgCl_2$, 0.1 mM $MnCl_2$ PH=7.5) with 40 μL of 1M MMC ions and 4 mL of liquid BHIS. The solution was divided into a 48-well plate (1 mL at each well). 30 sewage samples were tested. 10 μL of each sewage sample was added to individual wells, and the samples were incubated at 37° C. After 2 and 6 h of incubation, 100 μL from each well was transferred to 96-well filter plate and centrifuged for 10 min at 4500×g. Drop plaque assay was performed by testing 5 μL of each supernatant on a KP2 bacterial lawn. Plaques were isolated as described above. Phage isolated in this manner are colon1, colon-6, colon-36 and colon-14-15.
B) 66 sewage samples, 24 dental sewage samples and 57 clinical stool samples were combined, resulting in 48 mixes. Five colon segments from five mice colonized with KP2 were cut horizontally in an anaerobic chamber and washed in petri dishes filled with PBS. The colons were chopped into 96 pieces that were distributed into two 96 well plates. Plates with colon pieces were centrifuged for 5 min at 300×g, excess PBS was removed and 50 μL of the phage containing mixes plus MMC ions was added. 200 μL of BHIS +2 mM MMC ions were then added to one of the two plates that was then incubated at 37° C. After 3 and 6 hours, 50 μL of supernatant was obtained from each sample of one the two duplicate plates by filtering with a 0.45 um 96-well filter plate and centrifuging for 10 min at 4500×g.

For the remaining plates, the phage containing mix was removed after 45 minutes by centrifuging for 5 min at 300×g., carrying out a PBS wash and adding 200 µL of BHIS+1 mM MMC ions to each well. After incubation at 37° C. for 6 hours, 50 µL of each sample was filtered by transferring into a 0.45 um 96-well filter plate which was centrifuged for 10 min at 4500×g.

All supernatants obtained as described above were applied on a KP2 bacterial lawn to obtain plaques that were picked into 100 µL phage buffer (Tris-HCl pH 7.5 50 mM, NaCl 100 mM, $MgCl_2 \cdot 6H_2O$ 5 mM, $MnCl \cdot 4H_2O$ 0.1 mM in DDW) and re-isolated, as described above, a total of 3 times to ensure phage purity. Phage isolated in this manner are colon-11 and colon-14.

Example 10: Phage Taxonomy

Bacteriophages were sequenced and reads assembled using SPAdes 3.9.0. (Bankevich et al., 2012). Prediction of open reading frames and translation to amino acid sequences was performed on all assembled phage genomes using Prokka version 1.13.3. (Seemann 2014). Three approaches were used to taxonomically classify each phage:
1) Phage structural genes were analyzed using VIRFAM. See, e.g., Lopes et al. 2014. VIRFAM clustered these into 3 different families: Myoviridae Type 2 (e.g., phages T4 or RB43), Podoviridae Type 3 (e.g., phages phiYeO3-12, T3 or T7) and Siphoviridae Type 1 (e.g., phages T1, TLS or RTP).
2) Assembled phage genomes were compared to phage genomes in the NCBI Refseq database (O'Leary et al. 2016) with BLAST+version 2.6.0 (Camacho et al. 2009). The cutoff used was 80% identity and 70% query coverage. Taxonomic annotation of the best hit from the BLAST search results was noted.
3) Phage protein sequences were compared to phage proteomes in the NCBI Refseq database (O'Leary et al. 2016) with BLAST+version 2.6.0 (Camacho et al. 2009). The cutoff used was 50% identity and 50% query protein coverage. The reference genome (RF) was determined for each phage by the protein sequences in the BLAST search with highest homology. The taxonomic annotation of the phages was inferred from the taxonomic annotation of the reference genome, in addition to other genomes with over 40% homology to the RE.

Overall the taxonomy annotation obtained by the three methods is consistent. Nonetheless, discrepancies may be resolved by the International Committee on Taxonomy of Viruses (ICTV) specific taxon threshold. The taxonomy annotation is presented in FIG. 1 and the percent homology between phage in the different taxonomic groups and within the groups is shown in FIG. 2.

Example 11: Mechanism of Action—Resistant Mutants Creation

To identify the bacterial cell surface receptors used by different phages, resistant mutant bacteria were isolated and characterized to detect the genomic modifications responsible for the resistance. The putative mechanism of action (MOA) of several bacteriophages was analyzed in a multi-step process involving infection of KP2, KP2-Mcoc1 and 8M-all, followed by selection and sequencing of resistant mutants. Differences between pre-infection and mutated DNA were analyzed to determine the phage infection mechanism (Avrani et al., 2011).

For each phage-host pair, frozen samples of host were thawed from −80° C. stock, plated on BHIS agar plates and incubated overnight at 37° C. Next, single colonies were isolated and propagated in liquid BHIS. 0.1 ml of each culture was collected and frozen at −20° C. for DNA extraction (pre-infection DNA). 0.1 ml of $10^9$ PFU/ml of the selected phage was added to 0.1 ml of each culture and the samples were incubated for 15 min at 37° C. to allow phage attachment to host. Next, the samples were added to top agar, plated and incubated overnight at 37° C. Multiple single colonies were isolated from each phage-host combination and resuspended in liquid BHIS. Each sample was divided into two parts, one was frozen at −20° C. for DNA extraction and the other used for mutant validation.

Mutant validation was performed by adding 5 ul of $10^6$ PFU/ml of the relevant phage to a strip containing the host mutant grown in a BHIS plate. Mutant colonies resistant to the selected phage (no plaques observed) were frozen at −80° C. DNA of selected mutant colonies and pre-infection DNA was extracted following the manufacturer's protocol (geneJET Genomic DNA purification Kit, Thermo scientific). Table 2 below shows phage-host combinations used in the procedure described above.

TABLE 2

| phage | host |
| --- | --- |
| 1.2-3s | KP2 |
| 1.2-2 | KP2 |
| 1.2-3b | KP2 |
| colon1 | KP2 |
| MCoc5c | KP2-Mcoc1 |
| 8M-1 | 8M-all |

Example 12: Mechanism of Action—DNA Assembly and Mutations Analysis

Mutant and original bacterial genomes were compared to determine mutations responsible for infection mechanism. The DNA isolated pre-infection was used as an original sample in each biological replicate. Short read sequences of original samples (Illumina 250 paired-end) in combination with minION long reads (MinION; Madoui et al. 2015) were assembled into reference original genomes by Unicycler (Wick et al. 2017).

Mutant DNA and original sequences were compared using the breseq tool (Barrick et al. 2009, Deatherage and Barrick 2014) to identify relevant mutations. Breseq was used in default settings with the polymorphism option, which identifies polymorphism(s) between the mutant and the reference sequence. The discovered genomic modifications are presented in Table 3 below. From this table it can be seen that different phage appear to utilize different surface components for bacterial attachment. Phage utilizing different phage attachment elements are likely to be complementary in their ability to lyse common target bacteria.

TABLE 3

| Bacterial strain (phage to which developed resistance) | Mechanism or Bacterial Surface Component (gene) | Mutant sequence | Original sequence |
|---|---|---|---|
| Colon1_1 11_S83 (colon1) | LPS (rfaQ) | MTPETLSRGPLNPARILVIKLRHH GDMLLITPLIHALKQQYPAASVDV LLYEETRDMLAANPDIHHIYGLDR RWKKQGKRYQLKMQWQLIQTLRQQ RYDMVLNLADQWPSAVISKLTGAA TRIGFDFPKRRHPVWRYCHTALAS TQQHNQLHTVQQNLSILAPLGLQL NDAPARMGYSEADWAASRALLPED FREHYIVIQPTSRWFFKCWREDRM SALINALSAEGYAVVLTSGPDARK KKMVDTIIAGCPQARLHSLAGQLT LRQLAAVIDHARLFIGVDSVPMHM AAALGTPLVALFGPSKLTFWRPWQ AKGEVIWAGDFGPLPDPDAINTNT DERYLDLIPTDAVIAAAKKVLA | MTPETLSRGPLNPARILVIKLRHHGDMLL ITPLIHALKQQYPAASVDVLLYEETRDML AANPDIHHIYGLDRRWKKQGKRYQLKMQW QLIQTLRQQRYDMVLNLADQWPSAVISKL TGAATRIGFDFPKRRHPVWRYCHTALAST QQHNQLHTVQQNLSILAPLGLQLNDAPAR MGYSEADWAASRALLPEDFREHYIVIQPT SRWFFKCWREDRMSALINALSAEGYAVVL TSGPDAREKKMVDTIIAGCPQARLHSLAG QLTLRQLAAVIDHARLFIGVDSVPMHMAA ALGTPLVALFGPSKLTFWRPWQAKGEVIW AGDFGPLPDPDAINTNTDERYLDLIPTDA VIAAAKKVLA |
| Colon1_1 39_S111 (colon1) | LPS(grcA) | MITGIQITKAANDDLLNSFWLLDS EKGEARCLCAKGGFAEDDVVAVSK LGEIEYREIPVDKPEVRVEGGQH LNVNVLRRETL[V/Q]DAVKHPEK YPQLTIRVSGYAVRFNSLTPEQR DVIARTFTESL | MITGIQITKAANDDLLNSFWLLDSEKGEA RCLCAKGGFAEDDVVAVSKLGEIEYREIP VDVKPEVRVEGGQHLNVNVLRRETLLDAV EHPEKYPQLTIRVSGYAVRFNSLTPEQQR DVIARTFTESL |
| Mcoc_5C_1 (MCoc5c) | LPS (rfaG) | MSKFRLALVRQKYRPDGGAERFVS RALEALDSSHLQLNVITREWQGPV KPDWQIHICNPRKWGRISRERGFA NAARELWQRESFDLVQSHERIPGC DLYRAGDGVHRRWLQQRSRILPAW KSRLLFADRYHRYVMQAEREMYED SHLRGVICNAEMIKREIIEDFGLP AEKIHVIYNAIDNQRFLPPDEETF AALRAKWQLPLQATCLIYVGSGFE RKGLAAAIRAIAPTDRYLLVVGKD KDQPRYQALAKSLNCEARVRFFGM QSERLPFYQMADGLLLPTLYDPFP NVILEAMACGLPVITTTGCGGAEF IVDGHNGYVCDALDIPALQQAVMA LPARALGSAEGGHARERIMACTSE RLSTQLLSLYQDLVK | MSKFRLALVRQKYRPDGGAERFVSRALEA LDSSHLQLNVITREWQGPVKPDWQIHICN PRKWGRISRERGFANAARELWQRESFDLV QSHERIPGCDLYRAGDGVHRRWLQQRSRI LPAWKSRLLFADRYHRYVMQAEREMYEDS HLRGVICNAEMIKREIIEDFGLPAEKIHV IYNAIDNQRFLPPDEETFAALRAKWQLPL QATCLIYVGSGFERKGLAAAIRAIAPTDR YLLVVGKDKDQPRYQALAKSLNCEARVRF FGMQSETLPFYQMADGLLLPTLYDPFPNV ILEAMACGLPVITTTGCGGAEFIVDGHNG YVCDALDIPALQQAVMALPARALGSAEGG HARERIMACTSERLSTQLLSLYQDLVK |
| Mcoc_5C_4 (MCoc5c) | LPS (wcaJ or wbaP) | MSRLARNFWTSILLAISDFTGFTV AIVFAIFFVKSFMNDGGHIIANSN INDWVILHTCLGICCVAWYSIRLR HYFYRKTFWFELKEILRTLVIFAI IEIAVLSFAYWDFSRYILAVTWIF VLFFVPTFRMLTKKCLNFLDYGSV KQ | MSRLARNFWTSILLAISDFTGFTVAIVFA IFFVKSFMNDGGHIIANSNINDWVILHTC LGICCVAWYSIRLRHYFYRKTFWFELKEI LRTLVIFAIIEIAVLSFAYWDFSRYILAV TWIFVLFFVPTFRMLIKKCLNFFGLWKRE TIIIGDGNNAVEAWKAINSESNLGFNVTS FVSSTSKDHLKNHINDIPVISLNPKEVTK HFDKRTQFIVALETSESSIRNDWLREFLI NGFRYVSVIPTLRGVPLDSTDMSFIFSHE VMIFRVQQNLAKLSSRILKRLFDIIGSLT IILVSSPLLIYIALKVKKDHGPAIYGHER IGNGGRPFKCLKFRSMVVNSKEVLEQLLN TDPAARKEWDATFKLKDDPRITDIGKFLR KTSLDELPQLFNVLKGEMSLVGPRPIITA ELERYSDEVDYYLLSKPGMTGLWQVSGRS DVDYETRVYLDAWYVKNWSMWNDIAILFK TISVVLRKDGAY |
| Mcoc_5C_7 (MCoc5c) | LPS (tyrosineK) | MSSLKNKPENKDADEIDLSRLYGE LIDHRKLIISVTAFFTLIALVYSL FSTPIYQADSLIQVEQKQANAILS NLSQMLPDSQPQSAPEITLLQSRM ILGKTVDDLNLQAKIKQNYFPILG RGFSRLSGDKPGIINVSRLYLPKT DDDIPELTLTVIDANKFTIQTDSF EAEVKVGELFEKNNISLKVDEIQA KPGTSFTVEYLSKLKAINDLRDVL TVSDQGKDTGMLTLSLTGDDPVQI RKILDSISNNYLMQNIDRQAAQDA KSLEFLNRQLPQVRHDLDISEDKL NKYRQQKDSVDLSLEAKAVLDQIV NVDNQLNELTIRESEVSQHFTKEH PTYKALMEKRVTLLEEKAKLNKRV SAMPETQQEVLRLSRDVDSGRAVY | MSSLKNKPENKDADEIDLSRLYGELIDHR KLIISVTAFFTLIALVYSLFSTPIYQADS LIQVEQKQANAILSNLSQMLPDSQPQSAP EITLLQSRMILGKTVDDLNLQAKIKQNYF PILGRGFSRLSGDKPGIINVSRLYLPKTD DDIPELTLTVIDANKFTIQTDSFEAEVKV GELFEKNNISLKVDEIQAKPGTSFTVEYL SKLKAINDLRDVLTVSDQGKDTGMLTLSL TGDDPVQIRKILDSISNNYLMQNIDRQAA QDAKSLEFLNRQLPQVRHDLDISEDKLNK YRQQKDSVDLSLEAKAVLDQIVNVDNQLN ELTIRESEVSQHFTKEHPTYKALMEKRVT LLEEKAKLNKRVSAMPETQQEVLRLSRDV DSGRAVYMQLLNRQQELNIAKSSAIGNVR VIDEAVTQPRPVAPKKILIVIGGIIFGLI VSVAIIALRVFLRRGIESPEQLEVLGINV |

TABLE 3-continued

| Bacterial strain (phage to which developed resistance) | Mechanism or Bacterial Surface Component (gene) | Mutant sequence | Original sequence |
|---|---|---|---|
| | | MQLLNRQQELNIAKSSAIGNVRVI DEAVTQPRPVAPKKILIVIGGIIF GLIVSVAIIALRVFLRRGIESPEQ LEVLGINVYASIPVSETFAKNITK GLKSNKKKSLEYDEFLAIQNPADL AIEAIRGLRTSLHFAMMEARNNIL MISGASPNAGKTFVSSNLAAIISQ TGKKVLFLDADLRKGYTHKLFNVS NENGLSDYLAGKVDIKNCVKQIKT AGFDFISRGMVPPNPAELLMHSRF QNLLSWASDNYDLVIVDTPPILAV TDAAIIGNYAGTTLLVARF | YASIPVSETFAKNITKGLKSNKKKSLEYD EFLAIQNPADLAIEAIRGLRTSLHFAMME ARNNILMISGASPNAGKTFVSSNLAAIIS QTGKKVLFLDADLRKGYTHKLFNVSNENG LSDYLAGKVDIKNCVKQIKTAGFDFISRG MVPPNPAELLMHSRFQNLLSWASDNYDLV IVDTPPILAVTDAAIIGNYAGTTLLVARF EQNTVKEIEVSAKRFEQSGVMIKGCILNG VVKKASSYYGYGYSHYGYSYSNKE |
| Mcoc_5C_7 (MCoc5c) | LPS (wcaJ or wbaP) | MSRLARNFWTSILLAISDFTGFTV AIVFAIFFVKSFMNDGGHIIANSN INDWVILHTCLGICCVAWYSIRLR HYFYRKTFWFELKEILRTLVIFAI IEIAVLSFAYWDFSRYILAVTWIF VLFFVPTFRMLTKKCLNFFWIMEA | MSRLARNFWTSILLAISDFTGFTVAIVFA IFFVKSFMNDGGHIIANSNINDWVILHTC LGICCVAWYSIRLRHYFYRKTFWFELKEI LRTLVIFAIIEIAVLSFAYWDFSRYILAV TWIFVLFFVPTFRMLTKKCLNFFGLWKRE TIIIGDNNAVEAWKAINSESNLGFNVTS FVSSTSKDHLKNHINDIPVISLNPKEVTK HFDKRTQFIVALETSESSIRNDWLREFLI NGFRYVSVIPTLRGVPLDSTDMSFIFSHE VMIFRVQQNLAKLSSRILKRLFDIIGSLT IILVSSPLLIYIALKVKKDHGPAIYGHER IGNGGRPFKCLKFRSMVVNSKEVLEQLLN TDPAARKEWDATFKLKDDPRITDIGKFLR KTSLDELPQLFNVLKGEMSLVGPRPIITA ELERYSDEVDYYLLSKPGMTGLWQVSGRS DVDYETRVYLDAWYVKNWSMWNDIAILFK TISVVLRKDGAY |
| 1.2-3b_2 27_S99 (1.2-3b) | LPS (mfpsA) | MNGMYSIDSINEIKKSWGDILPQE EMFIFSAAGPTALRDCENHPRSVA ATLARELAIANINPDVVFIINFYE GFDDSYTVSIPQTTVPWKTVCVCH DLIPLLNKERYLGEPNFRQYYYDK LAQYERADAIFAISRSSMQEVIDY TSIPAEKIINISSGVSDSFKIKDY THDEIKDLRNKYHLPQEFILSLAM IEPRKNIEALIHAYSLLPHALQQS YPLVLAYKISTDEKERLYRVAENY GLSRNQLIFTGFLNDSDLIALYNL CKIFVFPSIHEGFGLPPLEAMRCG AATLGSNVTSLPEVIGMEEALFNP LDVPDICRVMQRALTDSEFYSALK AHAPAQAAKFTWDHTAQLALKGFE RLVDKASASEPLDITSFTAHTINR IKNIAELSETERLQTAWAIARNSF ATHQRKLLVDISVLVEHDAKTGIQ RVSRSILSELLKSGVAGYTVSAVY YRPGECYRYANEYLNTHFNGAFGP DVPVLFTKDDILVATDLTAHLFPE LTVQLDFIRLSGAKVCFVVHDILP LRRPEWSDEGMQRVFPIWLSCIAQ HADRLICVSASVAEDVKAWIAENS HWVKPNPLLTVSNFHLGADLDASV PSTGMPDNA | MNGMYSIDSINEIKKSWGDILPQEEMFIF SAAGPTALRDCENHPRSVAATLARELAIA NINPDVVFIINFYEGFDDSYTVSIPQTTV PWKTVCVCHDLIPLLNKERYLGEPNFRQY YYDKLAQYERADAIFAISRSSMQEVIDYT SIPAEKIINISSGVSDSFKIKDYTHDEIK DLRNKYHLPQEFILSLAMIEPRKNIEALI HAYSLLPHALQQSYPLVLAYKISTDEKER LYRVAENYGLSRNQLIFTGFLNDSDLIAL YNLCKIFVFPSIHEGFGLPPLEAMRCGAA TLGSNVTSLPEVIGMEEALFNPLDVPDIC RVMQRALTDSEFYSALKAHAPAQAAKFTW DHTAQLALKGFERLVDKASASEPLDITSF TAHTINRIKNIAELSETERLQTAWAIARN SFATHQRKLLVDISVLVEHDAKTGIQRVS RSILSELLKSGVAGYTVSAVYYRPGECYR YANEYLNTHFNGAFGPDVPVLFTKDDILV ATDLTAHLFPELTVQLDFIRLSGAKVCFV VHDILPLRRPEWSDEGMQRVFPIWLSCIA QHADRLICVSASVAEDVKAWIAENSHWVK PNPLLTVSNFHLGADLDASVPSTGMPDNA QALLAAMAAAPSFIMVGTMEPRKGHAQTL AAFEELWLQGKNYNLFIIGKQGWHVDDLC ERLRHHPQLNKKLFWLQNISDEFLTKLYS QSSALIFASLGEGFGLPLIEAAQKKLPVI IRDIPVFKEIAQEHAWYFSGEAPSDIAKA VEDWLALYEQNAHPRSENINWLTWKQSAE FLLKNLPIIAPAAKQ |
| 1.2-3b_8 29_S101 (1.2-3b) | LPS (wecA) | MNLLTAITELISIFLFTTLFIFVA RKVAKKIGLVDKPNYRKRHQGLIP LVGGISVYAGICFTAIADYYIPH ASLYLACAGVLVLVGALDDRFDIS VKIRAVIQAAIAVIMMMAGNLHLS SLGFIFGSWELVLGPFGFFLTLFA VWAAINAFNMVDGIDGLLGGLSSV SFAATGIILWFDGQYSLAMWCFAM IAAILPYILLNLGALGRRYKVFMG | MNLLTAITELISIFLFTTLFIFVARKVAK KIGLVDKPNYRKRHQGLIPLVGGISVYAG ICFTAIADYYIPHASLYLACAGVLVLVG ALDDRFDISVKIRAVIQAAIAVIMMMAGN LHLSSLGFIFGSWELVLGPFGFFLTLFAV WAAINAFNMVDGIDGLLGGLSSVSFAATG IILWFDGQYSLAMWCFAMIAAILPYILLN LGALGRRYKVFMGDAGSTMIGFTIIWILL ETTQGKTHPISPVTALWIIAIPLMDMVAI |

TABLE 3-continued

| Bacterial strain (phage to which developed resistance) | Mechanism or Bacterial Surface Component (gene) | Mutant sequence | Original sequence |
|---|---|---|---|
| | | DAGSTMIGFTIIWILLETTQGKTH PISPVTALWIIAIPLMDMVAIMYR RLRKGMSPFSPDRQHIHHLIMRAG FTSRQAFVLITLAASPAGAGWRRG GIHPHCAGMGDVNSLFGSLLSLWL LY | MYRRLRKGMSPFSPDRQHIHHLIMRAGFT SRQAFVLITLAAALLALVGVVAETYRIVP EWVMLILFLVAFFLYGYCIKRAWKVARLV KRIRRRIRRHSGNNPKLTK |
| 1.2-3b_7 12_S84 (1.2-3b) | Iron uptake (fhuA) | MARPKTAQPNHSLRKVAAVVATAV SGMSVYAQAAEQPKQEETITVVAA PAAQESAWGPAPTIAAKRSATATK TDTPIEKTPQSVSVVTRQEMEMRQ PTTVKEALSYTPSVFSTRGSSTTY DVVTIRGFTTSTTVNTNQYLDGMK LQGNNYSEVSMDPYFLERVEVMRG PTSVLYGNSNPGGIVSMVSKRPTT EPLKEVQFKMGTDNLWQTGFDFSD AIDDAGVWSYRLTGLGRSQDAQQQ MAKSTRYAVAPSFSWRPDDKTDFT FLSNFQNDPDAGYYGWLPREGTVV PYYDANGKAHKLPTDFNEGESDNK ISRRQKMVGYSFSHQFDDTFTVRQ NLRYADVHTLYRSVYGNGYVAPGY MNRAYVRSDEHLNTFRYPAAV | MARPKTAQPNHSLRKVAAVVATAVSGMSV YAQAAEQPKQEETITVVAAPAAQESAWGP APTIAAKRSATATKTDTPIEKTPQSVSVV TRQEMEMRQPTTVKEALSYTPSVFSTRGS STTYDVVTIRGFTTSTTVNTNQYLDGMKL QGNNYSEVSMDPYFLERVEVMRGPTSVLY GNSNPGGIVSMVSKRPTTEPLKEVQFKMG TDNLWQTGFDFSDAIDDAGVWSYRLTGLG RSQDAQQQMAKSTRYAVAPSFSWRPDDKT DFTFLSNFQNDPDAGYYGWLPREGTVVPY YDANGKAHKLPTDFNEGESDNKISRRQKM VGYSFSHQFDDTFTVRQNLRYADVHTLYR SVYGNGYVAPGYMNRAYVRSDEHLNTFTV DTQLQSDFATGAVSHTLLTGVDYSRMRND VDADYGTADPISMSNPQYGNPNIQVTFPY AVLNRMEQTGLYAQDQMEWDKWVMTLGGR YDYATTSTLTRATNSLAENHDQQFSWRGG INYLFDNGISPYFSYSESFEPVSGSNSRG QPFDPSRGKQYEAGVKYVPKDMPVVTAA VYQLTKDKNLTADPANQAFSIQTGEIRSR GLELEAKAAVNANINVTAAYSYTDAEYTH DTVFNGKRPAEVPRNMASLWADYTFHETA LSGLTIGAGARYIGSTVSYYKNDTSTGKK NDAFSVAGYALMDATVKYDLARFGLPGSS VGVNVNNLFDREYVSSCYSEYACYWGAGR QVVATATFRF |
| | LPS (wecA) | MNLLTAITELISIFLFTTLFIFVA RKVAKKIGLVDKPNYRKRHQGLIP LVGGISVYAGICFTFAIADYYIPH ASLYLACAGVLVLVGALDDRFDIS VKIRAVIQAAIAVIMMMAGNLHLS SLGFIFGSWELVLGPFGFFLTLFA VWAAINAFNMVDGIDGLLGGLSSV SFAATGIILWFDGQYSLAMWCFAM IAAILPYILLNLGALGRRYKVFMG DAGSTMIGFTIIWILLETTQGKTH PISPVTALWIIAIPLMDMVAIMYR RLRKGMSPFSPDRQHIHHLIMRAG FTSRQAFVLITLAASPAGAGWRRG GIHPHCAGMGDVNSLFGSLLSLWL LY | MNLLTAITELISIFLFTTLFIFVARKVAK KIGLVDKPNYRKRHQGLIPLVGGISVYAG ICFTFAIADYYIPHASLYLACAGVLVLVG ALDDRFDISVKIRAVIQAAIAVIMMMAGN LHLSSLGFIFGSWELVLGPFGFFLTLFAV WAAINAFNMVDGIDGLLGGLSSVSFAATG IILWFDGQYSLAMWCFAMIAAILPYILLN LGALGRRYKVFMGDAGSTMIGFTIIWILL ETTQGKTHPISPVTALWIIAIPLMDMVAI MYRRLRKGMSPFSPDRQHIHHLIMRAGFT SRQAFVLITLAAALLALVGVVAETYRIVP EWVMLILFLVAFFLYGYCIKRAWKVARLV KRIRRRIRRHSGNNPKLTK |
| 8M1_1 (8M-1) | Iron uptake (fepA) | MNNRIKSLALLVNLGIYGVAFPLS AAETATDDKNSAAEETMVVTAAEQ NLQAPGVSTITADEIRKRPPARDV SEIIRTMPGVNLTGNSTSGQRGNN RQIDIRGMGPENTLILIDGKPVTS RNSVRLGWRGERDTRGDTSWVPPE IIERIEVIRGPAAARYGNGAAGGV VNIITKKTGDEWRGSWNTYMNAPE HKDEGSTKRTNFSLSGPLGGDFSF RLFGNLDKTQADAWDINQGHQSER TGIYADTLPAGREGVKNKNIDGLV RWEFAPMQSLEFEAGYSRQGNLYA GDTQNTNSNDLVKENYGKETNRLY RNTYSVTWNGAWDNGVTTSNWAQY ERTRNSRKGEGLAGGTEGIFNSNQ FTDIDLADVMLHSEVSIPFDYLVN QNLTGSEWNQQRMKDNASNTQAL SGGEIPGYDSTGRSPYSQAEIFSL FAENNMELTDTTMLTPALRFDHHS IVGNNWSPSLNLSQGLWDDFTLKM GIARAYKAPSLYQTNPNYILYSKG QGCYASKDGCYLQGNDDLKAETSI NKEIGLEFKRDGWLAGVTWFRNDY RNKIEAGYAPVYQNNKGTDLYQWE NVPKAVVEGLEGTLNVPVSETVNW | MNNRIKSLALLVNLGIYGVAFPLSAAETA TDDKNSAAEETMVVTAAEQNLQAPGVSTI TADEIRKRPPARDVSEIIRTMPGVNLTGN STSGQRGNNRQIDIRGMGPENTLILIDGK PVTSRNSVRLGWRGERDTRGDTSWVPPEI IERIEVIRGPAAARYGNGAAGGVVNIITK KTGDEWRGSWNTYMNAPEHKDEGSTKRTN FSLSGPLGGDFSFRLFGNLDKTQADAWDI NQGHQSERTGIYADTLPAGREGVKNKNID GLVRWEFAPMQSLEFEAGYSRQGNLYAGD TQNTNSNDLVKENYGKETNRLYRNTYSVT WNGAWDNGVTTSNWAQYERTRNSRKGEGL AGGTEGIFNSNQFTDIDLADVMLHSEVSI PFDYLVNQNLTGSEWNQQRMKDNASNTQ ALSGGEIPGYDSTGRSPYSQAEIFSLFAE NNMELTDTTMLTPALRFDHHSIVGNNWSP SLNLSQGLWDDFTLKMGIARAYKAPSLYQ TNPNYILYSKGQGCYASKDGCYLQGNDDL KAETSINKEIGLEFKRDGWLAGVTWFRND YRNKIEAGYAPVYQNNKGTDLYQWENVPK AVVEGLEGTLNVPVSETVNWTNNITYMLQ SKNKETGDRLSIIPEYTLNSTLSWQVRDD VSLQSTFTWYGKQEPKKYNYKGQPVTGSE KNEVSPYSILGLSATWDVTKYVSLTGGVD NVFDKRHWRAGNAQTTGGATGTMYAGAE |

TABLE 3-continued

| Bacterial strain (phage to which developed resistance) | Mechanism or Bacterial Surface Component (gene) | Mutant sequence | Original sequence |
|---|---|---|---|
| | | TNNITYMLQSKNKETGDRLSIIPE YTLNSTLSWQVRDDVSLQSTFTWY GKQEPKKYNYKGQPVTGSEKNDG | TYNESGRTWYLSVNTHF |
| 8M1_6 (8M-1) | Cobalamin uptake (tonB)- | MTLDLPRRFPWPTLLSVAIHGAVV AGLLYTSVHQVIEQPSPTQPIEIT MVAPADLEPPPAAQPVVEPVVEPE PEPEPEVVEPPPKEAPVVIHKPEP KPKPKPKPKLSLSRRKRLNSRSGK | MTLDLPRRFPWPTLLSVAIHGAVVAGLLY TSVHQVIEQPSPTQPIEITMVAPADLEPP PAAQPVVEPVVEPEPEPEPEVVEPPPKEA PVVIHKPEPKPKPKPKPKPKPKPEKKVEQ PKREVKPAAEPRPASPFENNNTAPARTAP STSTAAAKPTVTAPSGPRAISRVQPSYPA RAQALRIEGTVRVKFDVSPDGRIDNLQIL SAQPANMFEREVKSAMRRWRYEQGRPGTG VTMTIKFRLNGVEIN |
| | maltose and maltodextrin transport (LamB)- | VLSHTNDDSGVNKVILRYSDNSDN SVYNKTDALTTVYASFEGSHKFTQ QAQIEYLLAFHDYDNGKDNTDNRK NYGAIVRPMYFWNDVHSTWLEAGY QRVDYDQGG | VLSHTNDDSGVNKVILRYSDNSDNSVYNK TDDLTTVYASFEGSHKFTQQAQIEYLLAF HDYDNGKDNTDNRKNYGAIVRPMYFWNDV HSTWLEAGYQRVDYDQGG |
| 1.2-2_2 20_S92 (1.2-2) | LPS (HBAD) | MSNRLSVVMIAKNAADLLPDCLDS VSWADEIIVLDSGSTDSTVELARR LGAQVYTHTDWRGYGIQRQRAQDY ATGDWVLMIDTDERVTPELRQAIL KVLDAPQRGAIYSIACRNYFLGRF MRHSGWYPDRVLRLYERARYRYND NLVHESLDSLGAEVIPLTGDLLHL TCRDFAGFQQKQLAYAAAWALERH QKGKKTSMAGIFSHTLGAFLKTLL LRGGVLDGKQGWLLAMVNAQYTFT KYTELWALSHGYSEKESS | MSNRLSVVMIAKNAADLLPDCLDSVSWAD EIIVLDSGSTDSTVELARRLGAQVYTHTD WRGYGIQRQRAQDYATGDWVLMIDTDERV TPELRQAILKVLDAPQRGAIYSIARRNYF LGRFMRHSGWYPDRVLRLYERARYRYNDN LVHESLDSLGAEVIPLTGDLLHLTCRDFA GFQQKQLAYAAAWALERHQKGKKTSMAGI FSHTLGAFLKTLLLRGGVLDGKQGWLLAM VNAQYTFTKYTELWALSHGYSEKESS |
| 1.2-2 21 or 22 (1.2-2) | LPS (HBAD) | MSNRLSVVMIAKNAADLLPDCLDS VSWADEIIVLDSGSTDSTVELARR LGAQVYTHTDWRGYGIQRQRAQDY ATGDWVLMIDTDERVTPELRQAIL KVLDAPQRGAIYSIACRNYFLGRF MRHSGWYPDRVLRLYERARYRYND NLVHESLDSLGAEVIPLTGDLLHL TCRDFAGFQQKQLAYAAAWALERH QKGKKTSMAGIFSHTLGAFLKTLL LRGGVLDGKQGWLLAMVNAQYTFT KYTELWALSHGYSEKESS | MSNRLSVVMIAKNAADLLPDCLDSVSWAD EIIVLDSGSTDSTVELARRLGAQVYTHTD WRGYGIQRQRAQDYATGDWVLMIDTDERV TPELRQAILKVLDAPQRGAIYSIARRNYF LGRFMRHSGWYPDRVLRLYERARYRYNDN LVHESLDSLGAEVIPLTGDLLHLTCRDFA GFQQKQLAYAAAWALERHQKGKKTSMAGI FSHTLGAFLKTLLLRGGVLDGKQGWLLAM VNAQYTFTKYTELWALSHGYSEKESS |
| 1.2-3S_6 (1.2-3s) | LPS (IpxM) | MKKNNIEFIPKFEKSFLLPRYWGA WLGVFAFAGIALTPPSFRDPLLGK LGRLVGRLAKSSRRRAQINLLYCF PEKSEYEREAIIDAMYASAPQAMV MMAELGLRDPQKILARVDWQGKAI IDEMQRNNEKVIFLVPHAWGVDIP AMLMASGGQKMAAMFHNQGNPVFD YVWNTVRRRFGGRMHARNDGIKPF IQSVRQGYWGYYLPDQDHGAEHSE FVDFFATYKATLPAIGRLMKVCRP RVVPLFPVYDGKTHRLTVLRPPM DDLLDADDTTIARRMNEEVEVFVK PHTEQYTWILKLLKTRKPGEIEPY KRKELFPKKK | MKKNNIEFIPKFEKSFLLPRYWGAWLGVF AFAGIALTPPSFRDPLLGKLGRLVGRLAK SSRRRAQINLLYCFPEKSEYEREAIIDAM YASAPQAMVMMAELGLRDPQKILARVDWQ GKAIIDEMQRNNEKVIFLVPHAWGVDIPA MLMASGGQKMAAMFHNQGNPVFDYVWNTV RRRFGGRMHARNDGIKPFIQSVRQGYWGY YLPDQDHGAEHSEFVDFFATYKATLPAIG RLMKVCRARVVPLFPVYDGKTHRLTVLVR PPMDDLLDADDTTIARRMNEEVEVFVKPH TEQYTWILKLLKTRKPGEIEPYKRKELFP KKK |
| 1.2-3s 24 (1.2-3s) | LPS (wcaJ or wbaP) | deletion mutation- no proteins | MSRLARNFWTSILLAISDFTGFTVAIVFA IFFVKSFMNDGGHIIANSNINDWVILHTC LGICCVAWYSIRLRHYFYRKTFWFELKEI LRTLVIFAIIEIAVLSFAYWDFSRYILAV TWIFVLFFVPTFRMLTKKCLNFFGLWKRE TIIIGDGNNAVEAWKAINSESNLGFNVTS FVSSTSKDHLKNHINDIPVISLNPKEVTK HFDKRTQFIVALETSESSIRNDWLREFLI NGFRYVSVIPTLRGVPLDSTDMSFIFSHE VMIFRVQQNLAKLSSRILKRLFDIIGSLT IILVSSPL / MSNTNANFEMTGILLGQEARKRKTPQEKI AIIQQTMEPGMNVSHVARLHGIQPSLLFK WKKQYQEGSLTAVAAGEEVVPASELTAAL KQVRELQRLLGKKTMEVEILKEAVEYGQS RKWIAHAPLLPKDGE / |

TABLE 3-continued

| Bacterial strain (phage to which developed resistance) | Mechanism or Bacterial Surface Component (gene) | Mutant sequence | Original sequence |
|---|---|---|---|
| | | | MDSARALVAKGRGIALVSRTMGVSRAQLS LRINRSADWQDKRCNRRNDEADEEILSAI LDIISDMPSYGYRRVWGILRKQRRTEGQP PVNAKRLYRIMSEHNLLLLHDKPERPKRE HKGKIAVAESDMRWCSDGFEFGCDNGEKL RVTFALDCCDREAIDWAASTGGYDSSTVQ DVMLRSVEKRFGDRLPDTAVQWLTDNGSA YTAYETWRFARELNLEPCTTAVSSPQSNG MAERFVKTMKEDYIAFMPKPDVRTALRNL AVAFTHYNENHPHSALGYHSPREYRRQRT SLT |
| 1.2-3s 25 or 26 (1.2-3s) | Iron uptake (fhuA) | MARPKTAQPNHSLRKVAAVVATAV SGMSVYAQAAEQPKQEETITVVAA PAAQESAWGPAPTIAAKRSATATK TDTPIEKTPQSVSVVTRQEMEMRQ PTTVKEALSYTPSVFSTRGSSTTY DVVTIRGFTTSTTVNTNQYLDGMK LQGNNYSEVSMDPYFLERVEVMRG PTSVLYGNSNPGGIVSMVSKRPTT EPLKEVQFKMGTDNLWQTGFDFSD AIDDAGVWSYRLTGLGRSQDAQQQ MAKSTRYAVAPSFSWRPPLAGVRT IKPTSPS | MARPKTAQPNHSLRKVAAVVATAVSGMSV YAQAAEQPKQEETITVVAAPAAQESAWGP APTIAAKRSATATKTDTPIEKTPQSVSVV TRQEMEMRQPTTVKEALSYTPSVFSTRGS STTYDVVTIRGFTTSTTVNTNQYLDGMKL QGNNYSEVSMDPYFLERVEVMRGPTSVLY GNSNPGGIVSMVSKRPTTEPLKEVQFKMG TDNLWQTGFDFSDAIDDAGVWSYRLTGLG RSQDAQQQMAKSTRYAVAPSFSWRPDDKT DFTFLSNFQNDPDAGYYGWLPREGTVVPY YDANGKAHKLPTDFNEGESDNKISRRQKM VGYSFSHQFDDTFTVRQNLRYADVHTLYR SVYGNGYVAPGYMNRAYVRSDEHLNTFTV DTQLQSDFATGAVSHTLLTGVDYSRMRND VDADYGTADPISMSNPQYGNPNIQVTFPY AVLNRMEQTGLYAQDQMEWDKWVMTLGGR YDYATTSTLTRATNSLAENHDQQFSWRGG INYLFDNGISPYFSYSESFEPVSGSNSRG QPFDPSRGKQYEAGVKYVPKDMPVVVTAA VYQLTKDKNLTADPANQAFSIQTGEIRSR GLELEAKAAVNANINVTAAYSYTDAEYTH DTVFNGKRPAEVPRNMASLWADYTFHETA LSGLTIGAGARYIGSTVSYYKNDTSTGKK NDAFSVAGYALMDATVKYDLARFGLPGSS VGVNVNNLFDREYVSSCYSEYACYWGAGR QVVATATFRF |

Non-silent mutations with frequencies above 80% were analyzed, while mutations with a frequency between 20-80% were only analyzed if located outside a mutation hot-spot (e.g., area that shows large polymorphism in control samples grown without phage). Proteins carrying mutations of interest were profiled for their activity, pathway and relevance to known phage receptors as shown in Table 2. The sensitivity of the mutant bacteria to phage other than the phage to which they have developed resistance is shown in FIG. 14. FIG. 14 shows that bacterial mutants which developed resistance (R) to certain phage are sensitive to at least two other phage (S). Gray shaded boxes indicate resistance to the particular phage against which the bacterial mutant was raised. For example, Colon1_1 11_S83 and Colon1_1 38_S110 are resistant to and raised against colon1. Genomic modifications which affect phage infection (i.e., modifications found in a phage-resistant mutant bacteria that arose in a culture containing a specific phage capable of infecting a specific bacteria) are shown in Table 2.

Example 13: Comparative Host Range Analysis of all Phage

Host range analysis of all isolated phage was performed on different KP2 phage resistant mutants isolated as described above. In addition, the host range of phages was examined on all 14 KP2 clinical variants isolated from clinical stool samples as described in Example 1 in order to ascertain the ability of isolated phage to target clinical variants originating in different individuals. All KP2 clinical variants were found to be sensitive to plurality of the KP2 targeting phage and two patterns of sensitivity, represented by the phage sensitivities of KP2 clinical variants CT-123-1 and CT-141-1 were observed. Each of the phage were added (10 μL) to bacterial lawns of the different K. pneumoniae strains, in 48 well plates by drop assay. Plates were incubated for 2-3 hrs (37° C.) in aerobic conditions, after which plaques become visible on the bacterial lawns. Host range was carried out for each of the phage at a titer of $1\times10^6$ PFU/mL as determined on the original bacteria on which that phage was isolated. FIG. 1 shows the results of the host range analysis of bacteriophage isolated against wild-type KP2 bacteria, clinical KP2 variants and mutant KP2 bacteria resistant to infection by particular KP2 bacteriophage. "S" indicates susceptibility (10 plaques or more to full clearing) and "R" indicates resistance (less than 10 plaques) The results demonstrate that the infectivity pattern of phage largely follow their taxonomic classification. Thus, for example, all three phage classified as Myoviridae Tevenvirinae Kp15 have identical infectivity patterns on KP2, KP2 clinical variants and KP2 mutants as do all the eleven phage of the classification Podoviridae Autographvirinae T7virus. Among the 16 phage of the classification Myoviridae Tevenvirinae T4 virus, the infectivity pattern is identical on six hosts and only varies on one representative host. Among the ten phages of classification Podoviridae Autographivirinae Kp34virus, only 2 have a different infectivity pattern on two of the ten representative hosts. The only phage classified as Myoviridae Vequintavirineae Scivirus has a unique infectivity pattern. Two of the three Siphoviridae phage are also very similar in their infectivity pattern, differing only in their ability to target one of the seven bacterial hosts.

Example 14: Liquid Dynamic Behavior of Phage Combinations

A total of 12 phage were selected for compiling 10 phage cocktails for further characterization in liquid dynamics study. In this study, the rate of bacterial lysis and the time to appearance of resistant mutant bacteria, as reflected by alternations in the culture OD was examined. The 12 phage that were used are: M16-6c, M16-9a, KP2-5a, KP2-5-1, KP2-8a, KP2-8c, MCoc4c, MCoc5c, KP2-4c, 1.2-2, 1.2-3b, and colon1. The cocktails are set forth below:

| Cocktail number | Member phages | | | | |
|---|---|---|---|---|---|
| 30 | KP2-5a | Mcoc5c | KP2-8a | colon1 | 1.2-3b |
| 40 | KP2-5-1 | Mcoc4c | KP2-8c | colon1 | 1.2-3b |
| 50 | 1.2-2 | Mcoc5c | KP2-8a | colon1 | 1.2-3b |
| 16 | M16-9a | Mcoc4c | KP2-8c | colon1 | 1.2-3b |
| 52 | 1.2-2 | Mcoc4c | KP2-8c | colon1 | 1.2-3b |
| 49 | 1.2-2 | Mcoc4c | KP2-8a | colon1 | 1.2-3b |
| 54 | 1.2-2 | KP2-4c | KP2-8c | colon1 | 1.2-3b |
| 51 | 1.2-2 | KP2-4c | KP2-8a | colon1 | 1.2-3b |
| 10 | M16-6c | KP2-4c | KP2-8a | colon1 | 1.2-3b |
| 2 | M16-6c | Mcoc4c | KP2-8a | colon1 | 1.2-3b |

Liquid dynamics of the 10 cocktails was explored in the following manner. KP2 was grown at 37° C. with agitation to OD 1.5, diluted 1:1000 in BHIS medium and cultured at 37° C. with agitation. The culture OD was monitored until it reached OD 0.2 at which time MMC ions (1 mM final concentration) were added to the culture and 200 µl was dispensed per well in a 96 well plate. Each phage was diluted from the phage stock to $10^8$ PFU/mL and added to the desired cocktail at a final concentration of $10^6$ PFU/well. 10 µl of each cocktail ($10^4$ total phage particles) was added to the wells, in duplicates. BHIS media served as the blank sample and host bacteria without any phage served as control. 50p L of mineral oil was added to each well to limit evaporation of the sample, followed by a thin sterile optically transparent polyester film to keep the culture sterile. Plates were incubated overnight at 37° C. with agitation in a robotic plate reader (Freedom EVO 75, Tecan) and OD600 was measured every 15 minutes. The performance of the cocktails was followed for up till 20 hours.

Figure 9:
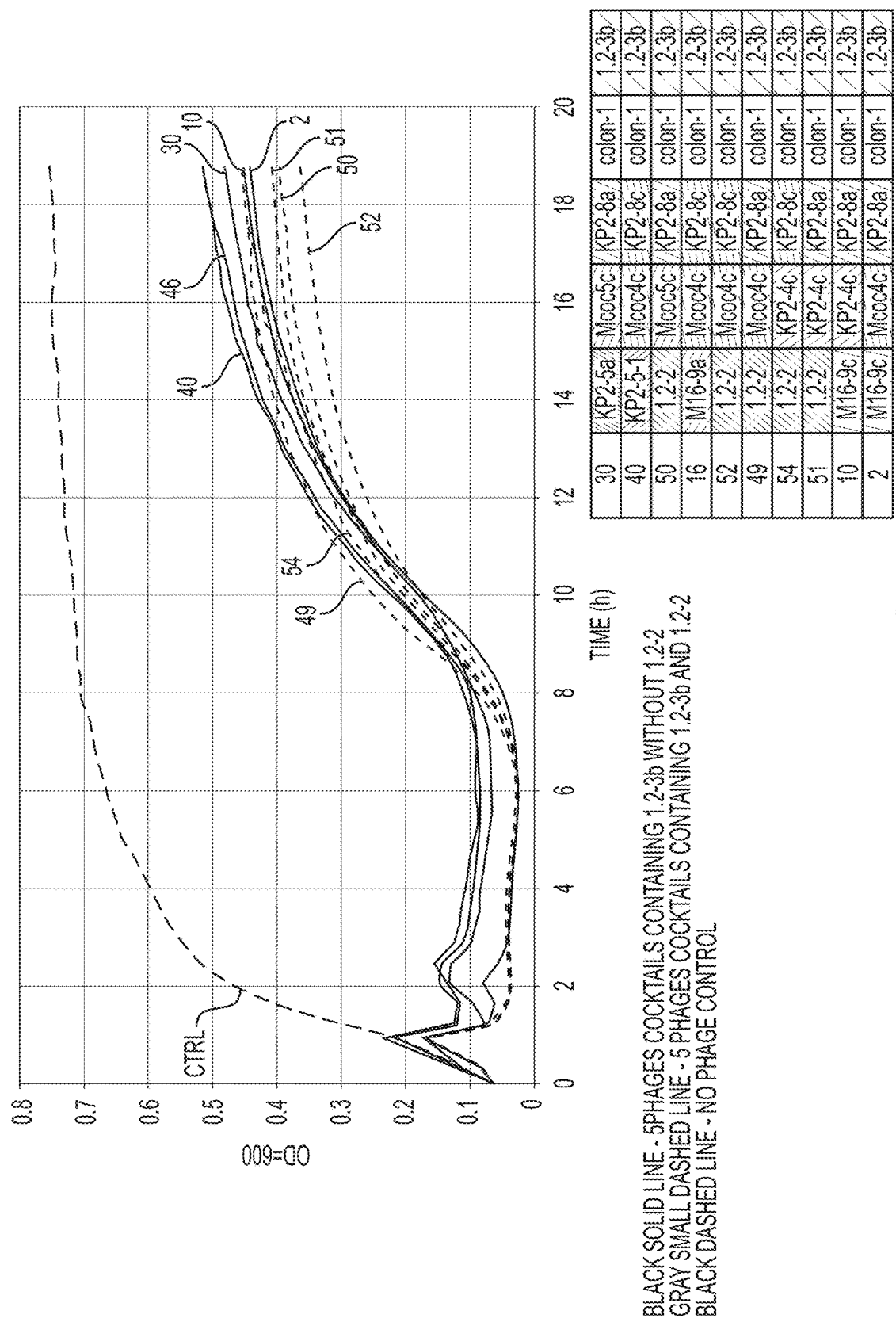
FIG. 9 presents growth curves of in vitro liquid infection of KP2 with bacteriophage compositions (cocktails): five-phage compositions without 1.2-2 (black solid line); five-phage compositions containing 1.2-2 (gray small dashed line); and control (no phage) (black dashed line), as further described in Example 14.

FIG. 9 presents growth curves of in vitro infection of KP2 with bacteriophage compositions (cocktails) all of which included phage 1.2-3b: five-phage compositions without 1.2-2 (black solid line); five-phage compositions containing 1.2-2 (gray small dashed line); and control (no phage; black dashed line). Most of the cocktail compositions that included 1.2-2 as well 1.2-3b appeared to bring about speedier and more complete collapse of the KP2 growth curve immediately after introduction and slower appearance of mutants beginning about 7 hours later as compared to most compositions that did not include phages 1.2-2. Additional cocktails were designed to examine the contribution of these phage to eradication dynamics in combination with phages from different taxonomic classifications.

The two phage, 1.2-2 (group Myoviridae/Tevenvirinae/Kp15virus) and 1.2-3b (group Podoviridae/Autographivirinae/T7virus) whose contribution to cocktail efficacy in vitro was discussed above, were combined in various combinations with representative phage from other taxonomic groups as shown below, to comprise cocktails for additional analysis. Table 4 shows phages included in the cocktails and their respective taxonomic classifications.

TABLE 4

| Group | Podoviridae/ Autographivirinae/ T7virus (PAT) | Podoviridae/ Autographivirinae/ Kp34virus (PAK) | Myoviridae/ Tevenvirinae/ T4virus (MTT) | Myoviridae/ Tevenvirinae/ Kp15virus (MTK) | Siphoviridae/ T5virus (ST) |
|---|---|---|---|---|---|
| Phage | 1.2-3b | Mcoc5c | colon1 | 1.2-2 | 1.2-3s |

Three and four phage cocktails were designed based on combinations involving members from different taxonomic classifications. All combinations included either both 1.2-2 and 1.2-3b or just 1.2-3b. The cocktails were:

| Cocktail name | Phage 1 | Phage 2 | Phage 3 | Phage 4 |
|---|---|---|---|---|
| 3.1 | 1.2-3b | 1.2-2 | 1.2-3s | |
| 3.2 | 1.2-3b | 1.2-2 | colon1 | |
| 3.3 | 1.2-3b | 1.2-2 | MCoc5c | |
| 3.4 | 1.2-3b | 1.2-3s | colon1 | |
| 3.5 | 1.2-3b | 1.2-3s | MCoc5c | |
| 3.6 | 1.2-3b | colon1 | MCoc5c | |
| 4.1 | 1.2-3b | 1.2-2 | 1.2-3s | colon1 |
| 4.2 | 1.2-3b | 1.2-2 | 1.2-3s | MCoc5c |
| 4.3 | 1.2-3b | 1.2-2 | colon1 | MCoc5c |
| 4.4 | 1.2-3b | 1.2-3s | colon1 | MCoc5c |

The corresponding group combinations are:

| Cocktail name | Group combination |
|---|---|
| 3.1 | PAT/MTK/ST |
| 3.2 | PAT/MTK/MTT |
| 3.3 | PAT/MTK/PAK |
| 3.4 | PAT/ST/MTT |
| 3.5 | PAT/ST/PAK |
| 3.6 | PAT/MTT/PAK |
| 4.1 | PAT/MTK/ST/MTT |
| 4.2 | PAT/MTK/ST/PAK |
| 4.3 | PAT/MTK/MTT/PAK |
| 4.4 | PAT/ST/MTT/PAK |

Figure 16A:
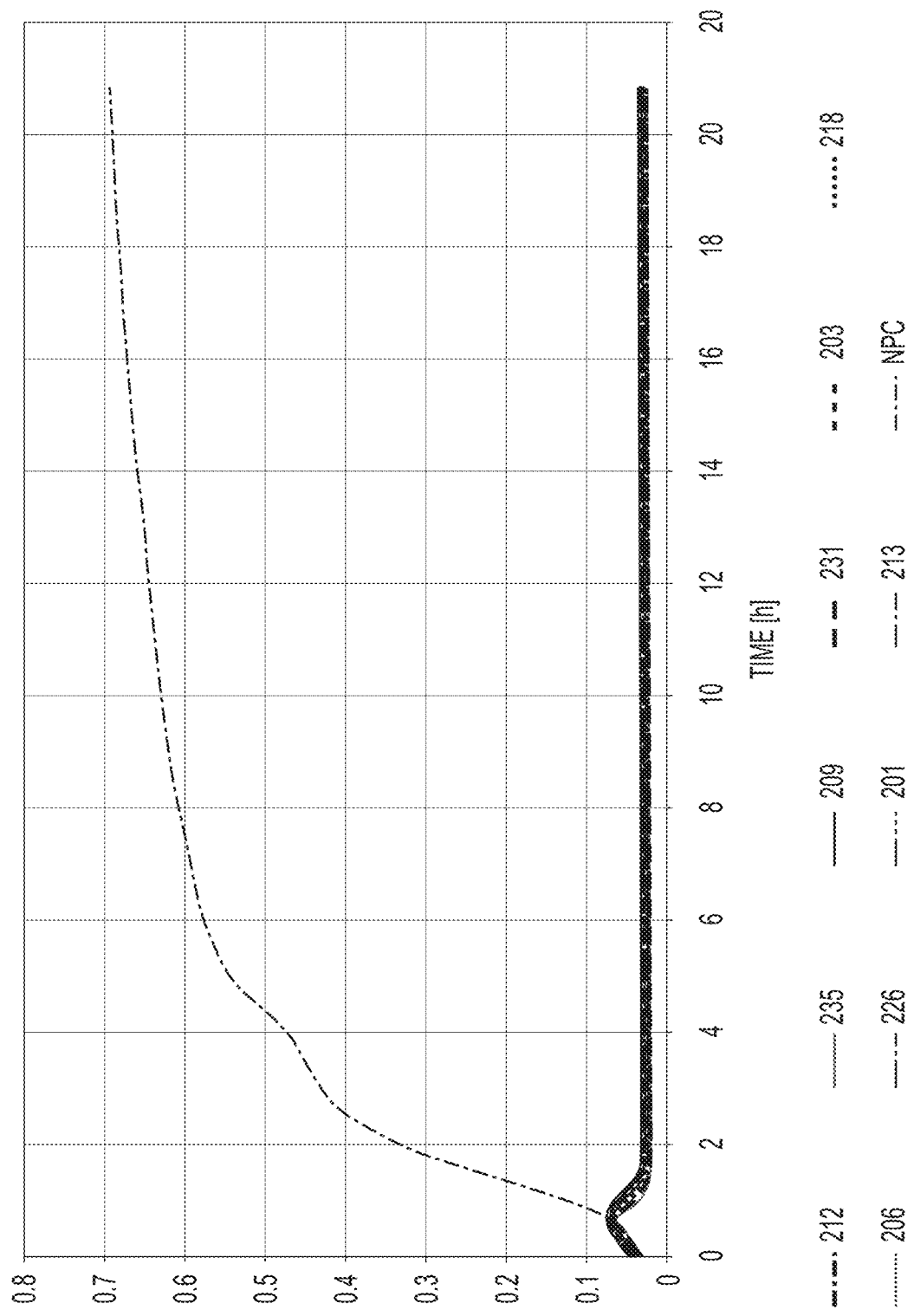
FIGS. 16a, 16b, 16c, 16d, 16e, 16f, 16g, 16h, 16i and 16j present growth curves of in vitro liquid infection of KP2 variants with different bacteriophage compositions (cocktails) as further specified in table 5 and non-phage control (NPC). Host bacteria used.
Figure 16B:
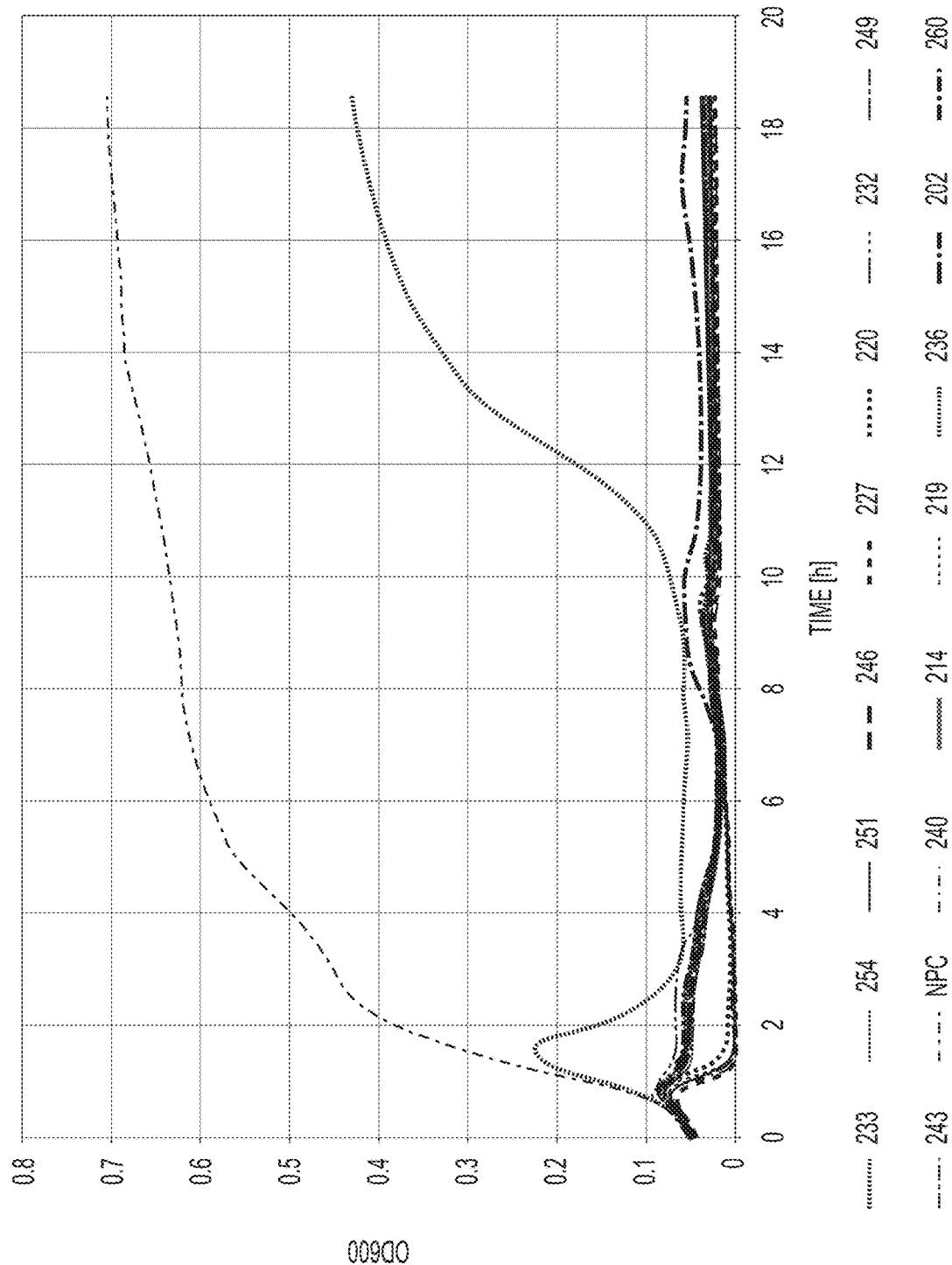
Figure 16C:
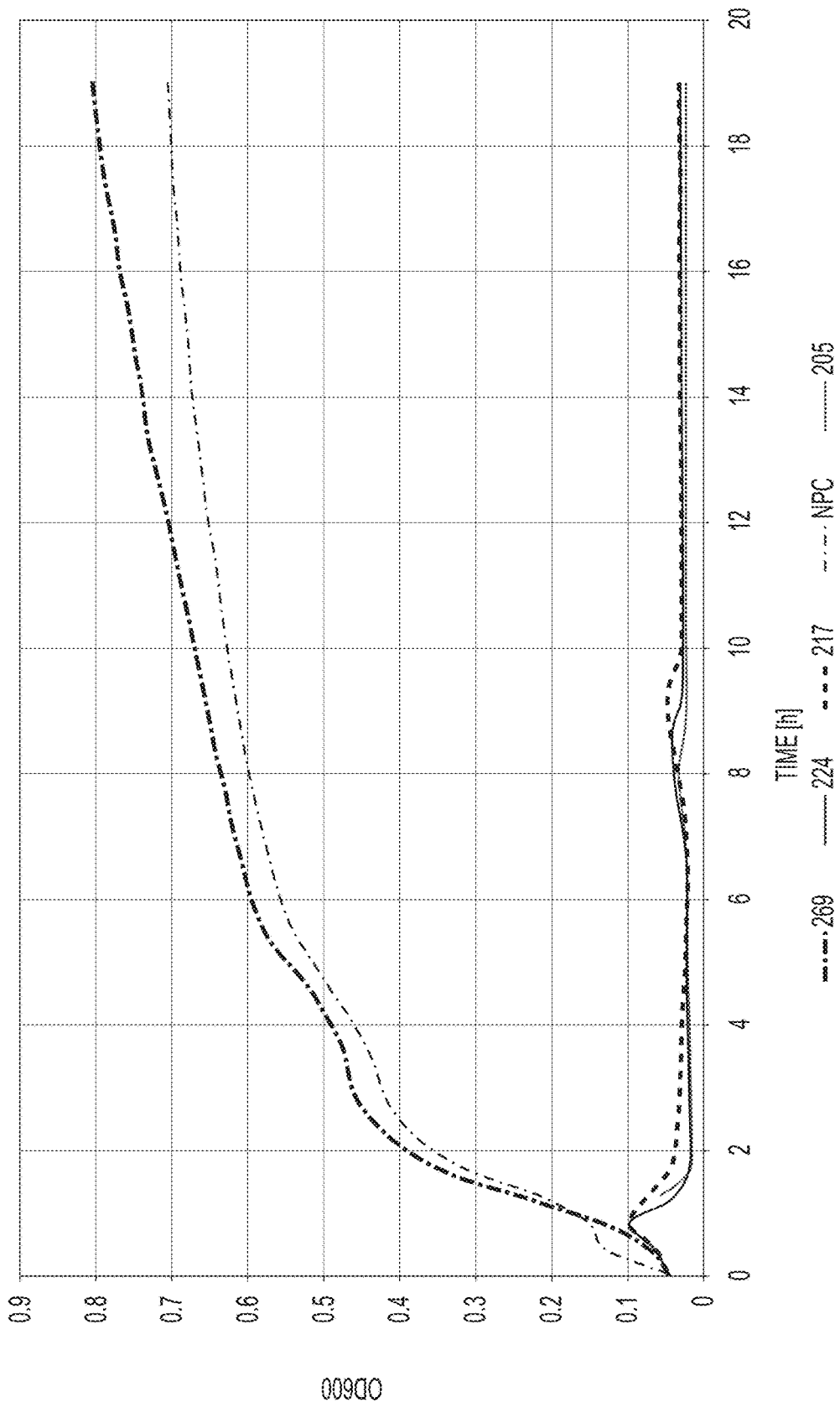
Figure 16D:
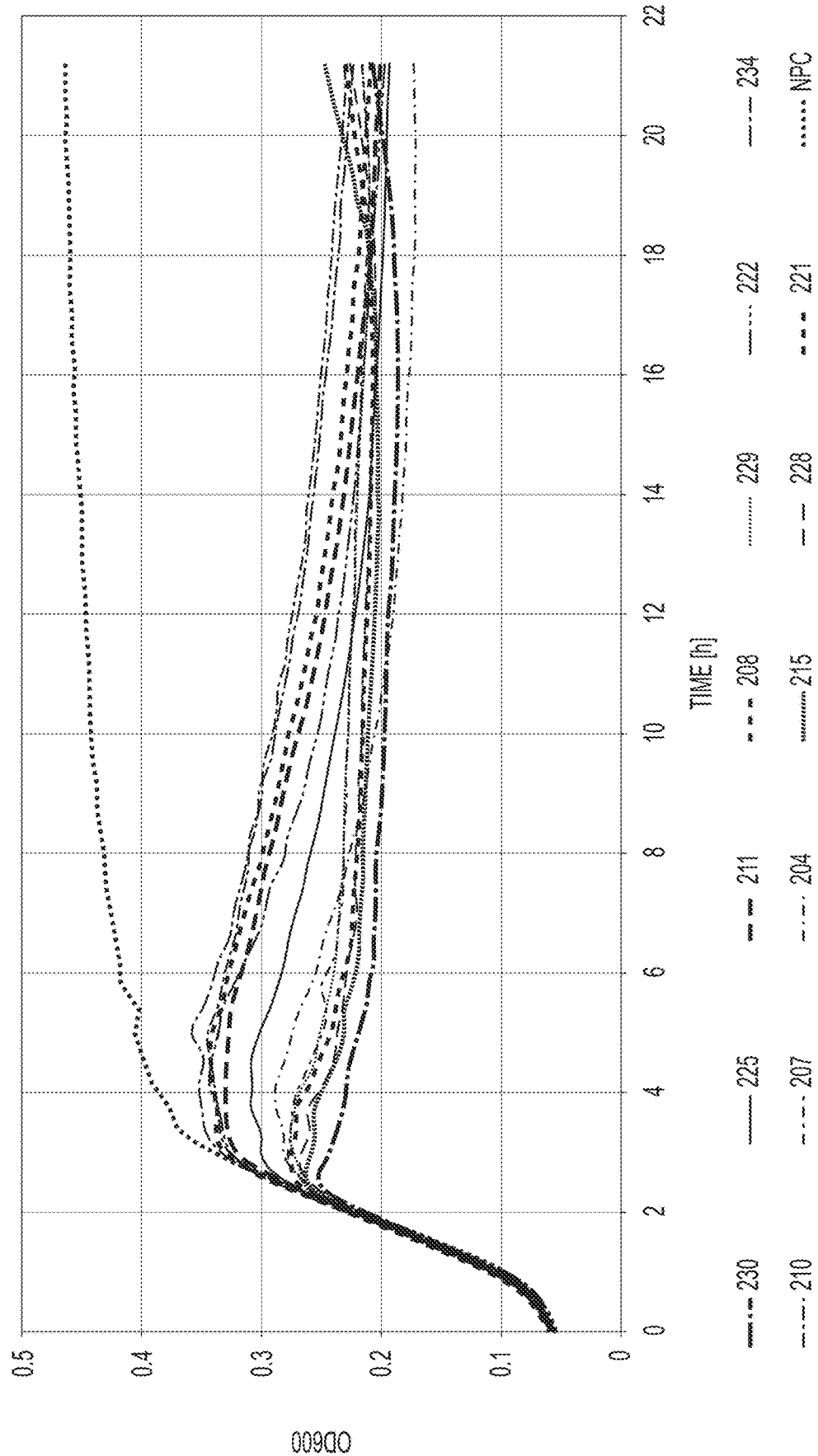
Figure 16E:
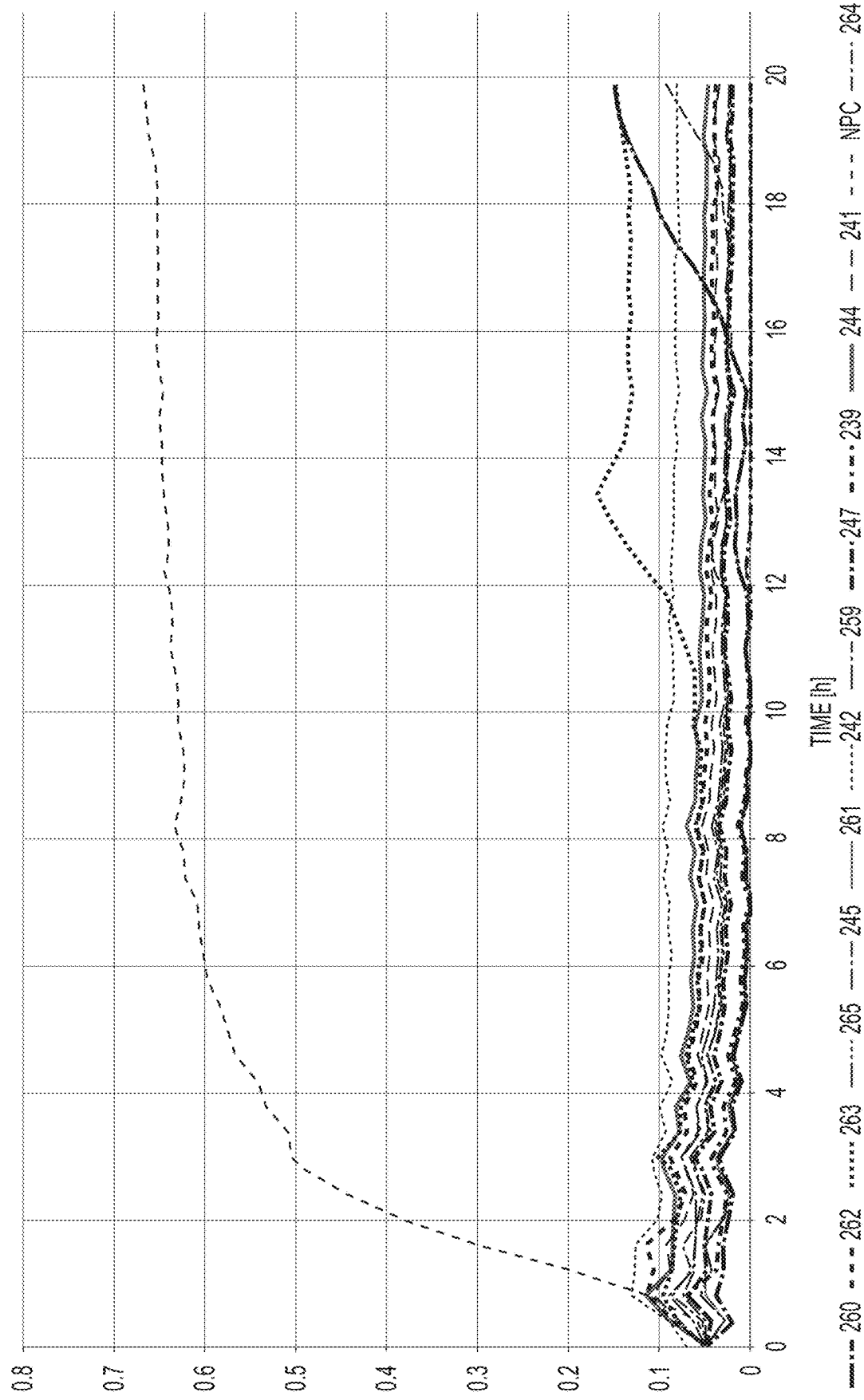
Figure 16F:
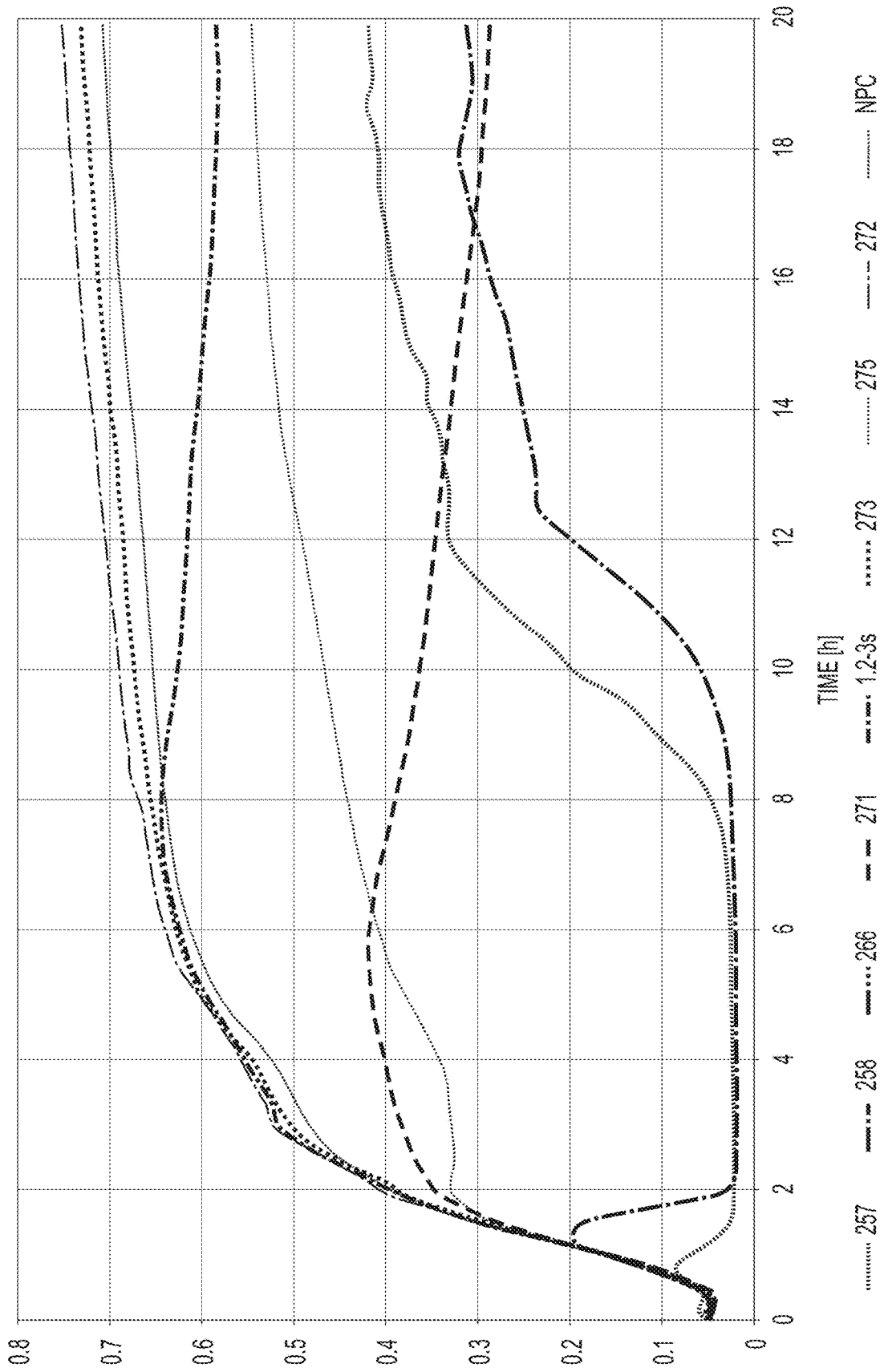
Figure 16G:
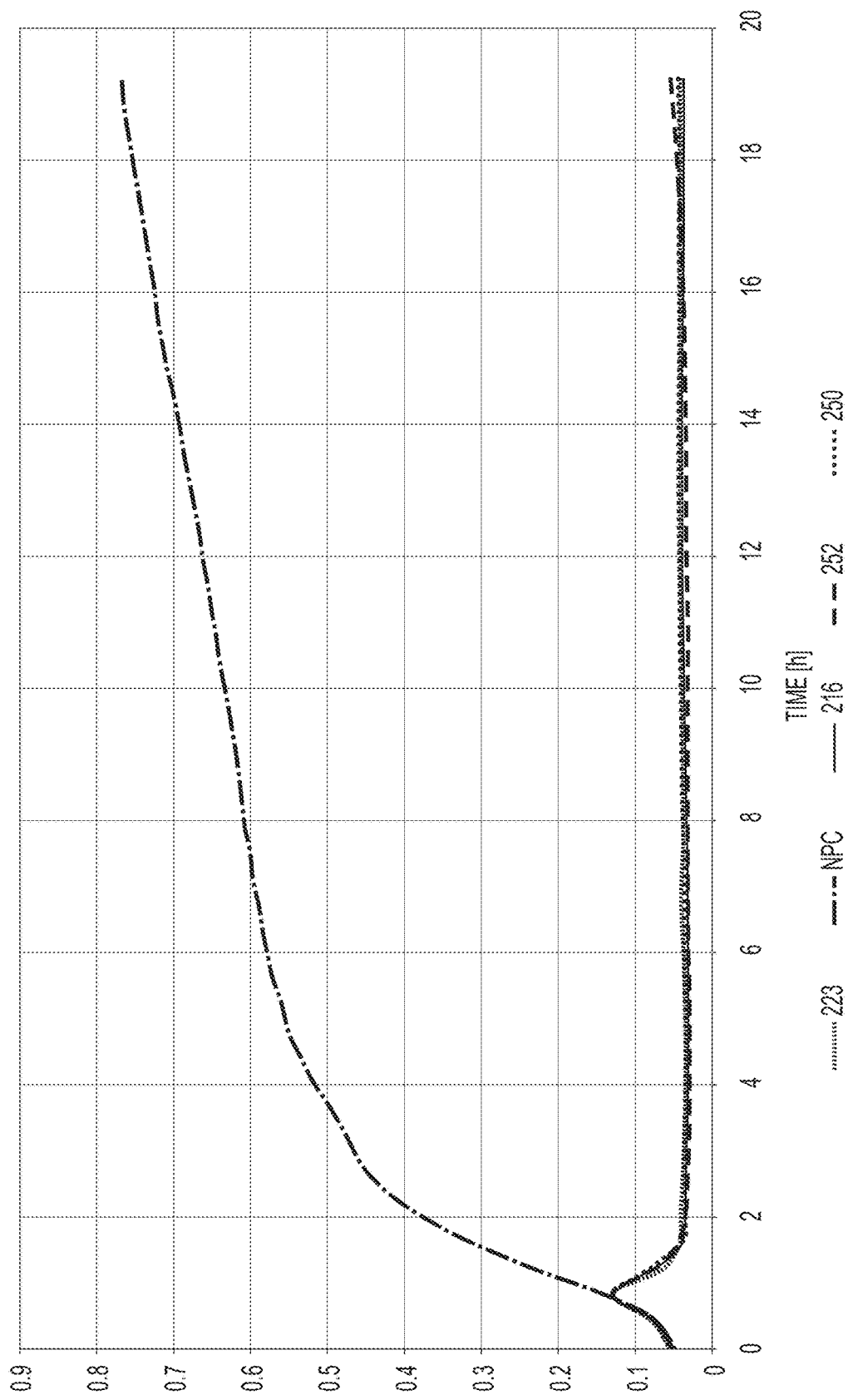
Figure 16H:
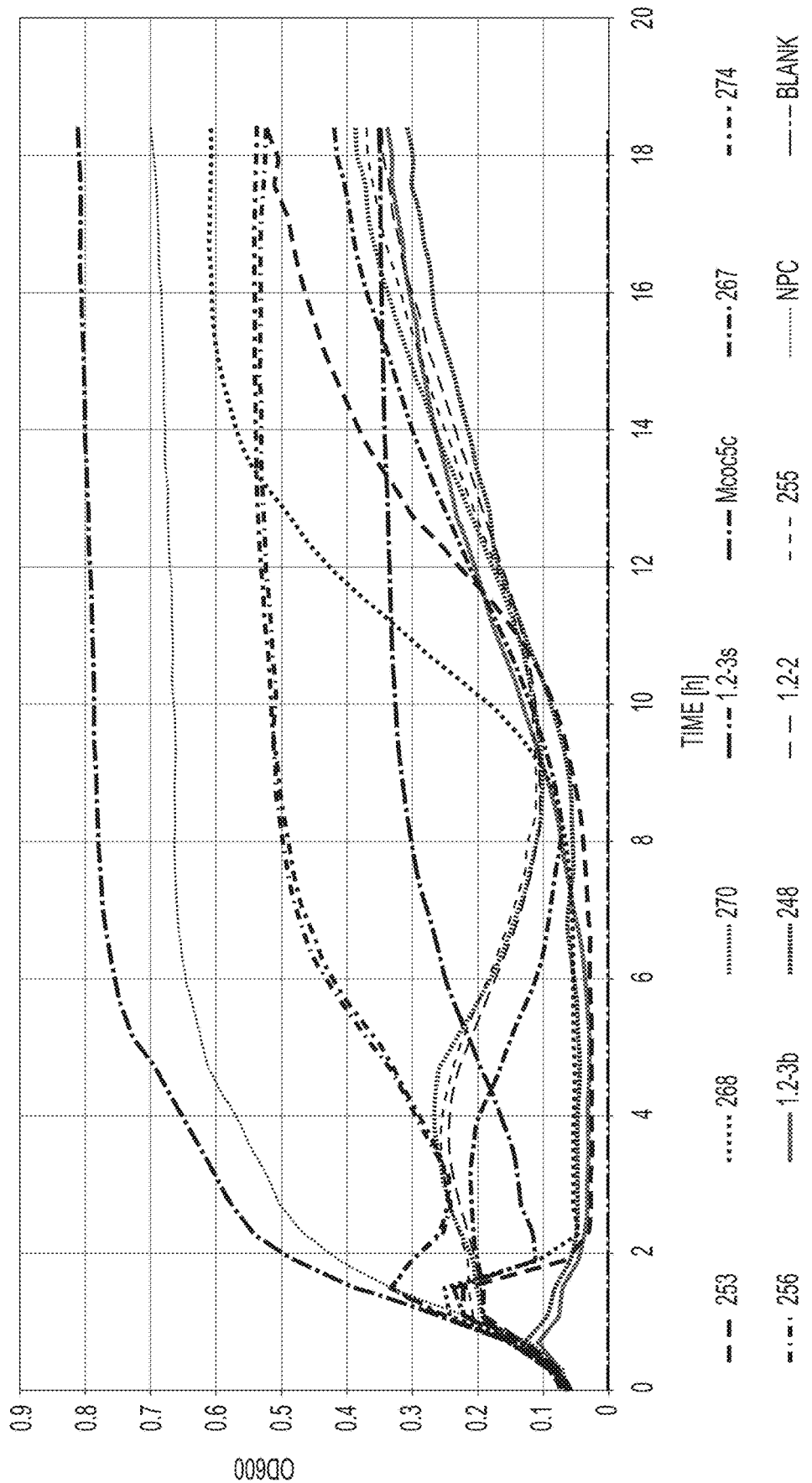
Figure 16I:
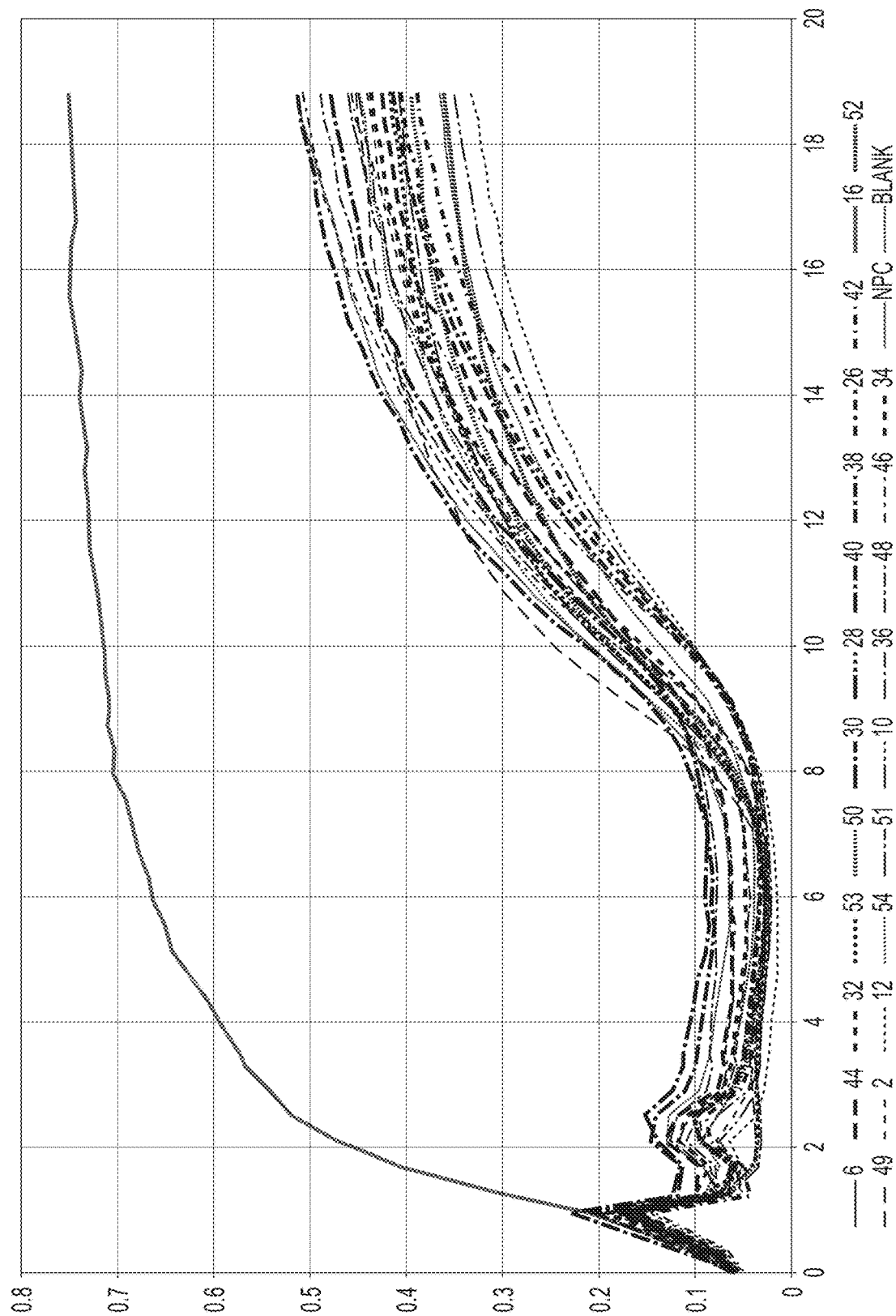
Figure 16J:
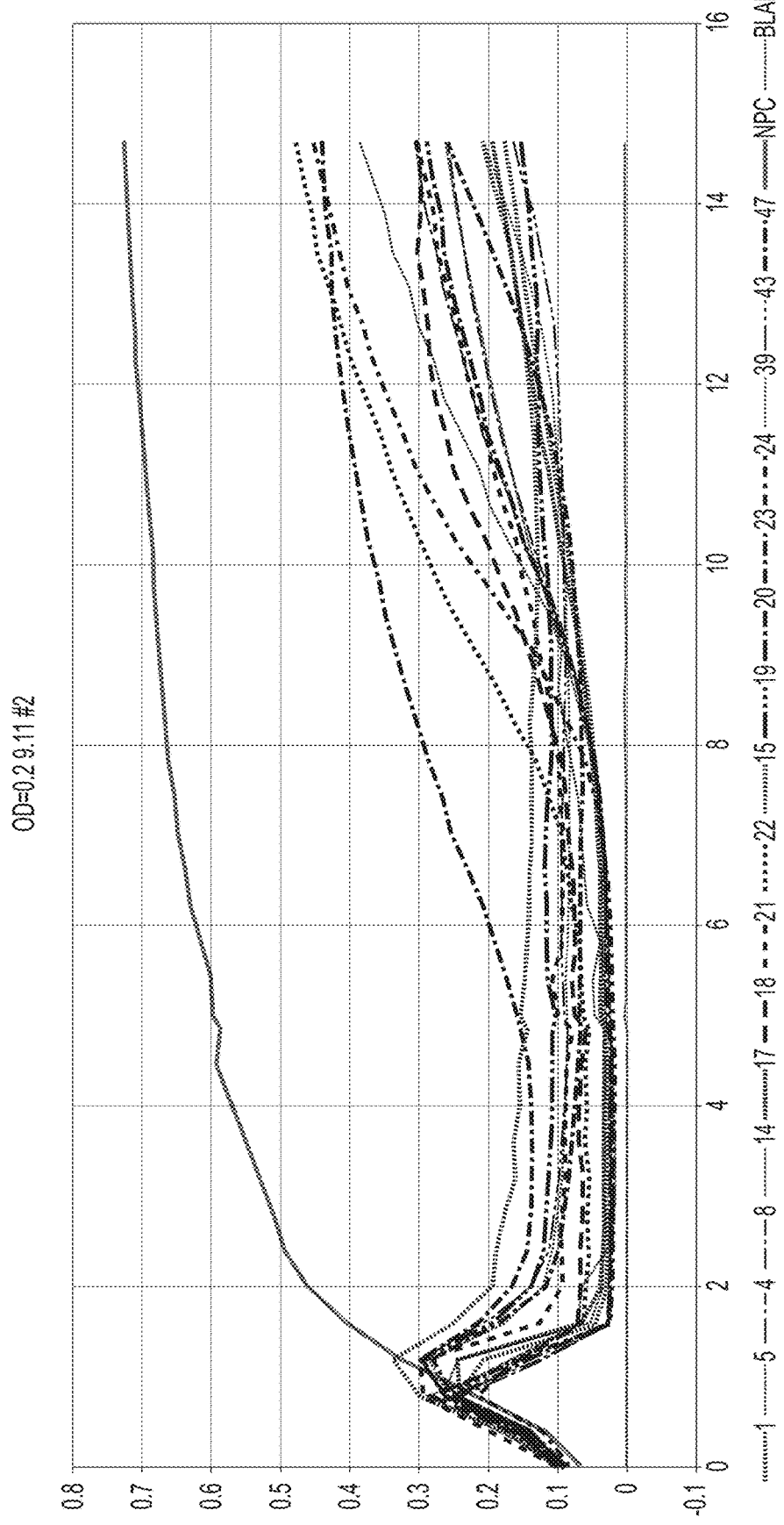

The results for various 3 and 4 phage cocktails are shown in FIG. 10 and FIG. 16e. FIG. 10 shows in vitro infection of KP2 with bacteriophage compositions containing 3 phage (black solid line) or 4 phage (gray dashed line) and no phage control (gray solid line) in liquid. The KP2 growth curve without phage treatment is represented by the solid gray line, KP2 growth curves with combinations of 3 phages are represented by the black solid lines, and KP2 growth curves with combinations of 4 phages are illustrated by the gray dashed lines.

The combination of the 3 phage cocktail composed of 1.2-3s, 1.2-3b, and 1.2-2 prevented the appearance of mutants up to 20 hours, until the end of the study (lowest black solid line).

Further studies were carried out to compare the efficacy of the three phage cocktail 3.1 described above to that of two additional cocktails. The three combinations that were tested were:

Composition 1: 1.2-2+1.2-3s+1.2-3b (groups: MTK/ST/PAT)
Composition 2: Composition 1+Mcoc-5c (groups: MTK/ST/PAT/PAK)
Composition 3: Composition 2+8M-1 (groups: MTK/ST/PAT/PAK/S)

Figure 11:
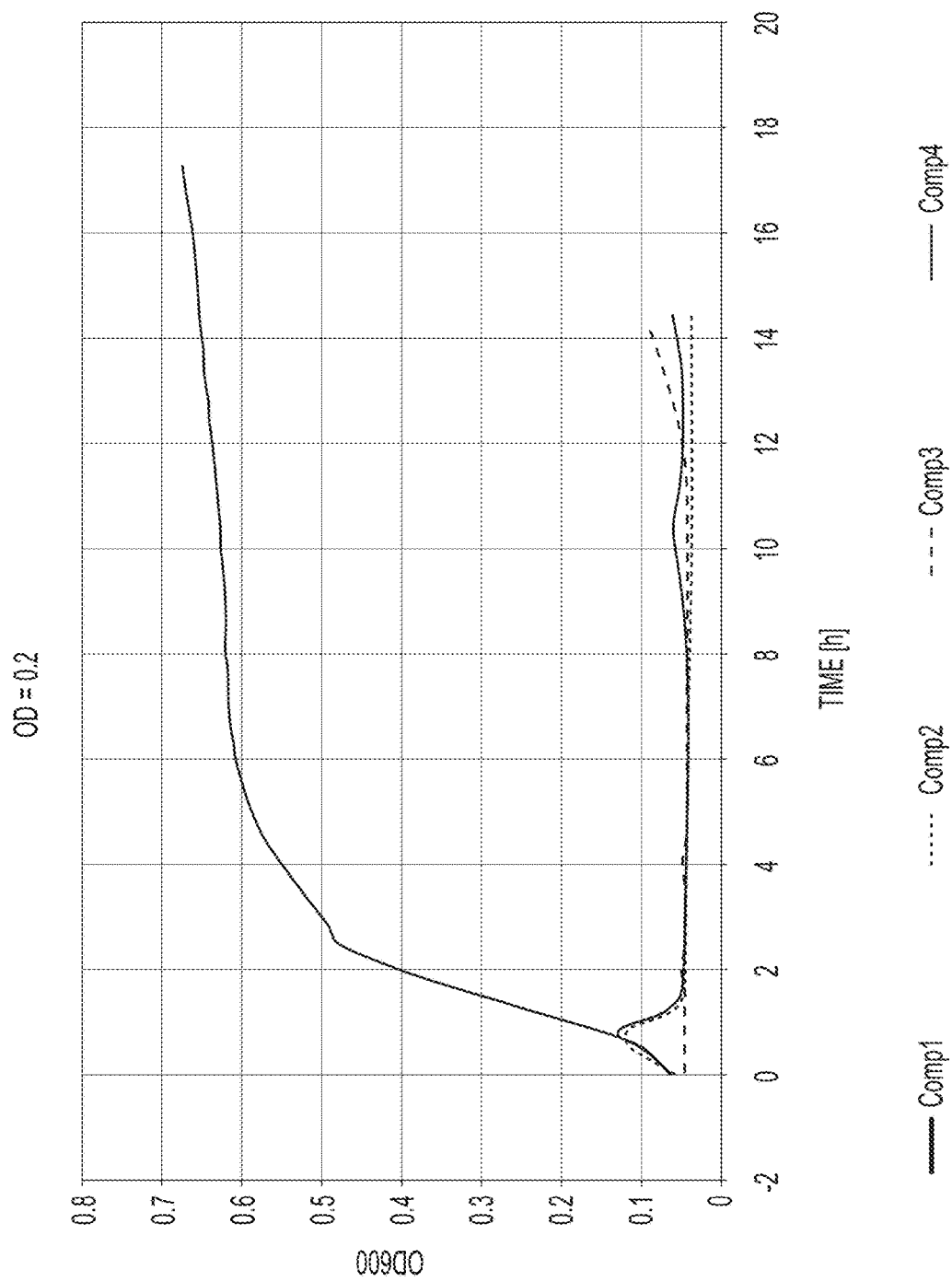
FIG. 11 shows in vitro infection of KP2 with bacteriophage cocktails: Composition 1 (1.2-2, 1.2-3s, 1.2-3b, solid black line), Composition 2 (Composition 1+Mcoc-5c, dashed gray line), Composition 3 (Composition 2+8M-1, dashed black line), and no phage control (solid gray line).

FIG. 11 shows KP2 growth curves for the different phage combinations. The KP2 growth curve without phage is illustrated by the solid gray line. There were no significant differences between the three cocktails Additionally, no mutants appeared up to the time of the end of study (15 hrs).

Table 5 below lists phage combinations with respective liquid dynamics presented in FIGS. 16a-j. FIGS. 16a-j present growth curves of in vitro liquid infection of KP2 variants with different bacteriophage compositions (cocktails). Host bacteria used: FIGS. 16a-c, 16f: CT-141-1, FIG. 16d: CT-123-1, FIG. 16e, g-j: KP2. Experimental procedure used was as described above. Index numbers 1-20 in Table 5 header represent the following phage: [1: 1.2-2], [2: 1.2-3b], [3: 1.2-3s], [4: 1.2-4br], [5: 8M-1], [6: 8M-7], [7: 8M-8], [8: colon1], [9: KP2-4c], [10: KP2-5], [11: KP2-5-1], [12: KP2-5a], [13: KP2-7-1c], [14: KP2-8a], [15: KP2-8c], [16: M16-6c], [17: M16-9a], [18: Mcoc4c], [19: MCoc5c], [20: PKP-55].

TABLE 5

| Additional phage combinations | | | | | | | | | | | | | | | | | | | | | |
|---|---|---|---|---|---|---|---|---|---|---|---|---|---|---|---|---|---|---|---|---|---|
| Combination number | FIG. | 1 | 2 | 3 | 4 | 5 | 6 | 7 | 8 | 9 | 10 | 11 | 12 | 13 | 14 | 15 | 16 | 17 | 18 | 19 | 20 |
| 201 | 16a | X | X | X | X | X | X | | | | | | | | | | | | | | | |
| 202 | 16b | X | X | X | X | X | | | | | | | | | | | | | | | | |
| 203 | 16a | X | X | X | X | | X | | | | | | | | | | | | | | | |
| 204 | 16d | X | X | X | X | | | X | | | | | | | | | | | | | | |
| 205 | 16c | X | X | X | X | | | | | | | | | | | | | | | | | |
| 206 | 16a | X | X | X | | X | X | | | | | | | | | | | | | | | |
| 207 | 16d | X | X | X | | X | | X | | | | | | | | | | | | | | |
| 208 | 16d | X | X | X | | X | | | | | | | | | | | | | | | | |
| 209 | 16a | X | X | X | | | X | | | | | | | | | | | | | | | |
| 210 | 16d | X | X | X | | | | X | | X | | | | | | | | | | | | |
| 211 | 16d | X | X | X | | | | X | | | | | | | | | | | | | | |
| 44 | 16i | X | X | X | | | | | X | | | | X | | | | | | | | | |
| 42 | 16i | X | X | X | | | | | X | | | | | | | X | | | | | | |
| 212 | 16a | X | X | X | | | | | | | | | | | | | | | | | | |
| 213 | 16a | X | X | | X | X | X | | | | | | X | | | | | | | | | |
| 214 | 16b | X | X | | X | X | X | | | | | | | | | | | | | | | |
| 215 | 16d | X | X | | X | X | | X | | | | | | | | | | | | | | |
| 216 | 16g | X | X | | X | X | | | | | X | | | | | | | | | | | |
| 216 | 16g | X | X | | X | X | | | | | X | | | | | | | | | | | |
| 217 | 16c | X | X | | X | X | | | | | | | | | | | | | | | | |
| 218 | 16a | X | X | | X | | X | | | | | | X | | | | | | | | | |
| 219 | 16b | X | X | | X | | X | | | | | | | | X | | | | | | | |
| 220 | 16b | X | X | | X | | X | | | | | | | | | | | | | | | |
| 221 | 16d | X | X | | X | | | X | | X | | | | | | | | | | | | |
| 222 | 16d | X | X | | X | | | X | | | | | | | | | | | | | | |
| 223 | 16g | X | X | | X | | | | | X | X | | | | | | | | | | | |
| 223 | 16g | X | X | | X | | | | | X | X | | | | | | | | | | | |
| 224 | 16c | X | X | | X | | | | | | | | | | | | | | | | | |
| 225 | 16d | X | X | | X | | | | | | | | | | | | | | | | | |
| 226 | 16a | X | X | | | X | X | | | | | | X | | | | | | | | | |
| 227 | 16b | X | X | | | X | X | | | | | | | | | | | | | | | |
| 228 | 16d | X | X | | | X | | X | | X | | | | | | | | | | | | |
| 229 | 16d | X | X | | | X | | X | | | | | | | | | | | | | | |
| 279 | 16j | X | X | | | X | | | X | | | | X | | | | | | | | | |
| 41 | 16i | X | X | | | X | | | X | | | | | | | X | | | | | | |
| 230 | 16d | X | X | | | X | | | | | | | | | | | | | | | | |
| 231 | 16a | X | X | | | | X | | | | | | X | | | | | | | | | |
| 232 | 16b | X | X | | | | X | | | | | | | | X | | | | | | | |
| 233 | 16b | X | X | | | | X | | | | | | | | | | | | | | | |
| 234 | 16d | X | X | | | | | X | | X | | | | | | | | | | | | |
| 235 | 16a | X | X | | | | | | | | | | X | | | | | | | | | |
| 236 | 16b | X | | | X | X | X | X | | | | | | | | | | | | | | |
| 239 | 16e | X | | | X | X | X | | | | | | | | | | | | | | | |
| 239 | 16e | X | | | X | X | X | | | | | | | | | | | | | | | |
| 240 | 16b | X | | | X | X | | X | | | | | | | | | | | | | | |
| 241 | 16e | X | | | X | X | | | | X | | | | | | | | | | | | |
| 241 | 16e | X | | | X | X | | | | X | | | | | | | | | | | | |
| 242 | 16e | X | | | X | X | | | | | | | | | | | | | | | | |
| 242 | 16e | X | | | X | X | | | | | | | | | | | | | | | | |
| 243 | 16b | X | | | X | | X | X | | | | | | | | | | | | | | |
| 53 | 16i | X | | | X | | X | | | X | | | X | | | | | | | | | |
| 50 | 16i | X | | | X | | X | | | X | | | | | X | | | | | | | |
| 244 | 16e | X | | | X | | X | | | X | | | | | | | | | | | | |
| 244 | 16e | X | | | X | | X | | | X | | | | | | | | | | | | |
| 245 | 16e | X | | | X | | X | | | | | | | | | | | | | | | |
| 245 | 16e | X | | | X | | X | | | | | | | | | | | | | | | |

TABLE 5-continued

Additional phage combinations

| Combination number | FIG. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| 246 | 16b | X |   | X |   |   | X |   |   |   |   |   |   |   |   |   |   |   |   |   |   |
| 32 | 16b | X |   | X |   |   |   |   | X |   |   |   | X |   |   |   | X |   |   |   |   |
| 282 | 16j | X |   | X |   |   |   |   | X |   |   |   | X |   |   |   |   |   |   | X |   |
| 283 | 16j | X |   | X |   |   |   |   | X |   |   |   | X |   |   |   |   |   |   |   | X |
| 30 | 16i | X |   | X |   |   |   |   | X |   |   |   |   |   |   | X | X |   |   |   |   |
| 285 | 16j | X |   | X |   |   |   |   | X |   |   |   |   |   |   | X |   |   |   | X |   |
| 6 | 16i | X |   | X |   |   |   |   | X |   |   |   |   |   |   | X |   |   |   |   | X |
| 247 | 16e | X |   | X |   |   |   |   | X |   |   |   |   |   |   |   |   |   |   |   |   |
| 247 | 16e | X |   | X |   |   |   |   | X |   |   |   |   |   |   |   |   |   |   |   |   |
| 248 | 16h | X |   | X |   |   |   |   |   |   |   |   |   |   |   |   |   |   |   |   |   |
| 249 | 16b | X |   |   | X | X | X |   |   |   |   |   |   |   |   |   |   |   |   |   |   |
| 250 | 16g | X |   |   | X | X |   |   |   |   |   | X |   | X |   |   |   |   |   |   |   |
| 250 | 16g | X |   |   | X | X |   |   |   |   |   | X |   | X |   |   |   |   |   |   |   |
| 251 | 16b | X |   |   | X |   | X |   |   |   |   |   |   |   |   |   |   |   |   |   |   |
| 252 | 16g | X |   |   | X |   |   |   |   | X | X |   | X |   |   |   |   |   |   |   |   |
| 252 | 16g | X |   |   | X |   |   |   |   | X | X |   | X |   |   |   |   |   |   |   |   |
| 253 | 16h | X |   |   | X |   |   |   |   |   |   |   |   |   |   |   |   |   |   |   |   |
| 254 | 16b | X |   |   |   | X | X |   |   |   |   |   |   |   |   |   |   |   |   |   |   |
| 31 | 16i | X |   |   |   | X |   |   | X |   |   |   | X |   |   |   | X |   |   |   |   |
| 296 | 16j | X |   |   |   | X |   |   | X |   |   |   | X |   |   |   |   |   |   | X |   |
| 7 | 16i | X |   |   |   | X |   |   | X |   |   |   | X |   |   |   |   |   |   |   | X |
| 29 | 16i | X |   |   |   | X |   |   | X |   |   |   |   |   |   | X | X |   |   |   |   |
| 299 | 16j | X |   |   |   | X |   |   | X |   |   |   |   |   |   | X |   |   |   | X |   |
| 300 | 16j | X |   |   |   | X |   |   | X |   |   |   |   |   |   | X |   |   |   |   | X |
| 255 | 16h | X |   |   |   | X |   |   |   |   |   |   |   |   |   |   |   |   |   |   |   |
| 256 | 16h | X |   |   |   |   |   |   | X |   |   |   |   |   |   |   |   |   |   |   |   |
| 257 | 16f | X |   |   |   |   |   |   |   |   |   |   |   |   |   |   |   |   |   |   |   |
| 48 | 16i |   | X | X |   |   |   |   | X |   |   |   | X |   |   |   |   | X |   |   |   |
| 40 | 16i |   | X | X |   |   |   |   | X |   |   |   | X |   |   |   |   |   | X |   |   |
| 40 | 16i |   | X | X |   |   |   |   | X |   |   |   | X |   |   |   |   |   | X |   |   |
| 46 | 16i |   | X | X |   |   |   |   | X |   |   |   |   |   |   | X |   | X |   |   |   |
| 38 | 16i |   | X | X |   |   |   |   | X |   |   |   |   |   |   | X |   | X |   |   |   |
| 308 | 16j |   | X |   |   | X |   |   | X |   |   |   | X |   |   |   |   | X |   |   |   |
| 309 | 16j |   | X |   |   | X |   |   | X |   |   |   | X |   |   |   |   |   | X |   |   |
| 45 | 16i |   | X |   |   | X |   |   | X |   |   |   |   |   |   | X |   | X |   |   |   |
| 37 | 16i |   | X |   |   | X |   |   | X |   |   |   |   |   |   | X |   | X |   |   |   |
| 258 | 16f |   | X |   |   |   |   |   |   |   |   |   |   |   |   |   |   |   |   |   |   |
| 259 | 16e |   |   | X | X | X |   |   | X |   |   |   |   |   |   |   |   |   |   |   |   |
| 259 | 16e |   |   | X | X | X |   |   | X |   |   |   |   |   |   |   |   |   |   |   |   |
| 260 | 16b |   |   | X | X | X |   |   |   |   |   |   |   |   |   |   |   |   |   |   |   |
| 260 | 16e |   |   | X | X | X |   |   |   |   |   |   |   |   |   |   |   |   |   |   |   |
| 260 | 16e |   |   | X | X | X |   |   |   |   |   |   |   |   |   |   |   |   |   |   |   |
| 261 | 16e |   |   | X | X |   |   |   | X |   |   |   |   |   |   |   |   |   |   |   |   |
| 261 | 16e |   |   | X | X |   |   |   | X |   |   |   |   |   |   |   |   |   |   |   |   |
| 262 | 16e |   |   | X | X |   |   |   |   |   |   |   |   |   |   |   |   |   |   |   |   |
| 54 | 16i |   |   | X |   | X |   |   | X |   |   |   | X |   |   |   |   | X |   |   |   |
| 54 | 16i |   |   | X |   | X |   |   | X |   |   |   | X |   |   |   |   | X |   |   |   |
| 52 | 16i |   |   | X |   | X |   |   | X |   |   |   | X |   |   |   |   |   | X |   |   |
| 52 | 16i |   |   | X |   | X |   |   | X |   |   |   | X |   |   |   |   |   | X |   |   |
| 51 | 16i |   |   | X |   | X |   |   | X |   |   |   |   |   |   | X |   | X |   |   |   |
| 51 | 16i |   |   | X |   | X |   |   | X |   |   |   |   |   |   | X |   | X |   |   |   |
| 49 | 16i |   |   | X |   | X |   |   | X |   |   |   |   |   |   | X |   |   | X |   |   |
| 49 | 16i |   |   | X |   | X |   |   | X |   |   |   |   |   |   | X |   |   | X |   |   |
| 263 | 16e |   |   | X |   | X |   |   | X |   |   |   |   |   |   |   |   |   |   |   |   |
| 263 | 16e |   |   | X |   | X |   |   | X |   |   |   |   |   |   |   |   |   |   |   |   |
| 264 | 16e |   |   | X |   | X |   |   |   |   |   |   |   |   |   |   |   |   |   |   |   |
| 36 | 16i |   |   | X |   |   |   |   | X |   |   |   | X |   |   |   | X | X |   |   |   |
| 28 | 16i |   |   | X |   |   |   |   | X |   |   |   | X |   |   |   | X |   | X |   |   |
| 314 | 16j |   |   | X |   |   |   |   | X |   |   |   | X |   |   |   |   | X | X |   |   |
| 12 | 16i |   |   | X |   |   |   |   | X |   |   |   | X |   |   |   |   | X |   |   | X |
| 16 | 16i |   |   | X |   |   |   |   | X |   |   |   | X |   |   |   |   |   | X | X |   |
| 16 | 16i |   |   | X |   |   |   |   | X |   |   |   | X |   |   |   |   |   | X | X |   |
| 317 | 16j |   |   | X |   |   |   |   | X |   |   |   | X |   |   |   |   |   | X |   | X |
| 34 | 16i |   |   | X |   |   |   |   | X |   |   |   |   |   |   | X | X | X |   |   |   |
| 26 | 16i |   |   | X |   |   |   |   | X |   |   |   |   |   |   | X | X |   | X |   |   |
| 320 | 16j |   |   | X |   |   |   |   | X |   |   |   |   |   |   | X |   | X | X |   |   |
| 10 | 16i |   |   | X |   |   |   |   | X |   |   |   |   |   |   | X |   | X |   |   | X |
| 10 | 16i |   |   | X |   |   |   |   | X |   |   |   |   |   |   | X |   | X |   |   | X |
| 322 | 16j |   |   | X |   |   |   |   | X |   |   |   |   |   |   | X |   |   | X | X |   |
| 2 | 16i |   |   | X |   |   |   |   | X |   |   |   |   |   |   | X |   |   | X |   | X |
| 2 | 16i |   |   | X |   |   |   |   | X |   |   |   |   |   |   | X |   |   | X |   | X |
| 266 | 16f |   |   | X |   |   |   |   |   |   |   |   |   |   |   |   |   |   |   |   |   |
| 267 | 16h |   |   |   | X | X |   |   |   |   |   |   |   |   |   |   |   |   |   |   |   |
| 268 | 16h |   |   |   | X |   |   |   | X |   |   |   |   |   |   |   |   |   |   |   |   |
| 269 | 16c |   |   |   | X |   |   |   |   |   |   |   |   |   |   |   |   |   |   |   |   |

TABLE 5-continued

Additional phage combinations

| Combination number | FIG. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| 35 | 16i | | | | | X | | | X | | | | X | | | | X | X | | | |
| 27 | 16i | | | | | X | | | X | | | | X | | | | X | | X | | |
| 333 | 16j | | | | | X | | | X | | | | X | | | | | X | | X | |
| 11 | 16i | | | | | X | | | X | | | | X | | | | | X | | | X |
| 335 | 16j | | | | | X | | | X | | | | X | | | | | | X | X | |
| 3 | 16i | | | | | X | | | X | | | | X | | | | | | X | | X |
| 33 | 16i | | | | | X | | | X | | | | | | | X | X | X | | | |
| 25 | 16i | | | | | X | | | X | | | | | | | X | X | | X | | |
| 339 | 16j | | | | | X | | | X | | | | | | | X | | X | | X | |
| 9 | 16i | | | | | X | | | X | | | | | | | X | | X | | | X |
| 13 | 16i | | | | | X | | | X | | | | | | | X | | | X | X | |
| 342 | 16j | | | | | X | | | X | | | | | | | X | | | X | | X |
| 270 | 16h | | | | | X | | | X | | | | | | | | | | | | |
| 271 | 16f | | | | | X | | | | | | | | | | | | | | | |
| 272 | 16f | | | | | | X | | | | | | | | | | | | | | |
| 273 | 16f | | | | | | | X | | | | | | | | | | | | | |
| 274 | 16h | | | | | | | | X | | | | | | | | | | | | |
| 275 | 16f | | | | | | | | | X | | | | | | | | | | | |

Example 15: In Vivo Study to Examine Bacterial Load Reduction by KP2-Specific Phage Cocktail Administered at Different Time Points The bacterial load reduction efficacy of treatment with Composition 1 from Example 14 was explored in mice by studying the cocktail administration at different time points. C57BL/6 mice, 6-8 weeks of age, were utilized. Bacterial colonization of mice intestine was achieved by treatment with a daily antibiotic regimen, for 8 days (n=28 mice). Daily Tylosin (0.5 gr/L) was administered to the mice for 4 days prior to KP2 administration, after which, the mice continued on daily Ampicillin (200 mg/L) for an additional 4 days. The KP2 strain was cultured at a density of $10^{10}$ CFU/mL. 0.1 ml of bacterial suspension, containing $10^9$ CFU was administered to each animal.

The 28 mice were divided into 4 groups of seven. All mice received a single dose of KP2. One group was treated with a phage cocktail, administered daily starting on day 4 post KP2 administration through day 9. Another group, used as the vehicle control for the phage cocktail, was administered the vehicle, starting on day 4 post KP2 administration. Two additional groups were treated with the phage cocktail once, at different time points (day 4 and day 6 post KP2 administration). The phage cocktail was provided in phage buffer at a titer of $5 \times 10^9$ PFU/mL. 0.2 ml of this suspension ($10^9$ phages total) was administered per mouse. Both KP2 and the phage cocktail were administered by oral gavage.

Colonization of KP2 was determined by bacterial load in stool samples, when comparing the experimental and control groups. Stool collection for bacterial counts (CFU/gr) was carried out on day−4, daily from days 0 to 5 and on days 7 to 9. The study was terminated 10 days post KP2 administration. Intestines were collected from all mice for CFU counts. Intestines were weighed and put in PBS, at 0° C. for mucosal CFU determination.

The stools were processed for KP2 bacterial count, with approximately 50 mg of stool collected and weighed from each individual mouse. The stool was suspended in 5 mL PBS and a stomacher was used. A 1 mL sample was transferred into an Eppendorf tube and centrifuged for 5 min at 2,000×g. The pellet was re-suspended with 1 mL PBS and centrifuged for 5 min, at 2,000×g. The supernatant was discarded and the procedure repeated. Next, the stool pellet was re-suspended with 1 mL PBS and diluted in a 4-fold dilution series (7 times).

Each diluted sample (5 μL) was added to BHIS (Brain Heart Infusion Salt) agar plates supplemented with 4 antibiotics (selective plates for KP2). Plates were incubated at 37° C. for 24 hours, and KP2 colonies were counted for all samples. The number of colony forming units was calculated per gram of stool sample (no. colonies×dilution×200× 1000/X mg to have CFU/gr stool). At termination, animals were sacrificed, and their intestines were harvested, weighed and processed for CFU counts as described for stool samples.

Figure 4:
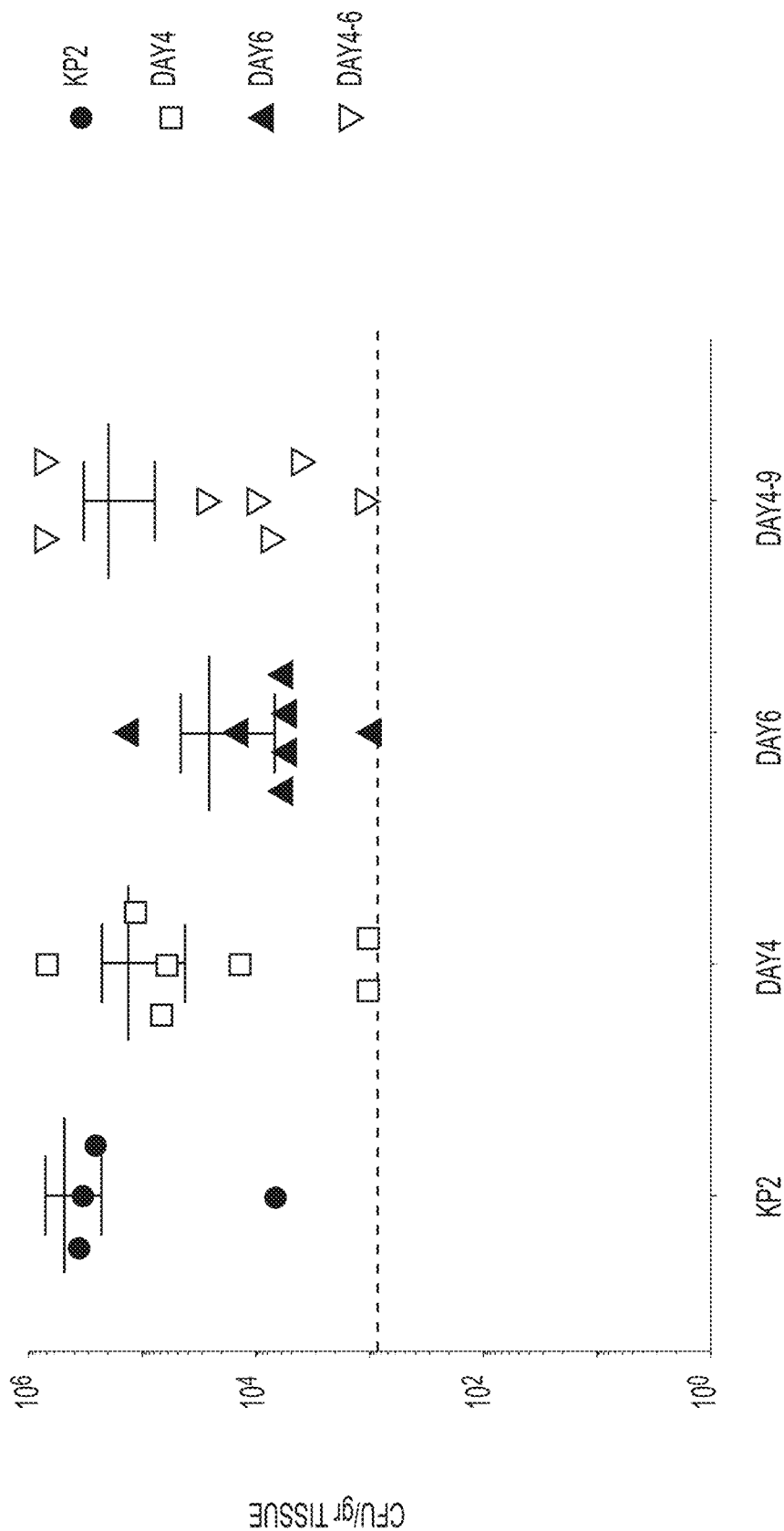
FIG. 4 shows KP2 CFU in mucosa for four groups of mice: 1) vehicle control administered daily starting on day 4 post KP2 administration (KP2); 2) a single dose of phage cocktail administered on day 4 post KP2 administration (Day 4); 3) daily phage cocktail doses administered starting on day 4 post KP2 administration (Day 4-6); 4) a single dose of phage cocktail administered on day 6 post KP2 administration (Day 6). The dashed line represents the limit of detection ($10^3$ CFU/g tissue).

As seen in FIG. 3, some reduction in bacterial load was observed in the stool of all treated animals compared to control. This was the case for all administration regimens. The reduction in comparison with control was more apparent when the mucosal associated bacterial load was examined (FIG. 4.) and appeared to be greatest for animals treated with phage on day 6.

Example 16: In Vivo Study to Determine Treatment Efficacies of KP2-Specific Phage Cocktails with Different Compositions The bacterial load reduction efficacy of compositions 1, 2 and 3 from Example 14 was studied by administrating different regimens, once or multiple times at 3 day intervals. C57BL/6 mice, 6-8 weeks of age, were utilized. Bacterial colonization of mice intestine was achieved by treatment with a daily antibiotic regimen, for 8 days (n=30 mice). Daily Tylosin (0.5 gr/L) was administered to the mice for 4 days prior to KP2 administration, after which, the mice continued on daily Ampicillin (200 mg/L) for an additional 4 days.

The 30 mice were divided into 5 groups of six. All mice were administered a single dose of KP2. Two groups were treated with one composition of phage cocktail (tested in the above in vivo study). One group received the cocktail once, and the second group received it 3 times, on days 6, 9 and 12. Two additional groups received other compositions of phage cocktails, 3 times, on days 6, 9 and 12. The residual colonization of KP2 was determined by the bacterial load in stool samples. The bacterial load in the experimental groups was compared with that of the control group receiving vehicle 3 times, on days 6, 9 and 12. CFU/gr was measured for stool 5 times after phage administration and at study termination.

KP2 strain was cultured at a density of $10^{10}$ CFU/mL. 0.1 ml of bacterial suspension containing $10^9$ CFU was administered to each animal. The study was terminated 14 days post KP2 administration. Intestines and stool were collected from all mice for CFU count. Intestines were weighed and put in PBS, at 0° C. for mucosal CFU determination.

KP2 specific phage cocktails were provided at the following titers: Composition 1: $5 \times 10^9$ PFU/mL, 200 μL of this suspension ($10^9$ phages total) per mouse. Composition 2: $6.3 \times 10^9$ PFU/mL, 200 μL of this suspension ($1.2 \times 10^9$ phages total) per mouse. Composition 3: $7.6 \times 10^9$ PFU/mL, 200 μL of this suspension ($1.5 \times 10^9$ phages total) per mouse. 0.2 ml of the vehicle (phage buffer) was administered per mouse At termination, animals were sacrificed, and their intestines were harvested., weighed and processed for CFU counts as described for stool samples.

Figure 5:
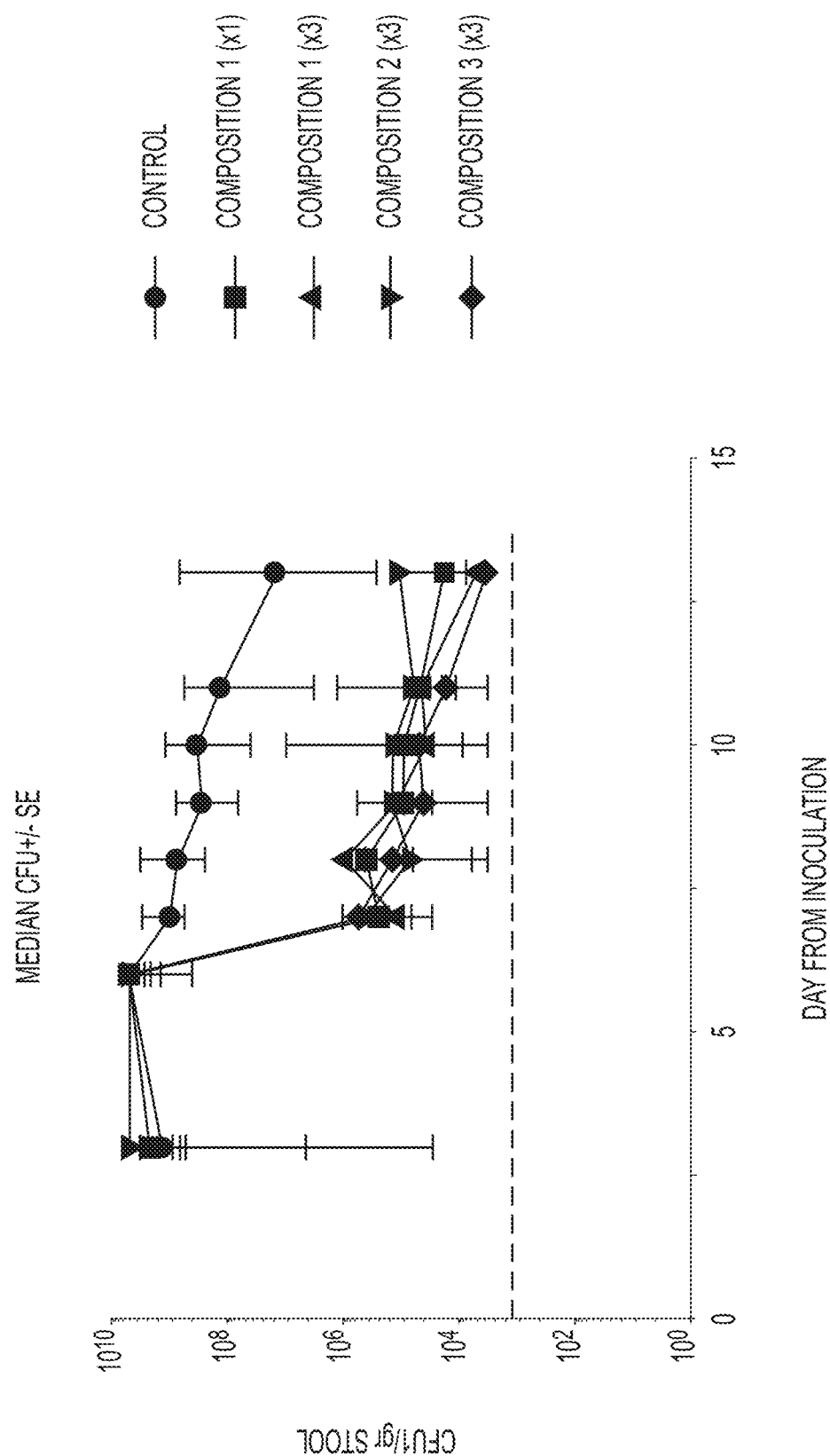
FIG. 5 shows KP2 CFU in stool for five groups of mice: 1) Control; 2) Composition 1 (1.2-2, 1.2-3s, 1.2-3b), administered once; 3) Composition 1, administered 3 times on days 6, 9 and 12 post KP2 administration; 4) Composition 2 (1.2-2, 1.2-3s, 1.2-3b, MCoc5c), administered 3 times on days 6, 9 and 12 post KP2 administration; 5) Composition 3 (1.2-2, 1.2-3s, 1.2-3b, MCoc5c, 8M-1), administered 3 times on days 6, 9 and 12 post KP2 administration. The dashed line represents the limit of detection ($10^3$ CFU/g stool).

FIG. 5 shows KP2 CFU in stool for five groups of mice colonized with KP2: 1) Control; 2) Composition 1 (1.2-2, 1.2-3s, 1.2-3b), administered once; 3) Composition 1, administered 3 times on days 6, 9 and 12 post KP2 administration; 4) Composition 2 (1.2-2, 1.2-3s, 1.2-3b, MCoc5c), administered 3 times on days 6, 9 and 12 post KP2 administration; 5) Composition 3 (1.2-2, 1.2-3s, 1.2-3b, MCoc5c, 8M-1), administered 3 times on days 6, 9 and 12 post KP2 administration. The dashed line represents the limit of detection ($10^3$ CFU/g stool).

As also seen in FIG. 5, all the phage compositions and administration protocols induced a significant log reduction in bacterial load in the colon. The 5 phage cocktail performed the best in reducing the bacterial load in the colon as measured by CFU/gr stool and reached a level below the limit of detection (1000 CFU KP2/g stool) by the end of the study on Day 13. This is also seen in Table 6 below which shows the CFU values per gram of stool for individual mice in groups 1M to 5M at the time of termination of the study along with average and median values. While a single administration of Composition 1 (Group 2M) brought about a large reduction in stool bacterial load relative to the untreated animals, the reduction was even greater following 3 administrations of the same phage cocktail (Group 3 M). Three administrations of Composition 3 (Group 5 M) resulted in a bacterial load below the level of detection (1000 CFU KP2/g stool, shown here as 0) for all the animals treated with this composition.

TABLE 6

| | mouse no. | day 13 |
|---|---|---|
| 1M Control | 1 | 4.1E+08 |
| | 2 | 8.71E+08 |
| | 3 | 3.47E+07 |
| | 4 | 4.98E+06 |
| | 5 | 3.19E+05 |
| | 6 | 1.98E+06 |
| | AVG | 2.21E+08 |
| | Median | 1.98E+07 |
| 2M composition 1 × 1 dose | 7 | 1.02E+05 |
| | 8 | 1.83E+04 |
| | 9 | 0E+00 |
| | 10 | 2.55E+04 |
| | 11 | 3.1E+04 |
| | 12 | 1.11E+04 |
| | AVG | 3.14E+04 |
| | Median | 2.19E+04 |

TABLE 6-continued

| | mouse no. | day 13 |
|---|---|---|
| 3M composition 1 × 3 dose | 13 | 0E+00 |
| | 14 | 0E+00 |
| | 15 | 0E+00 |
| | 16 | 4.63E+04 |
| | 17 | 3.37E+04 |
| | 18 | 9.58E+03 |
| | AVG | 1.49E+04 |
| | Median | 4.79E+03 |
| 4M composition 2 × 3 dose | 19 | 2.63E+05 |
| | 20 | 2.14E+05 |
| | 21 | 1.94E+05 |
| | 22 | 3.99E+04 |
| | 23 | 2.24E+04 |
| | 24 | 8.76E+03 |
| | AVG | 1.24E+05 |
| | Median | 1.17E+05 |
| 5M composition 3 × 3 dose | 25 | 0E+00 |
| | 26 | 0E+00 |
| | 27 | 0E+00 |
| | 28 | 0E+00 |
| | 29 | 0E+00 |
| | 30 | 0E+00 |
| | AVG | 0E+00 |
| | Median | 0E+00 |

Figure 6:
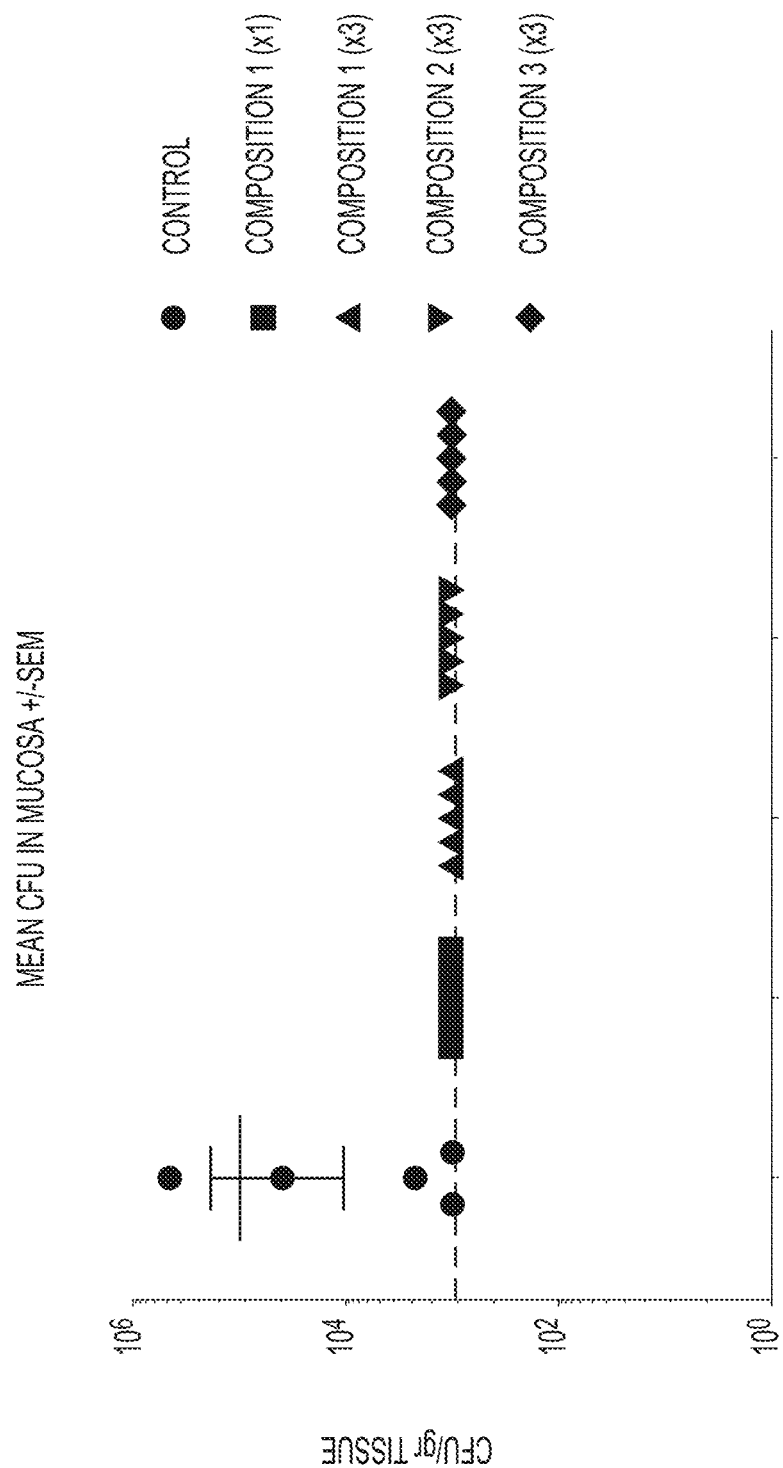
FIG. 6 shows KP2 CFU in mucosa for five groups of mice: 1) Control; 2) Composition 1 (1.2-2, 1.2-3s, 1.2-3b), administered once; 3) Composition 1, administered on days 6, 9 and 12 post KP2 administration; 4) Composition 2 (1.2-2, 1.2-3s, 1.2-3b, MCoc5c), administered on days 6, 9 and 12 post KP2 administration; 5) Composition 3 (1.2-2, 1.2-3s, 1.2-3b, MCoc5c, 8M-1), administered on days 6, 9 and 12 post KP2 administration. The dashed line represents the limit of detection ($10^3$ CFU/g tissue).

FIG. 6 shows KP2 CFU in mucosa for the same five groups of mice: 1) Control; 2) Composition 1 (1.2-2, 1.2-3s, 1.2-3b), administered once; 3) Composition 1, administered on days 6, 9 and 12 post KP2 administration; 4) Composition 2 (1.2-2, 1.2-3s, 1.2-3b, MCoc5c), administered on days 6, 9 and 12 post KP2 administration; 5) Composition 3 (1.2-2, 1.2-3s, 1.2-3b, MCoc5c, 8M-1), administered on days 6, 9 and 12 post KP2 administration. The dashed line represents the limit of detection ($10^3$ CFU/g tissue). As seen in FIG. 6, all 3 compositions and treatment regimens resulted in a reduction of bacterial load in the mucosa to below detection limit (1000 CFU KP2/g stool).

Example 17: In Vivo Study to Determine Efficacy of Phage Cocktails with 3, 4 and 5 KP2-Specific Phages on a KP2 Clinical Variant In order to verify the efficacy in vivo of the KP2 phage on KP2 clinical variants, the efficacy of phage cocktails, containing 3 to 5 phage was tested on mice colonized with the KP2 clinical variant CT-141-1.

Phage cocktails consisted of the following phage:
Composition 1 (comp 1) phages Mcoc-5c, 8M-7, 1.2-3b;
Composition 2 (comp 2) phages Mcoc-5c, 8M-7, 1.2-2, 1.2-3s;
Composition 3 (comp 3) phages Mcoc-5c, 8M-7, 1.2-2, 1.2-3b Composition 4 (comp 4) phages Mcoc-5c, 8M-7, KP2-5-1, 1.2-3s, PKP-55; and
Composition 5 (comp 5) phages Mcoc-5c, 8M-7, 1.2-2, 1.2-3s, 1.2-3b Bacterial colonization with CT-141-1 was achieved by treatment with a daily antibiotic regimen, for 8 days (n=30 mice). Daily Tylosin (0.5 gr/L) was administered to the mice for 4 days prior to KP2 administration, after which, the mice continued on daily Ampicillin (200 mg/L) for an additional 4 days.

C57BL/6 mice, 6-8 weeks of age, were utilized. Mice were divided into 6 groups of five. All groups were administered a single dose of the KP2 clinical variant CT-141-1 ($10^9$ CFU/mouse).

Group 1 served as a control and was treated with the vehicle of the phage cocktail on days 6, 9 and 12 after CT-141-1 administration. Group 2 received composition 1 on days 6, 9, and 12. Group 3 received composition 2 on days 6, 9 and 12. Group 4 received composition 3 on days 6, 9 and 12. Group 5 received composition 4 on days 6, 9 and 12. Group 6 received composition 5 on days 6, 9 and 12. All treatments were administered by oral gavage.

The KP2 clinical variant was cultured at a density of $10^{10}$ CFU/mL. 0.1 ml of bacterial suspension, containing $10^9$ CFU, was administered to each animal by oral gavage.

Stool was collected daily from day 6, including at termination (except on day 12). The study was terminated 14 days post KP2 clinical strain administration. Intestines were collected from all mice for CFU determination. Intestines were weighed and put in PBS, at 0° C., for mucosal CFU determination.

Phage cocktails were formulated in phage buffer (50 mM Tris-HCl, 100 mM NaCl, 5 mM $MgCl_2$, 0.1 mM $MnCl_2$ pH=7.5). 0.2 ml of the vehicle or phage was administered per mouse, All phage compositions were at a concentration of $5\times10^9$ PFU/mL, and 200 μL of this suspension ($10^9$ PFU total) was administered per mouse at each administration point. At termination, animals were sacrificed and their intestines were harvested, weighed and processed for CFU counts as described for stool samples.

The residual colonization of CT-141-1 was determined by the bacterial load in stool samples. The bacterial load in the experimental and control groups, receiving KP2-specific phage cocktails or vehicle on days 6, 9 and 12, were compared.

Figure 7:
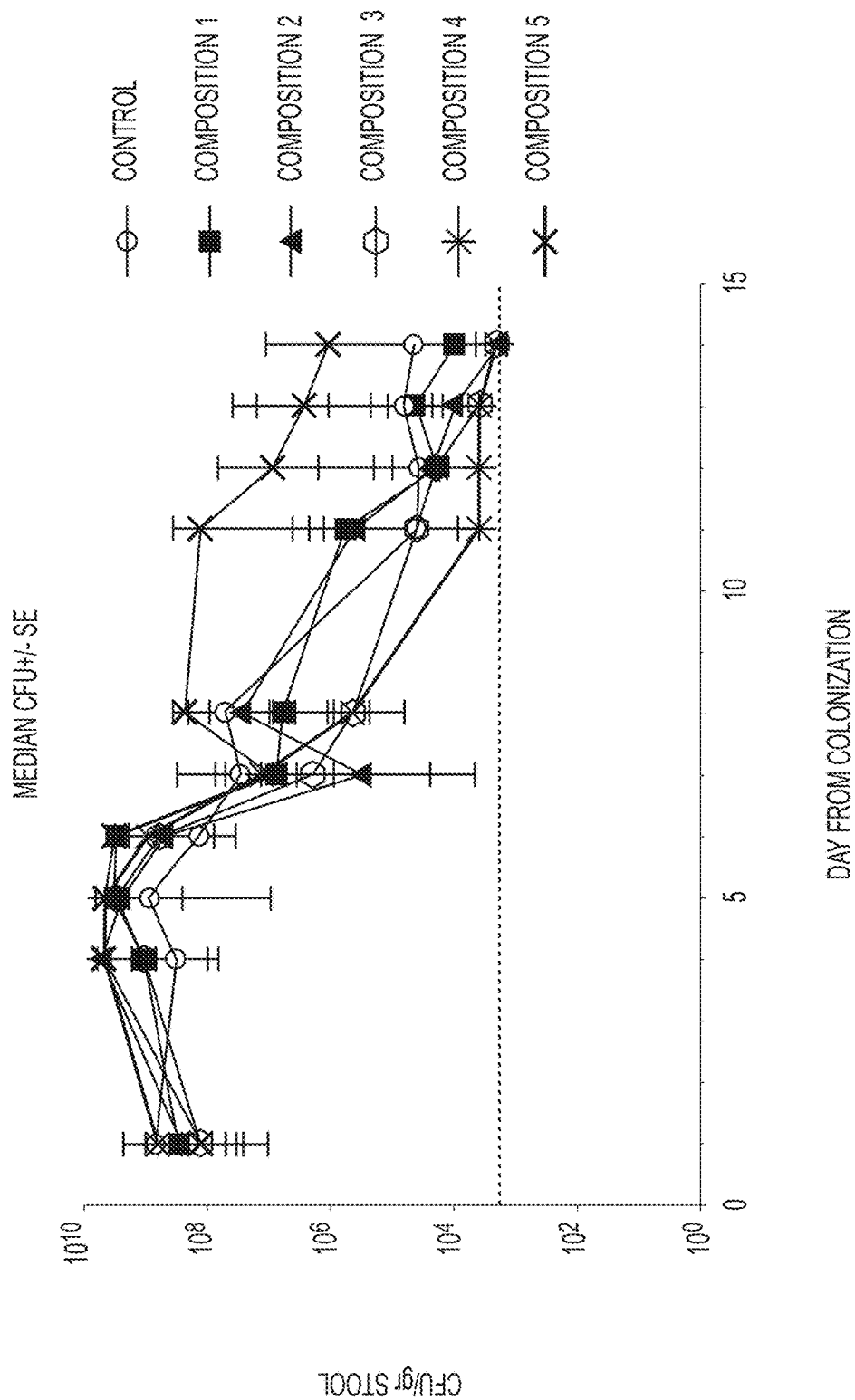
FIG. 7 shows CT-141-1 CFU ratio of treated/control in stool for the five groups of mice who received: 1) Composition 1 (Mcoc-5c, 8M-7, 1.2-3b); 2) Composition 2 (Mcoc-5c, 8M-7, 1.2-2, 1.2-3s); 3) Composition 3 (Mcoc-5c, 8M-7, 1.2-2, 1.2-3b); 4) Composition 4 (Mcoc-5c, 8M-7, KP2-5-1, 1.2-3s, PKP-55); 5) Composition 5 (Mcoc-5c, 8M-7, 1.2-2, 1.2-3s, 1.2-3b). All compositions were administered on days 6, 9 and 12 post KP2 administration. The dashed line represents the ratio of the two values equaling 1.

FIG. 7 shows CT-141-1 CFU ratio of treated/control in stool for the five groups of mice who received: 1) Composition 1 (Mcoc-5c, 8M-7, 1.2-3b); 2) Composition 2 (Mcoc-5c, 8M-7, 1.2-2, 1.2-3s); 3) Composition 3 (Mcoc-5c, 8M-7, 1.2-2, 1.2-3b); 4) Composition 4 (Mcoc-5c, 8M-7, KP2-5-1, 1.2-3s, PKP-55); 5) Composition 5 (Mcoc-5c, 8M-7, 1.2-2, 1.2-3s, 1.2-3b). All compositions were administered on days 6, 9 and 12 post KP2 administration. The dashed line represents the ratio of the two values equaling 1.

As seen in FIG. 7, while compositions 1 and 5 led to little or no reduction in bacterial load as compared to the control mice, treatment of the CT-141-1 colonized mice with compositions 2, 3 or 4 led to a 2 log reduction in the stool bacterial load by the end of the study period (FIG. 7).

Figure 8:
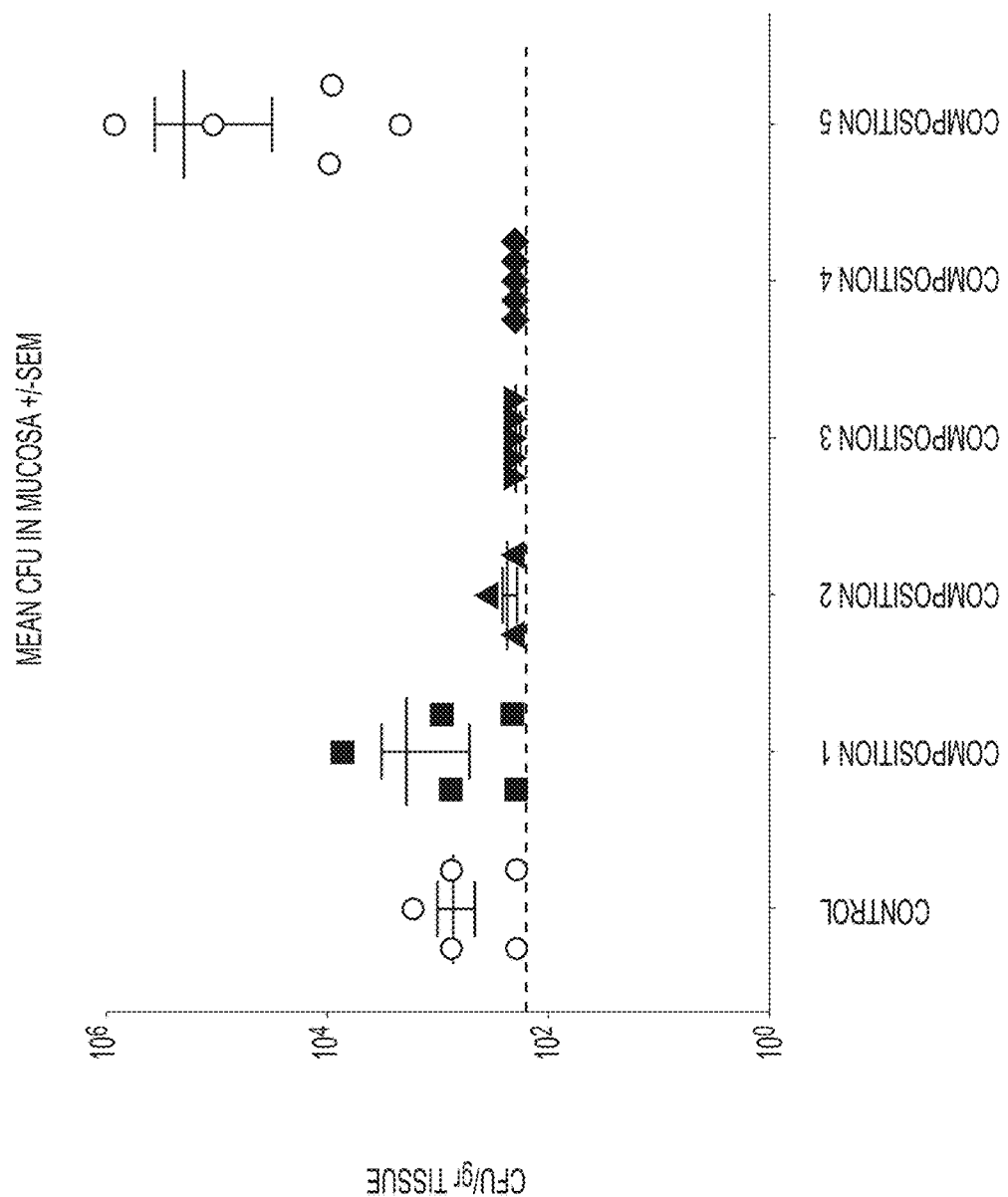
FIG. 8 shows CFU in mucosa of the five groups of mice who received: 1) Composition 1 (Mcoc-5c, 8M-7, 1.2-3b); 2) Composition 2 (Mcoc-5c, 8M-7, 1.2-2, 1.2-3s); 3) Composition 3 (Mcoc-5c, 8M-7, 1.2-2, 1.2-3b); 4) Composition 4 (Mcoc-5c, 8M-7, KP2-5-1, 1.2-3s, PKP-55); 5) Composition 5 (Mcoc-5c, 8M-7, 1.2-2, 1.2-3s, 1.2-3b). All compositions were administered on days 6, 9 and 12 post KP2 administration. The dashed line represents the limit of detection ($10^3$ CFU/g tissue).

The same compositions were effective in reducing bacterial load in the mucosa as seen in FIG. 8, that shows CFU in mucosa of the five groups of mice who received: 1) Composition 1 (Mcoc-5c, 8M-7, 1.2-3b); 2) Composition 2 (Mcoc-5c, 8M-7, 1.2-2, 1.2-3s); 3) Composition 3 (Mcoc-5c, 8M-7, 1.2-2, 1.2-3b); 4) Composition 4 (Mcoc-5c, 8M-7, KP2-5-1, 1.2-3s, PKP-55); 5) Composition 5 (Mcoc-5c, 8M-7, 1.2-2, 1.2-3s, 1.2-3b). All compositions were administered on days 6, 9 and 12 post KP2 administration. The dashed line represents the limit of detection ($10^3$ CFU/g tissue). For all of these three phage cocktails, the levels of CFU in the mucosa were reduced to below the LOD while detectable levels were observed following treatment with compositions 1 or 5. Thus, Compositions 2, 3 and 4 are particularly effective in reducing bacterial load of CT-141-1 in colonized mice.

Example 18: Biofilm Reduction Capabilities of KP2 Phages

To examine phage ability to penetrate KP2 biofilms and reduce the number of viable bacteria found within, KP2 was grown at 37° C. with agitation to $OD_{600}$ 1.5 and diluted in LB medium supplemented with 1% glucose to $OD_{600}$ 0.1.

For biofilm formation, 200 μl of the resulting culture was added to 96 well plates and incubated for 24 hrs at 37° C., which enabled growth to approximately $4\times10^8$ cells per well. 180 μl was discarded to remove planktonic cells and 50 μl of the individual phages (1.2-3b, 1.2-3s, 1.2-2, 8M-1) or one of the three cocktails (Composition 1, 2 and 3) as detailed in Example 14 was applied at a MOI of 0.01 ($4\times10^6$ total phage particles). Phage buffer was added to untreated wells as a negative control. 150 μl of LB supplemented with 1% glucose and 1 mM MMC ions was added and incubated at 37° C. At set time points, the liquid was removed, and the biofilm was scraped rigorously from the bottom of the wells. 100 μl PBS was added to the wells, mixed and moved to sterile eppendorfs with 900 μl PBS. Samples were vortexed for 1 minute and washed 3 times by centrifuging at 4° C. for 5 minutes at 6000×g. After the last wash, 200 μl of PBS was added and samples were serially diluted by 10 fold in PBS. A 5 μl drop of each dilution was plated on BHIS agar plates. Plates were incubated overnight at 37° C. after which bacteria concentration was determined by viable count.

Figure 12:
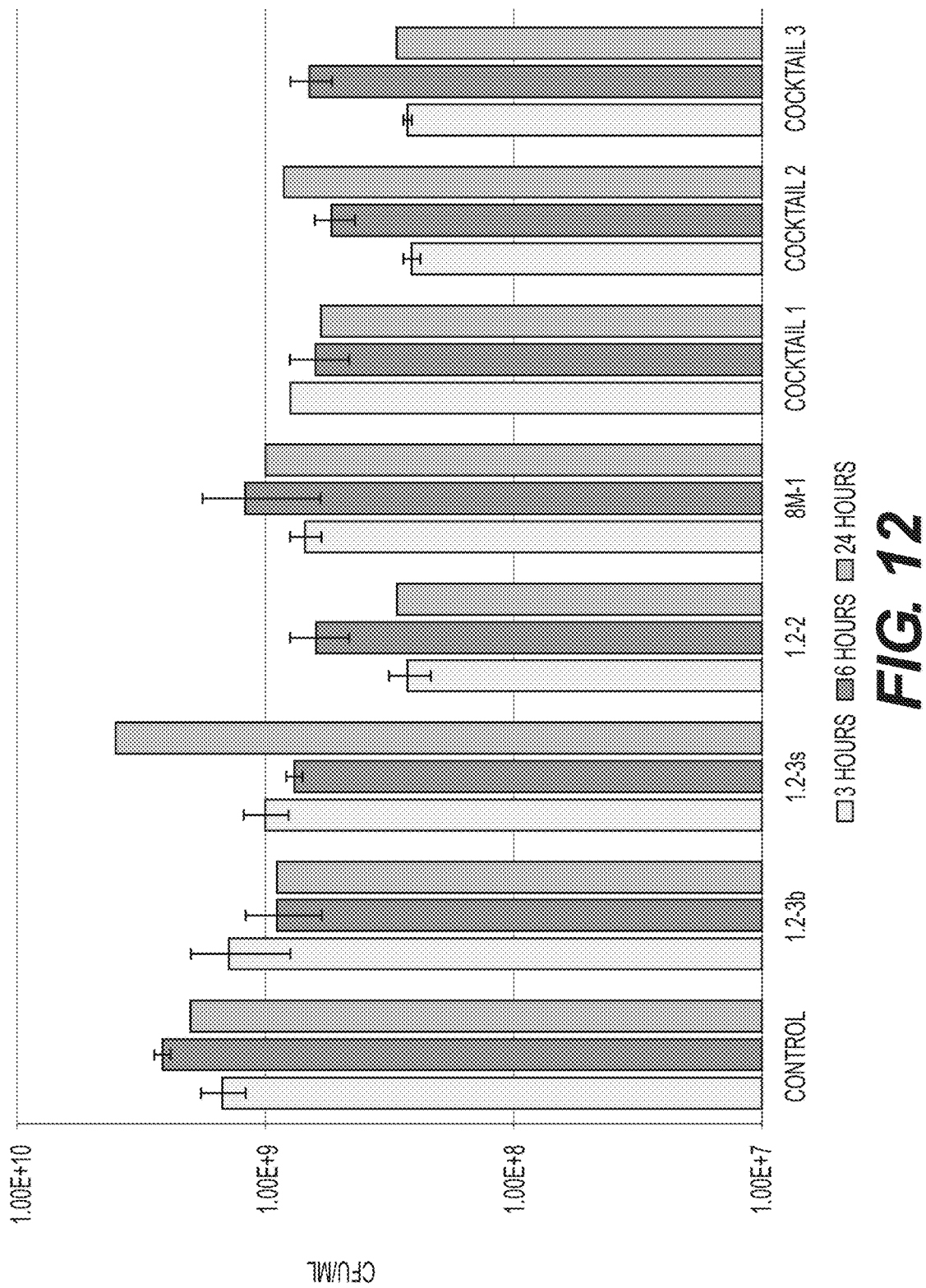
FIG. 12 shows CFU counts post phage treatment of KP2 biofilm in multiwell biofilm assay, with control, various individual phage or phage cocktails.
Figure 13:
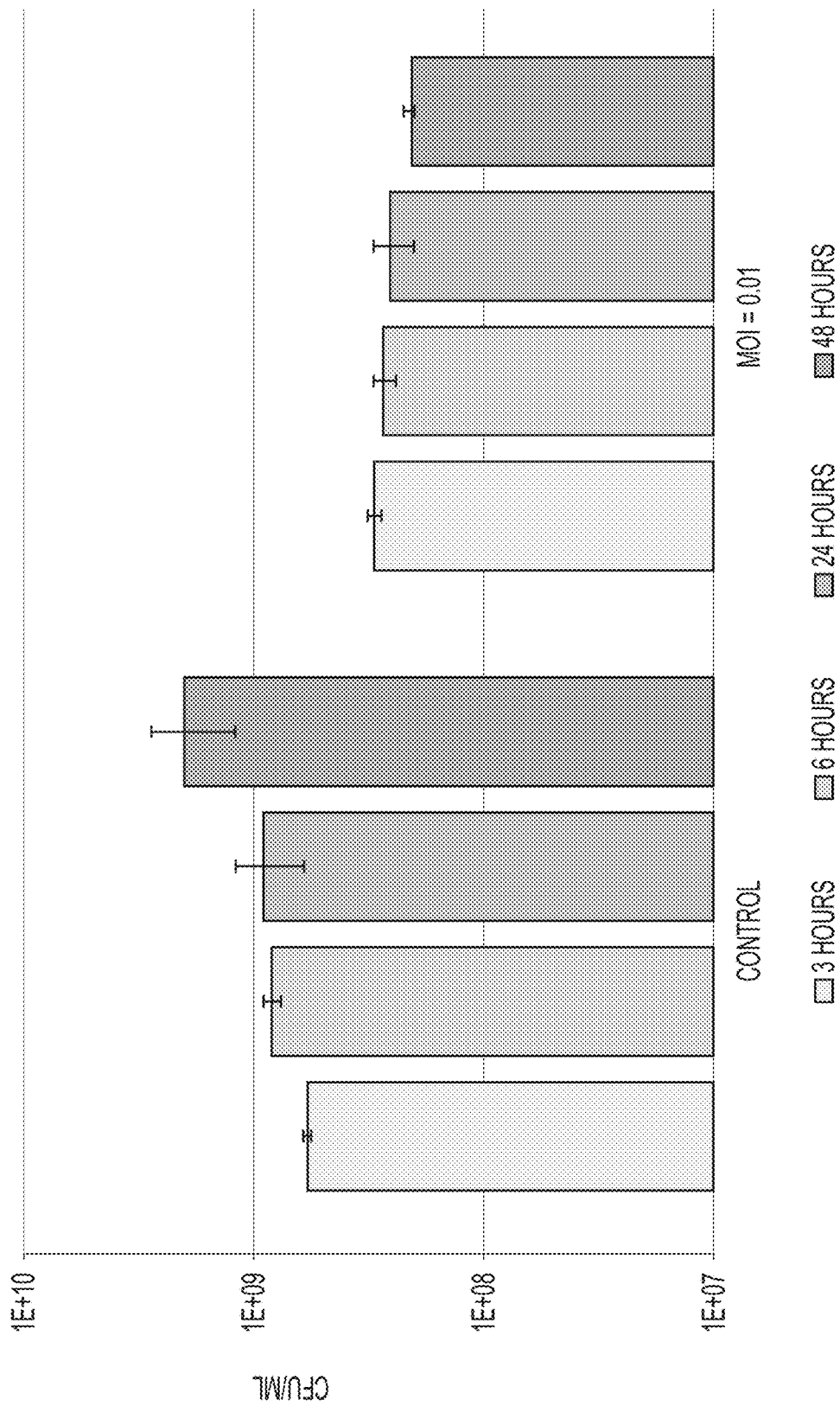
FIG. 13 shows CFU counts post phage 1.2-2 treatment of KP2 biofilm in multiwell biofilm assay.

FIG. 12 shows CFU counts post phage treatment of KP2 biofilm. Of the individual phage, phage 1.2-2 showed the greatest activity on biofilm with nearly a 1 log reduction in CFU counts as compared to the control after a treatment period of 24 hours. A similar almost 1 log reduction at this time point was also observed with Cocktail 3. Similar results The individual phage 1.2-3b and 8M-1 gave weaker results, as did Cocktails 1 and 2. In a subsequent experiment focusing on phage 1.2-2 and in which the treatment period was extended to 48 hours (FIG. 13), a full one log reduction in viable bacteria extracted from biofilm was observed after phage treatment for 48 hours.

Example 19: Compiling Phage Cocktails for Optimized Infectivity Performance

The phage or phage cocktail's infection of a bacterial host ("infectivity profile") may be characterized by different aspects. Among those aspects are the infected host range, i.e. the range of different hosts the phage can infect, the effect of the cocktail on the growth rate of the host population as examined at a certain time point from first mix of phage and host in vitro (as can be measured e.g. by $OD_{600}$ due to lysis of bacterial cells in vitro) and the elongation of the time to the appearance of phage resistant mutants (Time to Mutant or TTM). The phage disclosed above may be combined to form cocktails with improved infectivity profile, at least for one characteristic, compared to the infectivity profile of each member phage alone. In this example, the method of compiling cocktails with expected improved infectivity profile is demonstrated. Those cocktails may then be tested in vitro and in vivo according to the experimental methods detailed above.

In certain embodiments, it is wished to produce a cocktail with longer time to mutant (TTM) with relation to certain host, compared to each member phage. For example, referring to FIG. 1, in case it is desired to compile a cocktail with longer TTM for KP2, different combinations of phage are elected from the group of phage discovered to infect KP2. Such resulting cocktails are further detailed in Example 14 where cocktails with improved TTM are achieved.

Genetically diverse phage that infect the same host may utilize different attack mechanisms (Bertozzi et. al, 2016) and therefore, according to certain embodiments, the candidate cocktails are created by electing member phage that are likely to differ in their mechanism of action because they belong to different taxonomical groups. For example, as was further detailed in Example 14, a cocktail based on combination of the three phage 1.2-3s, 1.2-3b, and 1.2-2 from groups PAT, MTK, ST, respectively was found to prevent the appearance of mutants for at least 20 hours and outperform the TTM of each member phage alone. According to certain embodiments, the candidate cocktails are created by electing member phage having relatively distant genomic sequence. In some embodiments, the BLAST cutoff for % identity between each two members is no more than about 0%, 10%, 20%, 30%, 40% or 50%. For example, referring to FIG. 2. And to the cocktail based on combination of the three phage 1.2-3s, 1.2-3b, and 1.2-2, the % identity between each two members are essentially 0%. According to certain embodiments, the candidate cocktails are created by electing member phage with different mechanism of action, having different corresponding bacterial host surface proteins, as further detailed in example 12.

In certain embodiments, it is wished to produce a cocktail with extended host range compared to each member phage. For example, referring to FIG. 1, it may be desired to compile a cocktail that infects both CT-141-1 and MKP2_251_B. By analyzing the data in FIG. 1, two subgroups of phage, one infecting CT-141-1 and the other infecting MKP2_251_B, are defined. The first group includes 10 phage, and the second, 19 phage. Out of the potential 190 combinations to be tested, some are likely to have an improved infectivity profile than others when additional aspects are considered, such as the respective TTM or the decreased host growth rate following infection onset. Such aspects may be measured in liquid dynamic experiments when analyzing the resulting growth curves as presented in FIG. 16a-j.

According to certain embodiments, given the phage disclosed in the present invention, the following steps may be implemented for electing a cocktail: Consider all possible two phage combinations. For example, for a phage collection of 44 specific phage isolates there are ((44×44)−44)/2=946 potential two phage combinations. This number is well suited for high-throughput in vitro assay screening, for example, as detailed in Examples 7 and 14. Moreover, according to certain embodiments, it may be efficient to start by testing representative two phage cocktails that combine the most diverse phage based on taxonomical annotation or genomic sequence % identity. The infectivity performance of the two phage cocktails e.g. with respect to TTM and/or required host range may be compared and best candidates elected. If desired, a third phage member may then be added to leading two phage cocktails. Then, the in vitro screen process is repeated as in the previous round. According to certain embodiments, it may be efficient to compile triplets by adding a third member phage that is the most diverse compare to the already elected two member phage, based on taxonomical annotation or genomic sequence % identity. According to certain embodiments, this process may continue with further rounds of election leading to cocktails with more phage and improved infectivity profile. Eventually the process results in best performing cocktails with varying number of member phage in each. The in vitro testing of such candidate cocktails is demonstrated in Example 14 and 18, and further in vivo testing is demonstrated in Examples 15-17.

Example 20: Targeted Isolation of Phage Based on Known Target Sequence and Available Bacterial Host According to embodiments of the present invention there are provided representative phage sequences, representing phage that are capable of infecting and lysing KP2 variants. Each disclosed phage sequence is a representative of related functionally equivalent phage group having a sequence with homology above 80%, 85%, 90% or 95% identity to the representative phage sequence. In some embodiments, bacteriophages are considered to be "functionally equivalent" as long as they exhibit similar phenotypes, e.g., similar host range, similar lytic ability, and/or threshold sequence similarity (e.g., greater than about 85%, greater than about 90%, greater than about 95%, greater than about 97%, or greater than about 99%).

According to embodiments of the present invention, once the phage with certain sequence is desired it is isolated from an environmental or clinical sample, when the host bacteria (e.g. KP2) is available and the particular desired phage genome sequence is known (e.g. KP2-4a). According to some embodiments, First, the host bacteria is used to screen the environmental or clinical sample for phage that recognizes the KP2 host strain e.g. as detailed in Example 3. The genomic sequence of the isolated phage may be retrieved using NGS sequencing as detailed above. According to other embodiments, the isolated phage may be screened using PCR in order to test if the isolated phage genome includes the required sequence. According to certain embodiments, once a close enough genomic sequence is found, additional genomic alternations may be introduced according to methods taught in the prior art such as homologous recombination technique, Bacteriophage Recombineering of Electroporated DNA (BRED). According to certain other embodiments, the desired phage may be produced by synthesizing the genome according to methods taught in the prior art and rebooting the phages using assembled phage genomic DNA via in vitro translation transcription (TXTL) (Yibao chen et. al 2019; Jonghyeon Shin et. al; U.S. Pat. No. 9,617,522, "Tuning Bacteriophage Host Range", Lu et al.)

REFERENCES

1. Abedon, S. T., & Yin, J. (2009). Bacteriophage plaques: theory and analysis. Methods in molecular biology (Clifton, N.J.), 501, 161-74. doi:10.1007/978-1-60327-164-6_17
2. Altschul et al., 1997. Gapped BLAST and PSI-BLAST: a new generation of protein database search programs, Nucleic Acids Res. 25:3389-3402.
3. Atarashi et al., 2017. Ectopic colonization of oral bacteria in the intestine drives TH1 cell induction and inflammation. Science, 358(6361):359-365.
4. Baym et al. (2015. Inexpensive multiplexed library preparation for megabase-sized genomes. PLoS ONE, 10(5), 1-15)
5. Bertozzi Silva, J., Storms, Z., & Sauvageau, D. (2016). Host receptors for bacteriophage adsorption. *FEMS Microbiology Letters*, 363(4). https://doi(dot)org/10.1093/femsle/fnw002
6. Y. Chen et al., Dysbiosis of small intestinal microbiota in liver cirrhosis and its association with etiology. Scientific reports 6, 34055 (Sep. 30, 2016).
7. Cole et al. 2014. Ribosomal Database Project: data and tools for high throughput rRNA analysis Nucl. Acids Res. 42:D633-D642
8. A. Davin-Regli, J. M. Pages, *Enterobacter aerogenes* and *Enterobacter cloacae*; versatile bacterial pathogens confronting antibiotic treatment. Frontiers in microbiology 6, 392 (2015).
9. Diene et al. The rhizome of the multidrug-resistant *Enterobacter aerogenes* genome reveals how new "killer 10. D. Gevers et al., The treatment-naive microbiome in new-onset Crohn's disease. Cell host & microbe 15, 382 (Mar. 12, 2014).
11. J. H. Grose et al., Understanding the enormous diversity of bacteriophages: the tailed phages that infect the bacterial family Enterobacteriaceae. Virology 0, 421 (November 2014).
12. K. E. Holt et al., Genomic analysis of diversity, population structure, virulence, and antimicrobial resistance in *Klebsiella pneumoniae*, an urgent threat to public health. Proceedings of the National Academy of Sciences of the United States of America 112, E3574 (Jul. 7, 2015).
13. Hyman, P., & Abedon, S. T. (2010). Bacteriophage host range and bacterial resistance. Advances in applied microbiology (1st ed., Vol. 70, pp. 217-48). Elsevier Inc. doi:10.1016/50065-2164(10)70007-1
14. Kazutaka Katoh, Daron M. Standley; MAFFT Multiple Sequence Alignment Software Version 7: Improvements in Performance and Usability. Mol Biol Evol 2013; 30 (4): 772-780
15. Kutter, E. (2009). Phage host range and efficiency of plating. Methods in molecular biology (Clifton, N.J.), 501, 141-9. doi:10.1007/978-1-60327-164-6_14
16. C. A. Lozupone et al., Alterations in the gut microbiota associated with HIV-1 infection. Cell host & microbe 14, 329 (Sep. 11, 2013).
17. S. Mondot et al., Highlighting new phylogenetic specificities of Crohn's disease microbiota. Inflammatory bowel diseases 17, 185 (January, 2011).
18. E. G. Pamer, Resurrecting the intestinal microbiota to combat antibiotic-resistant pathogens. Science 352, 535 (Apr. 29, 2016).
19. N. Qin et al., Alterations of the human gut microbiome in liver cirrhosis. Nature 513, 59 (Sep. 4, 2014).
20. Altschul, S. (1990) Basic Local Alignment Search Tool. J. Mol. Biol.
21. Bankevich, A., Nurk, S., Antipov, D., et al. (2012) SPAdes: a new genome assembly algorithm and its applications to single-cell sequencing. J. Comput. Biol., 19, 455-477.
22. Diancourt, L., Passet, V., Verhoef, J., Grimont, P. A. D. and Brisse, S. (2005) Multilocus sequence typing of *Klebsiella pneumoniae* nosocomial isolates. J. Clin. Microbiol., 43, 4178-4182.
23. Jain, C., Rodriguez-R, L. M., Phillippy, A. M., Konstantinidis, K. T. and Aluru, S. (2018) High throughput ANI analysis of 90K prokaryotic genomes reveals clear species boundaries. Nat. Commun., 9, 5114.
24. Martin, M. (2011) Cutadapt removes adapter sequences from high-throughput sequencing reads. EMBnet. J., 17, 10-12.
25. Ondov, B. D., Treangen, T. J., Melsted, P., Mallonee, A. B., Bergman, N. H., Koren, S. and Phillippy, A. M. (2016) Mash: Fast genome and metagenome distance estimation using MinHash. Genome Biol.
26. Yibao Chen, Himanshu Batra, Junhua Dong, Cen, Venigalla B. Rao and Pan Tao1. Genetic Engineering of Bacteriophages Against Infectious Diseases. Front. Microbiol., 3 May 2019.
27. Jonghyeon Shin, Paul Jardine, Vincent Noireaux. Genome Replication, Synthesis, and Assembly of the Bacteriophage T7 in a Single Cell-Free Reaction. ACS Synthetic Biology 2012 1 (9), 408-413
28. H. S. Said et al., Dysbiosis of salivary microbiota in inflammatory bowel disease and its association with oral immunological biomarkers. DNA research: an international journal for rapid publication of reports on genes and genomes 21, 15 (February, 2014).
29. C. L. Sears, W. S. Garrett, Microbes, microbiota, and colon cancer. Cell host & microbe 15, 317 (Mar. 12, 2014).
30. E. S. Snitkin et al., Tracking a hospital outbreak of carbapenem-resistant *Klebsiella pneumoniae* with whole-genome sequencing. Science translational medicine 4, 148ra116 (Aug. 22, 2012).
31. Y. Taur, E. G. Pamer, The intestinal microbiota and susceptibility to infection in immunocompromised patients. Current opinion in infectious diseases 26, 332 (August, 2013).
32. Tindall et al. *Enterobacter aerogenes* Hormaeche and Edwards 1960 (Approved Lists 1980) and *Klebsiella mobilis* Bascomb et al. 1971 (Approved Lists 1980) share the same nomenclatural type (ATCC 13048) on the Approved Lists and are homotypic synonyms, with consequences for the name *Klebsiella mobilis* Bascomb et al. 1971 (Approved Lists 1980). Int J Syst Evol Microbiol. 2017 February; 67(2):502-504. PubMed PMID: 27902205.
33. I. Vujkovic-Cvijin et al., Dysbiosis of the gut microbiota is associated with HIV disease progression and tryptophan catabolism. Science translational medicine 5, 193ra91 (Jul. 10, 2013).
34. Zhou et al. 2011 PHAST: A Fast Phage Search Tool. Nucl. Acids Res. 39 suppl. 2: W347-W352.
35. U.S. Pat. No. 9,415,079. Composition for inducing proliferation or accumulation of regulatory T cells.

SEQUENCE LISTING

The patent contains a lengthy sequence listing. A copy of the sequence listing is available in electronic form from the USPTO web site (https://seqdata.uspto.gov/?pageRequest=docDetail&DocID=US12390499B2). An electronic copy of the sequence listing will also be available from the USPTO upon request and payment of the fee set forth in 37 CFR 1.19(b)(3).

The invention claimed is:

1. A method of treating an inflammatory bowel disease comprising administering to a subject in need thereof a pharmaceutical composition comprising a pharmaceutically acceptable carrier; and lytic bacteriophages selected from at least three of the following groups:
   a) Group 1: 1.2-2, colon-11, PKP-55, or a family Myoviridae, subfamily Tevenvirinae, genus Kp15 virus that is capable of infecting at least two of *Klebsiella pneumoniae* strains: KP2, CT-123-1, MKP2_21611, and MKP2_251_B;
   b) Group 2: M16-7a, KP2-4a, M16-4a, colon-36, KP2-5-1, 1.2-4br, 1.2-4s, M16-6c, KP2-9a, M16-9a, KP2-5a, colon-14-15, colon-6, colon1, M16-3-2c, M16-5c, or a family Myoviridae, subfamily Tevenvirinae, genus T4 virus that is capable of infecting at least two of *Klebsiella pneumoniae* strains: KP2, CT-123-1, MKP2_2161 1, and MKP2_251_B;
   c) Group 3: KP2-15-2-1, KP2-14, KP2-15-1, colon-14, 1.2-3b, KP2-8c, KP2-7c, KP2-7-1c, KP2-8a, KP2-5, KP2-16-1, or a Podoviridae, subfamily Autographivirinae, genus T7 virus that is capable of infecting *Klebsiella pneumoniae* strains KP2 and MKP2_251_B;
   d) Group 4: MCoc4c, MCoc6c, Mcoc7c, MCoc3c, MCoc5c, MCoc15c, MCoc8a, MCoc9-2c, M16-9-1c, MCoc9-1c, or Podoviridae, subfamily Autographivirinae, genus Kp34 virus that is capable of infecting at least three of *Klebsiella pneumoniae* strains: CT-141-1, CT-123-1, MKP2_2161 1, and MKP2_251_C;
   e) Group 5: 8M-8, or a family Myoviridae, subfamily Vequintavirinae, genus Sc1 virus that is capable of infecting *Klebsiella pneumoniae* strains CT-123-1, MKP2_2161_1, and 8M-all; and
   f) Group 6: 8M-1, 8M-7, 1.2-3s or a Siphoviridae that is capable of infecting at least two of *Klebsiella pneumoniae* strains: KP2, CT-123-1, MKP2_2161_1, MKP2_251_B, and 8M-all, wherein the composition is capable of lysing each of *Klebsiella pneumoniae* strain KP2, and at least four *Klebsiella pneumoniae* strains selected from CT-141-1, CT-123-1, MKP2_2161_1, MKP2_251_B, MKP2_251_C and 8M-all.

2. The method of claim 1, wherein the pharmaceutical composition is capable of lysing each of *Klebsiella pneumoniae* strains: KP2, CT-141-1, CT-123-1, MKP2_2161 1, MKP2_251_B, MKP2_251_C and 8M-all.

3. The method of claim 1, wherein the pharmaceutical composition comprises bacteriophages MCoc5c and 8M-7 and lytic bacteriophages selected from at least one of Groups 1-3 and 5.

4. The method of claim 3, wherein the pharmaceutical composition additionally comprises at least one bacteriophage selected from the group consisting of 1.2-3b, 1.2-2, and 1.2-3s.

5. The method of claim 4, wherein the pharmaceutical composition additionally comprises at least one bacteriophage selected from KP2-5-1 and PKP-55.

6. The method of claim 1, wherein the pharmaceutical composition comprises bacteriophages 1.2-3b, 1.2-2, and 1.2-3s.

7. The method of claim 6, wherein the pharmaceutical composition additionally comprises bacteriophage Mcoc-5c.

8. The method of claim 1, wherein the pharmaceutical composition is formulated for oral or rectal dosing.

9. The method of claim 1, wherein the lytic bacteriophages are selected from at least four of the Groups 1-6.

10. The method of claim 1, wherein the inflammatory bowel disease is ulcerative colitis.

11. The method of claim 1, wherein the inflammatory bowel disease is Crohn's disease.

12. The method of claim 1, wherein the subject is infected with *Klebsiella* strain KP2.

13. The method of claim 1, wherein the subject is infected with a mutant KP2.

* * * * *

UNITED STATES PATENT AND TRADEMARK OFFICE
CERTIFICATE OF CORRECTION

PATENT NO. : 12,390,499 B2
APPLICATION NO. : 17/436693
DATED : August 19, 2025
INVENTOR(S) : Kenya Honda et al.

Page 1 of 1

It is certified that error appears in the above-identified patent and that said Letters Patent is hereby corrected as shown below:

In the Claims

At Column 71, Claim 1, Line 10, please replace "MKP2_21611" with --MKP2_2161_1--.

At Column 71, Claim 1, Line 18, please replace "MKP2_2161 1" with --MKP2_2161_1--.

At Column 71, Claim 1, Line 29, please replace "MKP2_2161 1" with --MKP2_2161_1--.

At Column 72, Claim 2, Line 7, please replace "MKP2_2161 1" with --MKP2_2161_1--.

Signed and Sealed this
Fourth Day of November, 2025

John A. Squires
*Director of the United States Patent and Trademark Office*